Figure 1A:
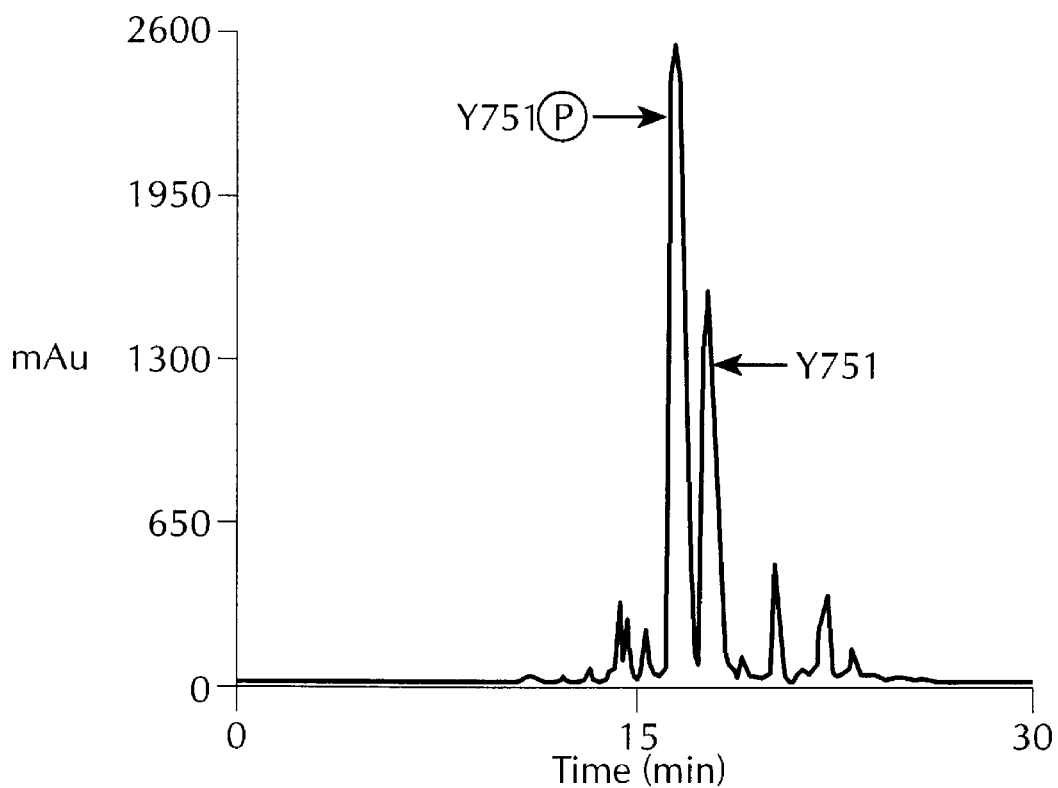
Figure 1B:
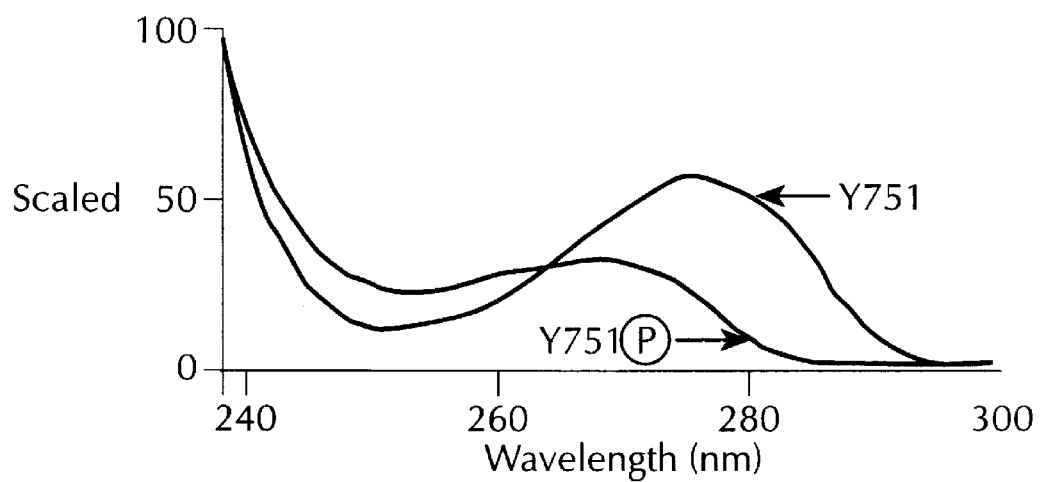
Figure 1C:
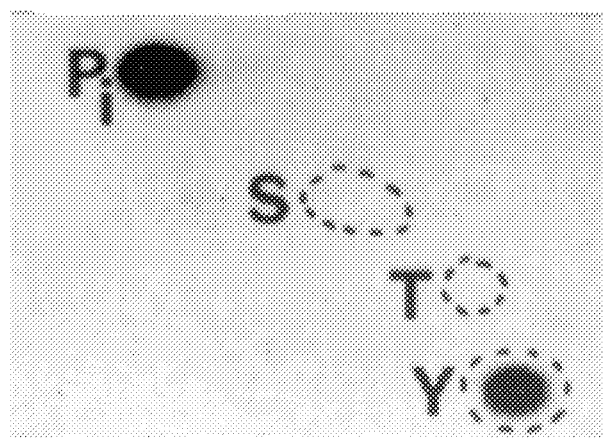
Figure 1D:
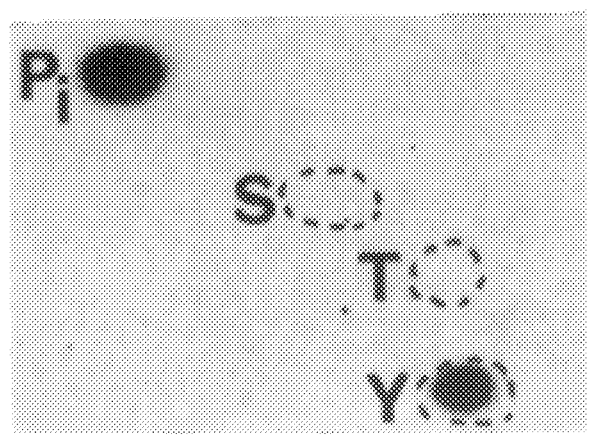

United States Patent [19]
Hiles et al.

[11] Patent Number: 5,846,824
[45] Date of Patent: Dec. 8, 1998

[54] POLYPEPTIDES HAVING KINASE ACTIVITY, THEIR PREPARATION AND USE

[75] Inventors: Ian D. Hiles; Michael J. Fry; Ritu Dhand; Michael D. Waterfield; Peter J. Parker; Masayuki Otsu; George Panayoutou; Stefano Volinia; Ivan Gout, all of London, England

[73] Assignee: Ludwig Institute for Cancer Research, New York, N.Y.

[21] Appl. No.: 780,872

[22] Filed: Jan. 9, 1997

Related U.S. Application Data

[62] Division of Ser. No. 162,081, Feb. 7, 1994.
[51] Int. Cl.$^6$ ............................... C12N 5/10; C12N 5/16; C12N 15/54; C12N 15/63
[52] U.S. Cl. ...................... 435/348; 435/320.1; 435/325; 536/23.2; 536/24.3
[58] Field of Search .................................. 536/23.2, 23.5, 536/24.3; 435/320.1, 325, 348, 252.3, 254.11

[56] References Cited

PUBLICATIONS

Otsu et al., Cell 65:91–104, 1991.

*Primary Examiner*—Eric Grimes
*Attorney, Agent, or Firm*—Fulbright & J Worski

[57] ABSTRACT

This invention relates to new polypeptides which exhibit kinase activity or, more specifically, which show phosphoinositide (PI) 3-kinase activity. Such polypeptides are involved in pathways responsible for cellular growth and differentiation. An isolated polypeptide which possesses PI3-kinase activity when produced by recombinant production in insect cells is disclosed.

8 Claims, 76 Drawing Sheets

FIG. 2A
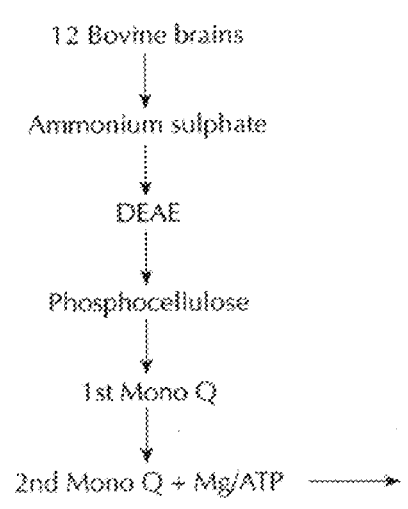
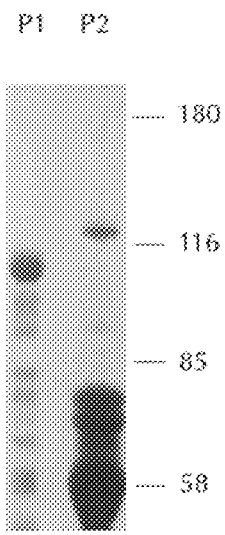
FIG. 2B
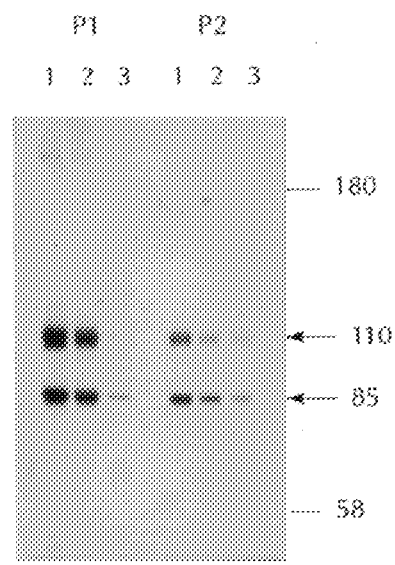

anti-ALPHA anti-BETA

```
751        D M S K D E S V D Y V P M L D M K
751.S            C D E S V D Y V P M L
740              G E S D G G Y M D M S K
1313         E F C P D P L Y E V M L K

Consensus        E E E E Y M P M X X
                 D D D D D   V
```

FIG. 9A

```
  M   P   P   R   P   S   S   G   E   L   W   G   I   H   L   M        16
ATGCCTCCAAGACCATCATCAGGTGAACTGTGGGGCATCCACTTGATG                       48

P   P   R   I   L   V   E   C   L   L   P   N   G   M   I   V        32
CCCCCAAGAATCCTAGTAGAATGTTTACTACCAAATGGATGATAGTG                        96

T   L   E   C   L   R   E   A   T   L   I   T   I   K   H   E        48
ACTTTAGAATGCCTCCGTGAGGCTACGTTAATAACGATAAAGCATGAA                      144

L   F   K   E   A   R   K   Y   P   L   H   Q   L   L   Q   D        64
CTATTTAAAGAAGCAAGAAAATACCCTCTCCATCAACTTCTTCAAGAT                      192

E   S   S   Y   I   F   V   S   V   T   Q   E   A   E   R   E        80
GAATCTTCTTACATTTTCGTAAGTGTTACCCAAGAAGCAGAAAGGGAA                      240

E   F   F   D   E   T   R   R   L   C   D   L   R   L   F   Q        96
GAATTTTTTGATGAAACAAGACGACTTTGTGACCTTCGGCTTTTTCAA                      288

P   F   L   K   V   I   E   P   V   G   N   R   E   E   K   I       112
CCCTTTTTAAAAGTAATTGAACCAGTAGGCAACCGTGAAGAAAAGATC                      336

L   N   R   E   I   G   F   A   I   G   M   P   V   C   E   F       128
CTCAATCGAGAAATTGGTTTTGCTATCGGCATGCCAGTGTGTGAATTC                      384

D   M   V   K   D   P   E   V   Q   D   F   R   R   N   I   L       144
GATATGGTTAAAGATCCAGAAGTACAGGACTTCCGAAGAAATATTCTC                      432
```

FIG. 9B

```
   N   V   C   K   E   A   V   D   L   R   D   L   N   S   P   H        160
AATGTTTGTAAAGAAGCTGTGGATCTTAGGGATCTTAATTCACCTCAT                        480
                  A
   S   R   A   M   Y   V   Y   P   P   N   V   E   S   S   P   E        176
AGTAGAGCAATGTATGTTTATCCTCCAAATGTAGAATCTTCACCAGAA                        528

L   P   K   H   I   Y   N   K   L   D   K   G   Q   I   I   V        192
CTGCCAAAGCACATATATAATAAATTGGATAAAGGGCAAATAATAGTG                        576

V   I   W   V   I   V   S   P   N   N   D   K   Q   K   Y   T        208
GTGATTTGGGTAATAGTTTCTCCAAATAATGACAAACAGAAGTATACT                        624

L   K   I   N   H   D   C   V   P   E   Q   V   I   A   E   A        224
CTGAAAATCAACCATGACTGTGTGCCAGAACAAGTAATTGCTGAAGCA                        672

I   R   K   K   T   R   S   M   L   L   S   S   E   Q   L   K        240
ATCAGGAAAAAAACTCGAAGTATGTTGCTATCATCTGAACAACTAAAA                        720

L   C   V   L   E   Y   Q   G   K   Y   I   L   K   V   C   G        256
CTCTGTGTTTTAGAATATCAGGGCAAGTATATTTTAAAAGTGTGTGGA                        768

C   D   E   Y   F   L   E   K   Y   P   L   S   Q   Y   K   Y        272
TGTGATGAATACTTCCTAGAAAAATATCCTCTGAGTCAGTATAAGTAT                        816

I   R   S   C   I   M   L   G   R   M   P   N   L   M   L   M        288
ATAAGAAGCTGTATAATGCTTGGAGGATGCCCAATTTGATGCTGATG                         864
```

FIG. 9C

```
  A   K   E   S   L   Y   S   Q   L   P   M   D   C   F   T   M     304
GCTAAAGAAAGCCTCTATTCTCAACTGCCAATGGACTGTTTTACAATG                    912

P   S   Y   S   R   R   I   S   T   A   T   P   Y   M   N   G     320
CCATCATATTCCAGACGCATCTCCACAGCTACGCCATATATGAATGGA                    960
                                  B
  E   T   S   T   K   S   L   W   V   I   N   S   A   L   R   I     336
GAAACATCTACAAAATCCCTTTGGGTTATAAATAGTGCACTCAGAATA                    1008

K   I   L   C   A   T   Y   V   N   V   N   I   R   D   I   D     352
AAAATTCTTTGTGCAACCTATGTGAATGTAAATATTCGAGACATTGAC                    1056

K   I   Y   V   R   T   G   I   Y   H   G   G   E   P   L   C     368
AAGATTTATGTTCGAACAGGTATCTACCATGGAGGAGAACCCTTATGT                    1104

D   N   V   N   T   Q   R   V   P   C   S   N   P   R   W   N     384
GATAATGTGAACACTCAAAGAGTACCTTGTTCCAATCCCAGGTGGAAT                    1152

E   W   L   N   Y   D   I   Y   I   P   D   L   P   R   A   A     400
GAATGGCTGAATTACGATATATACATTCCTGATCTTCCTCGTGCTGCT                    1200

R   L   C   L   S   I   C   S   V   K   G   R   K   G   A   K     416
CGACTTTGCCTTTCCATTTGTTCTGTTAAAGGCCGAAAGGGTGCTAAA                    1248

E   E   H   C   P   L   A   W   G   N   I   N   L   F   D   Y     432
GAGGAACACTGTCCATTGGCCTGGGGAAATATAAACTTGTTTGATTAC                    1296
```

FIG. 9D

```
      T   D   T   L   V   S   G   K   M   A   L   N   L   W   P   V      448
     ACAGATACTCTAGTATCTGGAAAAATGGCTTTGAATCTTTGCCAGTA                     1344
                                     C
      P   H   G   L   E   D   L   N   P   I   G   V   T   G   S         464
     CCTCATGGACTAGAAGATTTGCTGAACCCTATTGGTGTTACTGGATCA                    1392

N   P   N   K   E   T   P   C   L   E   L   E   F   D   W   F     480
     AATCCAAATAAAGAAACTCCATGTTTAGAGTTGGAGTTTGACTGGTTC                    1440

S   S   V   V   K   F   P   D   M   S   V   I   E   E   H   A     496
     AGCAGTGTGGTAAAGTTTCCAGATATGTCAGTGATTGAAGAGCATGCC                    1488

N   W   S   V   S   R   E   A   G   F   S   Y   S   H   A   G     512
     AATTGGTCTGTATCCCGTGAAGCAGGATTTAGTTATTCCCATGCAGGA                    1536

L   S   N   R   L   A   R   D   N   E   L   R   E   N   D   K     528
     CTGAGTAACAGACTAGCTAGAGACAATGAATTAAGAGAAAATGATAAA                    1584

E   Q   L   R   A   I   C   T   R   D   P   L   S   E   I   T     544
     GAACAGCTCCGAGCAATTTGTACACGAGATCCTCTATCTGAAATCACT                    1632

E   Q   E   K   D   F   L   W   S   H   R   H   Y   C   V   T     560
     GAGCAAGAGAAAGATTTTCTGTGGAGCCACAGACACTATTGTGTAACT                    1680

I   P   E   I   L   P   K   L   L   L   S   V   K   W   N   S     576
     ATCCCCGAAATTCTACCCAAATTGCTTCTGTCTGTTAAATGGAACTCT                    1728
```

FIG. 9E

```
    R   D   E   V   A   Q   M   Y   C   L   V   K   D   W   P   P        592
   AGAGATGAAGTAGCTCAGATGTACTGCTTGGTAAAAGATTGGCCTCCA                      1776

I   K   P   E   Q   A   M   E   L   L   D   C   N   Y   P   D        608
   ATCAAGCCTGAACAGGCTATGGAGCTTCTGGACTGCAATTACCCAGAT                      1824

P   M   V   R   G   F   A   V   R   C   L   E   K   Y   L   T        624
   CCTATGGTTCGAGGTTTTGCTGTTCGGTGCTTAGAAAAATATTTAACA                      1872
                                                  D
    D   D   K   L   S   Q   Y   L   I   Q   L   V   Q   V   L   K        640
   GATGACAAACTTTCTCAGTACCTAATTCAGCTAGTACAGGTACTAAAA                      1920

Y   E   Q   Y   L   D   N   L   L   V   R   F   L   L   K   K        656
   TATGAACAGTATTTGGATAACCTGCTTGTGAGATTTTTACTCAAAAAA                      1968
                                  E
    A   L   T   N   Q   R   I   G   H   F   F   F   W   H   L   K        672
   GCGTTAACTAATCAAAGGATCGGTCACTTTTTCTTTTGGCATTTAAAA                      2016
                                                  F
    S   E   M   H   N   K   T   V   S   Q   R   F   G   L   L   L        688
   TCTGAGATGCACAATAAAACAGTTAGTCAGAGGTTTGGCCTGCTTTTG                      2064

E   S   Y   C   R   A   C   G   M   Y   L   K   H   L   N   R        704
   GAGTCCTATTGCCGTGCATGTGGATGTATCTGAAGCACCTTAATAGG                       2112
                                              G
    Q   V   E   A   M   E   K   L   I   N   L   T   D   I   L   K        720
   CAAGTTGAGGCTATGGAAAAGCTCATTAACTTGACTGACATTCTCAAA                      2160
```

FIG. 9F

```
  Q   E   K   K   D   E   T   Q   K   V   Q   M   K   F   L   V        736
CAAGAGAAGAAGGATGAAACACAAAAGGTACAGATGAAGTTTTTAGTT                      2208

E   Q   M   R   R   P   D   F   M   D   A   L   Q   G   F   L        752
GAGCAAATGCGGCGACCAGATTTCATGGATGCTCTCCAGGGCTTTCTG                      2256

S   P   L   N   P   A   H   Q   L   G   N   L   R   L   E   E        768
TCTCCTCTAAACCCTGCTCATCAGCTGGGAAATCTCAGGCTTGAAGAG                      2304

C   R   I   M   S   S   A   K   R   P   L   W   L   N   W   E        784
TGTCGAATTATGTCTTCTGCAAAAAGGCCACTGTGGTTGAATTGGGAG                      2352

N   P   D   I   M   S   E   L   L   F   Q   N   N   E   I   I        800
AACCCAGACATCATGTCAGAATTACTCTTTCAGAACAATGAGATCATC                      2400

F   K   N   G   D   D   L   R   Q   D   M   L   T   L   Q   I        816
TTTAAAAATGGGGATGATTTACGGCAAGATATGCTAACCCTTCAGATT                      2448

I   R   I   M   E   N   I   W   Q   N   Q   G   L   D   L   R        832
ATTCGCATTATGGAAAATATCTGGCAAAATCAAGGTCTTGATCTTCGA                      2496

M   L   P   Y   G   C   L   S   I   G   D   C   V   G   L   I        848
ATGTTACCTTATGGATGTCTGTCAATCGGTGACTGTGTGGGACTTATC                      2544

E   V   V   R   N   S   H   T   I   M   Q   I   Q   C   K   G        864
GAGGTGGTGAGAAATTCTCACACTATAATGCAGATTCAGTGTAAAGGA                      2592
```

FIG. 9G

```
            H
 G  L  K  G  A  L  Q  F  N  S  H  T  L  H  Q  W      880
GGCCTGAAAGGTGCACTGCAGTTTAACAGCCACACACTCCATCAGTGG     2640

L  K  D  K  N  K  G  E  I  Y  D  A  A  I  D  L      896
CTCAAAGACAAGAACAAGGGGGAAATATATGATGCGGCCATCGATTTG     2688
            I
 F  T  R  S  C  A  G  Y  C  V  A  T  F  I  L  G      912
TTTACACGATCATGTGCTGGATATTGTGTTGCCACCTTCATTTTGGA      2736

I  G  D  R  H  N  S  N  I  M  V  K  D  D  G  Q      928
ATTGGAGATCGTCACAATAGTAATATCATGGTTAAAGATGATGGACAA     2784
            J
 L  F  H  I  D  F  G  H  F  L  D  H  K  K  K  K      944
CTGTTTCATATAGATTTTGGACACTTTTTGGATCACAAGAAGAAAAAA     2832
            K
 F  G  Y  K  R  E  R  V  P  F  V  L  T  Q  D  F      960
TTTGGTTATAAACGAGAGCGCGTGCCGTTTGTTTTGACACAAGATTTC    2880

L  I  V  I  S  K  G  A  Q  E  C  T  K  T  R  E      976
TTAATAGTGATTAGTAAAGGAGCCCAAGAATGCACAAAGACAAGAGAA    2928

F  E  R  F  Q  E  M  C  Y  K  A  Y  L  A  I  R      992
TTTGAGAGGTTTCAGGAGATGTGTTACAAGGCTTATCTAGCTATTCGG    2976
```

FIG. 9H

```
                         L
     Q H A N L F I N L F S M M L G S        1008
    CAGCATGCCAATCTCTTCATAAATCTTTTCTCAATGATGCTTGGCTCT  3024

G M P E L Q S F D D I A Y I R K        1024
    GGAATGCCAGAACTGCAATCTTTTGATGATATTGCATACATTCGAAAG  3072
                           M
     T L A L D K T E Q E A L E Y F M        1040
    ACCCTAGCTTTAGATAAAACTGAGCAAGAGGCTTTGGAGTATTTCATG  3120

K Q M N D A H H G G W T T K M D        1056
    AAACAAATGAATGATGCACACCATGGTGGCTGGACAACAAAAATGGAT  3168
             N
     W I F H T I K Q H A L N *    1069
    TGGATCTTCCACACAATTAAGCAGCATGCTTTGAACTGA   3207
```

FIG. 10B

```
P110        VCEFDMVKDPEVQDFRRNILNVCKEAVDLRDLNSPHSRAMYVYPPN  170
              ..| :  .| :|.  ::  .|  .:  . . |:.  ..  ...: :...|
VPS34       NITFCVSQDLDVP.LKVKIKSLEGHKPLLKPSQKILNPELMLIGSN   49

171  VESSPEL..PKHIYNKLDKGQIIVVIWVIVSPNNDKQKYTLKINHDCVPE 218
              | .|.:|   . .:::|   . .:.:.|:.    |  .:........:
        50  VFPSSDLIVSLQVFDKERNRNLTLPIYTPYIPFRNSRTWDYWL.......  92

219  QVIAEAIRKKTRSMLLSSEQLKLCVLEYQGKYILKVCGCDEYFLEKYPLS 268
                 .:.  :..:  :  :|| :|::.::||.|
        93  .....TLPIRIKQLTFSS.HLRIILWEYNG.................... 116

269  QYKYIRSCIMLGRMPNIMLMAKESLYSQLPMDCFTMPSYSRRISTATPYM 318
                                                      |...|::
       117  ..........................................SKQIPFF 123

319  NGETSTKSLWVINSALRIKILCATYVNVNIRDIDKIYVRTGIYHGGEPLC 368
              |  |||.   :  :  ::..|:             |::::.:  .|  ::..  .|.:.
       124  NLETSI..FNLKDCTLK.............RGFESLKFRYDVIDHCEVVT 158

369  DNVNTQRVPCSNPRWNEWLNYDIYIPDLPRAARLC.LSICSVKGRKGAKE 417
              || :            .| ||  ..:  .::.|  ::|   :.|:..::  ::::.:.
       159  DNKD..........QENLN.KYFQGEFTRLPWLDEITISKLRKQRENRT 196
```

FIG. 10C

```
418 .EHCPLAWG.NINLFDYTDTLVSGKMAINLWPVPHGLEDLLNPIGVTGS. 464
     .:..:.:. :: :::.. .::. .: .  :|  .| |  |:...
197 WPQGTFVLNLEFPMLELPVVFIEREIMNTQMNIP....TLKNNPGLSTDL 242

465 .NPNKETPCLELEF.DWFSSVVKFPDMSVIEEHANWSVSREAGFSYSHAG 512
     :||::.|  :.:.: |.: |.:|| |    .:::| .. |  ...:|:
243 REPNRNDPQIKISLGDKYHSTLKFYD....PDQPNNDPIEEKYRRLERAS 288

513 LSNRLARDNELRENDKEQLRAICTRDPLSEITEQEKDFLWSHRHYCVTIP 562
    ,..|.:: .   ..:: |. |.. .| ..:|.:||: :|..|.| :. .
289 KNANLDKQVKPDIKKRDYLNKIINYPPGTKLTAHEKGSIWKYRYYLMNNK 338

563 EILPKLLLSVKWNSRDEVAQMYCLVKDWPPIKPEQAMELLDCNYPDPMVR 612
    . |.||| |..:.. .| .::. |:..|:.|. ::|:|||:.:.: ||
339 KALTKLLQSTNLREESERVEVLELMDSWAEIDIDDALELLGSTFKNLSVR 388

613 GFAVRCLEKYLTDDKLSQYLIQLVQVLKYEQY................. 644
    ::||. |.|  .|..|. ||:|||:.: :|..
389 SYAVNRLKK.ASDKELELYLLQLVEAVCFENLSTFSDKSNSEFTIVDAVS 437

645 .........................LDNLLVRFLLKK 656
                             : . |. ||:::
438 SQKLSGDSMLLSTSHANQKLLKSISSESETSGTESLPIVISPLAEFLIRR 487
```

FIG. 10D

```
657  ALTNQRIGHFFFWHLKSEMHNKTVSQRFGLLLESY.CRACGMYLKHLNRQ 705
     ||.|.|:| ||:|.||||  .:|.    :: :|.|: :|   .  || |
488  ALVNPRLGSFFYWYLKSESEDKPY...LDQILSSFWSRLDKKSRNILNDQ 534

706  VEAMEKLINLTDILKQEKKDETQKVQMKF.LVEQMRRPDFMDALQGFLSP 754
     |  :: | : .:.:|. |.....|::: . |:| . || : :...: |
535  VRLINVLRECCETIKRLKDTTAKKMELLVHLLETKVRP..LVKVRPIALP 582

755  LNPAHQLGNLRLEECRIMSSAKRPLWLNWENPDIMSELLFQNNEIIFKNG 804
     |:|.  :.::  |.::::..|. .||.:.:...       || .::|| |
583  LDPDVLICDVCPETSKVFKSSLSPLKITFKTT......LNQPYHLMFKVG 626
                                        *.
805  DDLRQDMLTLQIIRIMENIWQNQGLDLRMLPYGCLSIGDCVGLIEVVRNS 854
     ||||||  |.:|||.:|:::..|:.:||::  ||  .|..|.   | ||.:.|
627  DDLRQDQLVVQIISLMNELLKNENVDLKLTPYKILATGPQEGAIEFIPN. 675
             *.                    .                  .
855  HTIMQIQCK.GGLKGALQFNSHTLHQWLKDKNKGEIYDAAIDLFTRSCAG 903
     .|:  | :|  |: | |.:     ::  .:... :: : .:|  |.:||||
676  DTLASILSKYHGILGYLKL......HYPDENATLGVQGWVLDNFVKSCAG 719
          . *   *  .          ***
904  YCVATFILGIGDRHNSNIMVKDDGQLFHIDFGHFLDHKKKKFGYKRERVP 953
     ||| |:|||:||||  .|::|..||::||  |||.:|::..|.|       |
720  YCVITYILGVGDRHLDNLLVTPDGHFFHADFGYILGQDPKPF.......P 762

954  FVLTQDFLIVISKGAQECTKTREFERFQEMCYKAYLAIRQHANLFINLFS 1003
     ::. . |: . |:.|:.    :::: |.. |: || :|.:|.|::|||.
763  PLMKLPPQIIEAFGGAESS...NYDKFRSYCFVAYSILRRNAGLIINLFE 809

1004 MMLGSGMPE..LQSFDDIAYIRKTLALDKTEQEALEYFMKQMNDAHHGGW 1051
     :| .|.:|:   ::. :.|  :|. :.|:..|::|  .|  .:||.  ::  :
810  LMKTSNIPDIRIDPNGAILRVRERFNLNMSEEDATVHFQNLINDSVNALL 859

1052 TTKMDWIFHTIKQH 1065
     .. :|  :|.: |.
860  PIVIDH.LHNLAQY 872
```

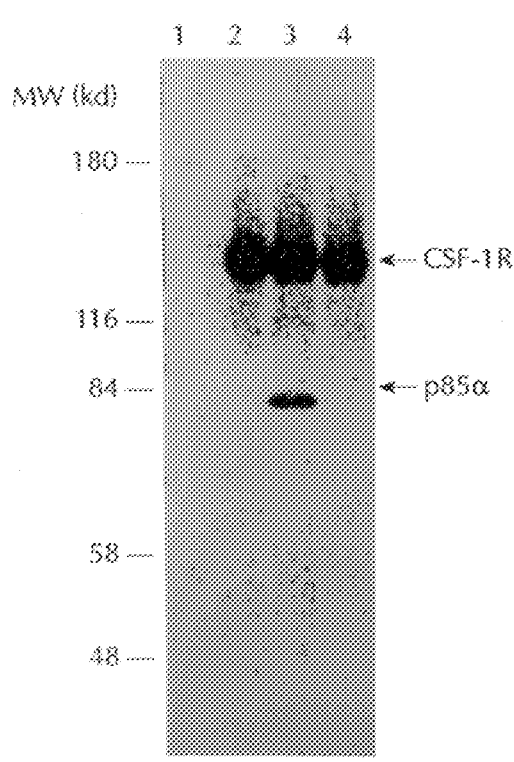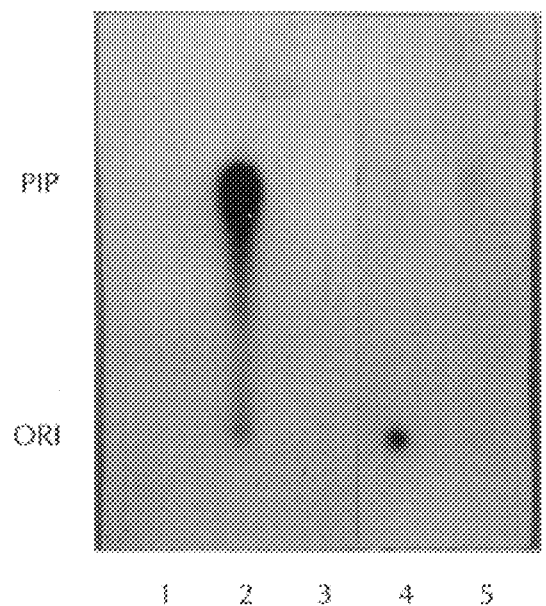
FIG. 14A
FIG. 14B

FIG. 16A

```
1   ATGCCTCCAAGACCATCATCAGGTGTGAACTGTGGGGCATCCACTTGATG    48
    ----+----+----+----+----+----+----+----+----+----+
    TACGGAGGTTCTGGTAGTAGTCCACTTGACACCCGTAGGTGAACTAC
    M   P   P   R   P   S   S   G   E   L   W   G   I   H   L   M

49  CCCCCAAGAATCCTAGTGGAATGTTTACTACCAAATGGAATGATAGTG     96
    ----+----+----+----+----+----+----+----+----+----+
    GGGGGTTCTTAGGATCACCTTACAAATGATGGTTTACCTTACTATCAC
    P   P   R   I   L   V   E   C   L   L   P   N   G   M   I   V

97  ACTTTAGAATGCCTCCGTGAGGCTACATTAGTAACTATAAAGCATGAA    144
    ----+----+----+----+----+----+----+----+----+----+
    TGAAATCTTACGGAGGCACTCCGATGTAATCATTGATATTTCGTACTT
    T   L   E   C   L   R   E   A   T   L   V   T   I   K   H   E

145 CTATTTAAAGAAGCAAGAAAATACCCTCTCCATCAACTTCTTCAAGAT    192
    ----+----+----+----+----+----+----+----+----+----+
    GATAAATTTCTTCGTTCTTTTATGGGAGAGGTAGTTGAAGAAGTTCTA
    L   F   K   E   A   R   K   Y   P   L   H   Q   L   L   Q   D
```

FIG. 16B

```
193  GAATCTCTTACATTTTCGTAAGTGTTACCCAAGAAGCAGAAAGGGAA
     ---------+---------+---------+---------+-------  240
     CTTAGAGAATGTAAAAGCATTCACAATGGGTTCTTCGTCTTTCCCTT
      E  S  Y  I  F  V  S  V  T  Q  E  A  E  R  E

241  GAATTTTTTGATGAAACAAGACGACTTTGTGATCTTCGGCTTTTTCAA
     ---------+---------+---------+---------+-------  288
     CTTAAAAAACTACTTTGTTCTGCTGAAACACTAGAAGCCGAAAAAGTT
      E  F  F  D  E  T  R  R  L  C  D  L  R  L  F  Q

289  CCATTTTTAAAAGTAATTGAACCAGTAGGCAACCGTGAAGAAAAGATC
     ---------+---------+---------+---------+-------  336
     GGTAAAAATTTTCATTAACTTGGTCATCCGTTGGCACTTCTTTTCTAG
      P  F  L  K  V  I  E  P  V  G  N  R  E  E  K  I

337  CTCAATCGAGAAATTGGTTTTGCTATCGGCATGCCAGTGTGCGAATTT
     ---------+---------+---------+---------+-------  384
     GAGTTAGCTCTTTAACCAAAACGATAGCCGTACGGTCACACGCTTAAA
      L  N  R  E  I  G  F  A  I  G  M  P  V  C  E  F
```

FIG. 16C

```
385  GATATGGTTAAAGATCCTGAAGTACAGGACTTCCGAAGAAATATTCTT
     ----+----+----+----+----+----+----+----+----+  432
     CTATACCAATTTCTAGGACTTCATGTCCTGAAGGCTTCTTTATAAGAA
      D   M   V   K   D   P   E   V   Q   D   F   R   R   N   I   L

433  AATGTTTGTAAAGAAGCTGTGGATCTTAGGGATCTTAATTCACCTCAT
     ----+----+----+----+----+----+----+----+----+  480
     TTACAAACATTTCTTCGACACCTAGAATCCCTAGAATTAAGTGGAGTA
      N   V   C   K   E   A   V   D   L   R   D   L   N   S   P   H

481  AGTAGAGCAATGTATGTCTATCCGCCACACATGTAGAATCTTCACCAGAG
     ----+----+----+----+----+----+----+----+----+  528
     TCATCTCGTTACATACAGATAGGCGGTGTACATCTTAGAAGTGGTCTC
      S   R   A   M   Y   V   Y   P   P   H   V   E   S   S   P   E

529  CTGCCAAAGCACACATATATAATAAATTGGATAGAGAGGCCAAATAATAGTG
     ----+----+----+----+----+----+----+----+----+  576
     GACGGTTCGTGTATATATTATTTAACCTATCTCCGGTTTATTATCAC
      L   P   K   H   I   Y   N   K   L   D   R   G   Q   I   I   V
```

FIG. 16D

```
577  GTGATTTGGGTAATAGTTTCTCCAAATAATGACAAGCAGAAGTATACT   624
     ----+----+----+----+----+----+----+----+----+----
     CACTAAACCCATTATCAAAGAGGTTTATTACTGTTCGTCTTCATATGA
       V  I  W  V  S  P  N  N  D  K  Q  K  Y  T

625  CTGAAAATCAACCATGACTGTGTGCCAGAACAAGTAATTGCTGAAGCA   672
     ----+----+----+----+----+----+----+----+----+----
     GACTTTTAGTTGGTACTGACACACGGTCTTGTTCATTAACGACTTCGT
      L  K  I  N  H  D  C  V  P  E  Q  V  I  A  E  A

673  ATCAGGAAAAAAACTAGAAGTATGTTGCTATCATCTGAACAATTAAAA   720
     ----+----+----+----+----+----+----+----+----+----
     TAGTCCTTTTTTTGATCTTCATACAACGATAGTAGACTTGTTAATTTT
      I  R  K  K  T  R  S  M  L  L  S  S  E  Q  L  K

721  CTCTGTGTTTTAGAATATCAGGGCAAGTACATTTTAAAAGTGTGTGGA   768
     ----+----+----+----+----+----+----+----+----+----
     GAGACACAAAATCTTATAGTCCCGTTCATGTAAAATTTTCACACACCT
      L  C  V  L  E  Y  Q  G  K  Y  I  L  K  V  C  G
```

FIG. 16E

```
     TGTGATGAATACTTCCTAGAAAAATATCCTCTGAGTCAGTATAAGTAT
769  -+----+----+----+----+----+----+----+----+----+  816
     ACACTACTTATGAAGGATCTTTTTATAGGAGACTCAGTCATATTCATA
      C   D   E   Y   F   L   E   K   Y   P   L   S   Q   Y   K   Y

ATAAGAAGCTGTATAATGCTTGGGAGGATGCCCAATTTGAAGATGATG
817  -+----+----+----+----+----+----+----+----+----+  864
     TATTCTTCGACATATTACGAACCCTCCTACGGGTTAAACTTCTACTAC
      I   R   S   C   I   M   L   G   R   M   P   N   L   K   M   M

GCTAAAGAAAGCCCTTTATTCTCAACTGCCAATGGACTGTTTTACAATG
865  -+----+----+----+----+----+----+----+----+----+  912
     CGATTTCTTTCGGAAATAAGAGTTGACGGTTACCTGACAAAATGTTAC
      A   K   E   S   L   Y   S   Q   L   P   M   D   C   F   T   M

CCATCTTATTCCAGACGCATTCCACAGCTACACCATATATGAATGGA
913  -+----+----+----+----+----+----+----+----+----+  960
     GGTAGAATAAGGTCTGCGTAAAGGTCTGATGTGGTATATACTTACCT
      P   S   Y   S   R   R   I   S   T   A   T   P   Y   M   N   G
```

FIG. 16F

```
961   GAAACATCTACAAAATCCCTTTGGGTTATAAATAGAGCACTCAGAATA
      ----+----+----+----+----+----+----+----+----+----  1008
      CTTTGTAGATGTTTTTAGGGAAACCCAATATTTATCTCGTGAGTCTTAT
      E  T  S  T  K  S  L  W  V  I  N  R  A  L  R  I

1009  AAAATTCTTTGTGCAACCTACGTGAATCTAAATATTCGAGACATTGAC
      ----+----+----+----+----+----+----+----+----+----  1056
      TTTTAAGAAACACGTTGGATGCACTTAGATTTATAAGCTCTGTAACTG
      K  I  L  C  A  T  Y  V  N  L  N  I  R  D  I  D

1057  AAGATTTATGTTCGAACAGGTATCTACCATGGAGGAGAACCCTTATGT
      ----+----+----+----+----+----+----+----+----+----  1104
      TTCTAAATACAAGCTTGTCCATAGATGGTACCTCCTCTTGGGAATACA
      K  I  Y  V  R  T  G  I  Y  H  G  G  E  P  L  C

1105  GACAATGTGAACACTCAAAGAGTACCTTGTTCCAATCCCAGGTGGAAT
      ----+----+----+----+----+----+----+----+----+----  1152
      CTGTTACTTGTGAGTTTCTCATGGAACAAGGTTAGGGTCCACCTTA
      D  N  V  N  T  Q  R  V  P  C  S  N  P  R  W  N
```

FIG. 16G

```
1153  GAATGGCTGAATTATGATATATACATTCCTGATCTTCCTCGTGCTGCT  1200
      ----+----+----+----+----+----+----+----+----+----
      CTTACCGACTTAATACTATATATGTAAGGACTAGAAGGAGCACGACGA
      E  W  L  N  Y  D  I  Y  I  P  D  L  P  R  A  A

1201  CGACTTTGCCTTTCCATTTGCTCTGTTAAAGGCCGAAAGGGTGCTAAA  1248
      ----+----+----+----+----+----+----+----+----+----
      GCTGAAACGGAAAGGTAAACGAGACAATTCCGGCTTTCCCACGATTT
      R  L  C  L  S  I  C  S  V  K  G  R  K  G  A  K

1249  GAGGAACACTGTCCATTGGCATGGGGAAATATAAACTTGTTTGATTAC  1296
      ----+----+----+----+----+----+----+----+----+----
      CTCCTTGTGACAGGTAACCGTACCCCTTTATATTTGAACAAACTAATG
      E  E  H  C  P  L  A  W  G  N  I  N  L  F  D  Y

1297  ACAGACACTCTAGTATCTGGAAAAATGGCTTTGAATCTTTGGCCAGTA  1344
      ----+----+----+----+----+----+----+----+----+----
      TGTCTGTGAGATCATAGACCTTTTTACCGAAACTTAGAAACCGGTCAT
      T  D  T  L  V  S  G  K  M  A  L  N  L  W  P  V
```

FIG. 16H

```
1345  CCTCATGGATTAGAAGATTTGCTGAACCCTATTGGTGTTACTGGATCA  1392
      ------+---------+---------+---------+---------+
      GGAGTACCTAATCTTCTAAACGACTTGGGATAACCACAATGACCTAGT
      P  H  G  L  E  D  L  L  N  P  I  G  V  T  G  S

1393  AATCCAAATAAAGAAACTCCATGCTTAGAGTTGGAGTTTGACTGGTTC  1440
      ------+---------+---------+---------+---------+
      TTAGGTTTATTTCTTTGAGGTACGAATCTCAACCTCAAACTGACCAAG
      N  P  N  K  E  T  P  C  L  E  L  E  F  D  W  F

1441  AGCAGTGTGGTAAAGTTCCCAGATATGTCAGTGATTGAAGAGCATGCC  1488
      ------+---------+---------+---------+---------+
      TCGTCACACCATTTCAAGGGTCTATACAGTCACTAACTTCTCGTACGG
      S  S  V  V  K  F  P  D  M  S  V  I  E  E  H  A

1489  AATTGGTCTCTGTATCCCGAGAAGCAGGATTTAGCTATTCCCACGCAGGA  1536
      ------+---------+---------+---------+---------+
      TTAACCAGAGACATAGGGCTCTTCGTCCTAAATCGATAAGGGTGCGTCCT
      N  W  S  V  S  R  E  A  G  F  S  Y  S  H  A  G
```

FIG. 16I

```
      CTGAGTAACAGACTAGCTAGAGACAATGAATTAAGGGAAAATGACAAA
      ---+---------+---------+---------+---------+----  1584
      GACTCATTGTCTGATCGATCTCTGTTACTTAATTCCCTTTTACTGTTT
1537   L  S  N  R  L  A  R  D  N  E  L  R  E  N  D  K

GAACAGCTCAAAGCAATTTCTACACGAGATCCTCTCTCTGAAATCACT
      ---+---------+---------+---------+---------+----  1632
      CTTGTCGAGTTTCGTTAAAGATGTGCTCTAGGAGAGACTTTAGTGA
1585   E  Q  L  K  A  I  S  T  R  D  P  L  S  E  I  T

GAGCAGGAGAAAGATTTTCTATGGAGTCACAGACACTATTGTGTAACT
      ---+---------+---------+---------+---------+----  1680
      CTCGTCCTCTTTCTAAAAGATACCTCAGTGTCTGTGATAACACATTGA
1633   E  Q  E  K  D  F  L  W  S  H  R  H  Y  C  V  T

ATCCCCGAAATTCTACCCAAATTGCTTCTGTCTGTTAAATGGAATTCT
      ---+---------+---------+---------+---------+----  1728
      TAGGGGCTTTAAGATGGGTTTAACGAAGACAGACAATTTACCTTAAGA
1681   I  P  E  I  L  P  K  L  L  S  V  K  W  N  S
```

FIG. 16J

```
1729  AGAGATGAAGTAGCCCAGATGTATTGCTTGGTAAAAGATTGGCCTCCA  1776
      ----+----+----+----+----+----+----+----+----+----
      TCTCTACTTCATCGGGTCTACATAACGAACCATTTCTAACCGGAGGT
       R  D  E  V  A  Q  M  Y  C  L  V  K  D  W  P  P

1777  ATCAAACCTGAACAGGCTATGGAACTTCTGGACTGTAATTACCCAGAT  1824
      ----+----+----+----+----+----+----+----+----+----
      TAGTTTGGACTTGTCCGATACCTTGAAGACCTGACATTAATGGGTCTA
       I  K  P  E  Q  A  M  E  L  L  D  C  N  Y  P  D

1825  CCTATGGTTCGAGGTTTTGCTGTTCGGTGCTTGGAAAAATATTTAACA  1872
      ----+----+----+----+----+----+----+----+----+----
      GGATACCAAGCTCCAAAACGACAAGCCACGAACCTTTTTATAAATTGT
       P  M  V  R  G  F  A  V  R  C  L  E  K  Y  L  T

1873  GATGACAAACTTTCTCAGTATTTAATTCAGCTAGTACAGGTCCTAAAA  1920
      ----+----+----+----+----+----+----+----+----+----
      CTACTGTTTGAAAGAGTCATAAATTAAGTCGATCATGTCCAGGATTTT
       D  D  K  L  S  Q  Y  L  I  Q  L  V  Q  V  L  K
```

FIG. 16K

```
1921                                                            1968
     TATGAACAATATATTTGGATAAACTTGCTTGTGAGATTTTTACTGAAGAAA
     ----+----+----+----+----+----+----+----+----+----+
     ATACTTGTTATATAAACCTATTGAACGAACACTCTAAAAATGACTTCTTT
      Y  E  Q  Y  L  D  N  L  L  V  R  F  L  L  K  K 1969                                                            2016
     GCATTGACTAATCAAAGGATTGGGCACTTTTTTCTTTTTGGCATTAAAAA
     ----+----+----+----+----+----+----+----+----+----+
     CGTAACTGATTAGTTTCCTAACCCGTGAAAAAGAAAAACCGTAAATTTT
      A  L  T  N  Q  R  I  G  H  F  F  F  W  H  L  K 2017                                                            2064
     TCTGAGATGCACAATAAAAACAGTTAGCCAGAGGTTTGGCCCTGCTTTTG
     ----+----+----+----+----+----+----+----+----+----+
     AGACTCTACGTGTTATTTTGTCAATCGGTCTCCAAACCGGACGAAAAC
      S  E  M  H  N  K  T  V  S  Q  R  F  G  L  L  L 2065                                                            2112
     GAGTCCTATTGTCGTGCATGTGGGATGTATTTGAAGCACCTGAATAGG
     ----+----+----+----+----+----+----+----+----+----+
     CTCAGGATAACAGCACGTACACCCTACATAAACTTCGTGGACTTATCC
      E  S  Y  C  R  A  C  G  M  Y  L  K  H  L  N  R
```

FIG. 16L

```
2113  CAAGTCGAGGCAATGGAAAAGCTCATTAACTTAACTGACATTCTCAAA  2160
      ----+----+----+----+----+----+----+----+----+----+
      GTTCAGCTCCGTTACCTTTTCGAGTAATTGAATTGACTGTAAGAGTTT
      Q  V  E  A  M  E  K  L  I  N  L  T  D  I  L  K

2161  CAGGAGAGGAAGGATGAAAACACAAAAGGTACAGATGAAGTTTTTAGTT  2208
      ----+----+----+----+----+----+----+----+----+----+
      GTCCTCTCCTTCCTACTTTGTGTTTTCCATGTCTACTTCAAAAATCAA
      Q  E  R  K  D  E  T  Q  K  V  Q  M  K  F  L  V

2209  GAGCAAAATGAGGCGACCAGATTTCATGGATGCCCTACAGGGCTTGCTG  2256
      ----+----+----+----+----+----+----+----+----+----+
      CTCGTTTACTCCGCTGGTCTAAAGTACCTACGGGATGTCCCGAACGAC
      E  Q  M  R  R  P  D  F  M  D  A  L  Q  G  L  L

2257  TCTCCTCTAAACCCTGCTCATCAACTAGGAAACCTCAGGCTTAAAGAG  2304
      ----+----+----+----+----+----+----+----+----+----+
      AGAGGAGATTTGGGACGAGTAGTTGATCCTTTGGAGTCCGAATTTCTC
      S  P  L  N  P  A  H  Q  L  G  N  L  R  L  K  E
```

FIG. 16M

```
      TGTCGAATTATGTCTTCTGCAAAAAGGCCACTGTGGTTGAATTGGGAG
2305  ----+----+----+----+----+----+----+----+----+----  2352
      ACAGCTTAATACAGAAGACGTTTTTCCGGTGACACCAACTTAACCCTC
       C  R  I  M  S  S  A  K  R  P  L  W  L  N  W  E

AACCCAGACACATCATGTCAGAGTTACTGTTTCAGAACAATGAGATCATC
2353  ----+----+----+----+----+----+----+----+----+----  2400
      TTGGGTCTGTGTAGTACAGTCTCAATGACAAAGTCTTGTTACTCTAGTAG
       N  P  D  I  M  S  E  L  L  F  Q  N  N  E  I  I

TTTAAAAAATGGGGATGATTTACGGCAAGATATGCTAACACTTCAAATT
2401  ----+----+----+----+----+----+----+----+----+----  2448
      AAATTTTTACCCCTACTAAATGCCGTTCTATACGATTGTGAAGTTTAA
       F  K  N  G  D  D  L  R  Q  D  M  L  T  L  Q  I

ATTCGTATTATGGAAAATATCTGGCAAAATCAAGGTCTTGATCTTCGA
2449  ----+----+----+----+----+----+----+----+----+----  2496
      TAAGCATAATACCTTTTATAGACCGTTTTAGTTCCAGAACTAGAAGCT
       I  R  I  M  E  N  I  W  Q  N  Q  G  L  D  L  R
```

FIG. 16N

```
2497  ATGTTACCTTATGGTTGTCTGTCAATCGGTGACTGTGTGGGACTTATT  2544
      ----+----+----+----+----+----+----+----+----+----
      TACAATGGAATACCAACAGACAGTTAGCCACTGACACACCCTGAATAA
       M  L  P  Y  G  C  L  S  I  G  D  C  V  G  L  I

2545  GAGGTGGTGCGAAATTCTCACACTATTATGCAAATTCAGTGCAAAGGC  2592
      ----+----+----+----+----+----+----+----+----+----
      CTCCACCACGCTTTAAGAGTGTGATAATACGTTTAAGTCACGTTTCCG
       E  V  V  R  N  S  H  T  I  M  Q  I  Q  C  K  G

2593  GGCTTGAAAGGTGCACTGCAGTTCAACAGCCACACTACATCAGTGG   2640
      ----+----+----+----+----+----+----+----+----+----
      CCGAACTTTCCACGTGACGTCAAGTTGTCGGTGTGATGTAGTCACC
       G  L  K  G  A  L  Q  F  N  S  H  T  L  H  Q  W

2641  CTCAAAGACAAGAACAAAGGAGAGAAATATATGATGCAGCCATTGACCTG  2688
      ----+----+----+----+----+----+----+----+----+----
      GAGTTTCTGTTCTTGTTTCCTCTCTTTATATACTACGTCGGTAACTGGAC
       L  K  D  K  N  K  G  E  I  Y  D  A  A  I  D  L
```

FIG. 16O

```
2689  TTTACACGTTCATGTGCTGGATACTGTGTAGCTACCTTCATTTTGGGA
      ------+---------+---------+---------+---------+  2736
      AAATGTGCAAGTACACGACCTATGACACATCGATGGAAGTAAAACCCT
       F  T  R  S  C  A  G  Y  C  V  A  T  F  I  L  G

2737  ATTGGAGATCGTCACAATAGTAACATCATGGTGAAAGACGATGGACAA
      ------+---------+---------+---------+---------+  2784
      TAACCTCTAGCAGTGTTATCATTGTAGTACCACTTTCTGCTACCTGTT
       I  G  D  R  H  N  S  N  I  M  V  K  D  D  G  Q

2785  CTGTTTCATATAGATTTTGGACACTTTTTGGATCACAAGAAGAAAAAA
      ------+---------+---------+---------+---------+  2832
      GACAAAGTATATCTAAAACCTGTGAAAACCTAGTGTTCTTCTTTTTT
       L  F  H  I  D  F  G  H  F  L  D  H  K  K  K  K

2833  TTTGGTTATAAACGAGAACGTGTGCCATTTGTTTTGACACAGGATTTC
      ------+---------+---------+---------+---------+  2880
      AAACCAATATTTGCTCTTGCACACGGTAAACAAAACTGTGTCCTAAAG
       F  G  Y  K  R  E  R  V  P  F  V  L  T  Q  D  F
```

FIG. 16P

```
2881  TTAATAGTGATTAGTAATAAGGAGCCCAAGAATGCACAAAGACAAGAGAA
      --------+---------+---------+---------+---------+  2928
      AATTATCACTAATCATTCCCTCGGGTTCTTACGTGTTTCTGTTCTCTT
       L  I  V  I  S  K  G  A  Q  E  C  T  K  T  R  E

2929  TTTGAGAGGTTTCAGGAGATGTGTTACAAGGCTTATCTAGCTATTCGA
      --------+---------+---------+---------+---------+  2976
      AAACTCTCCAAAGTCCTCTACACAATGTTCCGAATAGATCGATAAGCT
       F  E  R  F  Q  E  M  C  Y  K  A  Y  L  A  I  R

2977  CAGCATGCCAATCTCTTCAGTATGATGCTTGGCTCT
      --------+---------+---------+---------+---------+  3024
      GTCGTACGGTTAGAGAAGTATTAGAAAGAGTTACTACGAACCGAGA
       Q  H  A  N  L  F  I  N  L  F  S  M  M  L  G  S

3025  GGAATGCCAGAACTACAACAATCTTTTGATGACATTGCATACATTCGAAAG
      --------+---------+---------+---------+---------+  3072
      CCTTACGGTCTTGATGTTAGAAAACTACTGTAACGTATGTAAGCTTTC
       G  M  P  E  L  Q  S  F  D  D  I  A  Y  I  R  K
```

FIG. 16Q

```
3073  ACCCTAGCCTTAGATAAAACTGAGCAAGAGGCTTTGGAGTATTTCATG  3120
      ----+----+----+----+----+----+----+----+
      TGGGATCGGAATCTATTTTGACTCGTTCTCCGAAACCTCATAAAGTAC
       T  L  A  L  D  K  T  E  Q  E  A  L  E  Y  F  M

3121  AAACAAAATGAATGATGCACATCATGGTGGCTGGACAACAAAAATGGAT  3168
      ----+----+----+----+----+----+----+----+
      TTTGTTTTACTTACTACGTGTAGTACCACCGACCTGTTGTTTTACCTA
       K  Q  M  N  D  A  H  H  G  G  W  T  T  K  M  D

3169  TGGATCTTCCACACAATTAAACAGCATGAACTGAAAGATAACT  3216
      ----+----+----+----+----+----+----+----+
      ACCTAGAAGGTGTGTTAATTTGTCGTACGTAACTTGACTTTCTATTGA
       W  I  F  H  T  I  K  Q  H  A  L  N  *

3217  GAGAAAATGAAAGCTCACTCTGGATTCCACACTGCACTGTTAATAACT  3264
      ----+----+----+----+----+----+----+----+
      CTCTTTTACTTTCGAGTGAGACCTAAGGTGTGACGTGACAATTATTGA
```

FIG. 16R

```
      CTCAGCAGGCAAAGACCGATTGCATAGGAATTGCACAATCCATGAACA
      ----+----|----+----|----+----|----+----|----+---   3312
      GAGTCGTCCGTTTCTGGCTAACGTATCCTTAACGTGTTAGGTACTTGT
3265

GCATTAGATTTACAGCAAGAACAGAAATAAAATACTATATAATTTAAA
      ----+----|----+----|----+----|----+----|----+---   3360
      CGTAATCTAAATGTCGTTCTTGTCTTTATTTTATGATATATTAAATTT
3313

TAATGTAAACGCAAACAGGGTTTGATAGCACTTAAACTAGTTCATTTC
      ----+----|----+----|----+----|----+----|----+---   3408
      ATTACATTTGCGTTTGTCCCAAACTATCGTGAATTTGATCAAGTAAAG
3361

AAAA
      ----   3412
      TTTT
3409
```

FIG. 17A

```
hum110   1 ATGCCTCCAAGACCATCATCAGGTGAACTGTGGGGCATCCACTTGATGCC  50
           ||||||||||||||||||||||||||||||||||||||||||||||||||
bov110   1 ATGCCTCCAAGACCATCATCAGGTGAACTGTGGGGCATCCACTTGATGCC  50

51 CCCAAGAATCCTAGTGGAATGTTTACTACCAAATGGAATGATAGTGACTT 100
           |||||||||||||||| ||||| |||||||||||||||||||||||||||
        51 CCCAAGAATCCTAGTAGAATGTTTACTACCAAATGGATGATAGTGACTT 100

101 TAGAATGCCTCCGTGAGGCTACACATTAGTAACTATAAAGCATGAACTATTT 150
           ||||||||||||||||||||| |||||| ||| ||||||||||||||||
       101 TAGAATGCCTCCGTGAGGCTACGTTAATAACGATAAAGCATGAACTATTC 150

151 AAAGAAGCAAGAAAAATACCCTCTCCAACTTCTTCAAGATGAATCTTC 200
           ||||||||||||||||||||||||||||||||||||||||||||||||||
       151 AAAGAAGCAAGAAAAATACCCTCTCCATCAACTTCTTCAAGATGAATCTTC 200
```

FIG. 17B

```
201 TTACATTTTCGTAAGTGTTACCCAAGAAGCAGAAAGGGAAGAATTTTTTG 250
    ||||||||||||||||||||||||||||||||||||||||||||||||||
201 TTACATTTTCGTAAGTGTTACCCAAGAAGCAGAAAGGGAAGAATTTTTTG 250

251 ATGAAACAAGACGACTTTGTGATCTTCGGCTTTTTCAACCATTTTTAAAA 300
    |||||||||||||||||||||| ||||||||||||||||| |||||||||
251 ATGAAACAAGACGACTTTGTGACCTTCGGCTTTTTCAACCCTTTTTAAAA 300

301 GTAATTGAACCAGTAGGCAACCGTGAAGAAAAGATCCTCAATCGAGAAAT 350
    ||||||||||||||||||||||||||||||||||||||||||||||||||
301 GTAATTGAACCAGTAGGCAACCGTGAAGAAAAGATCCTCAATCGAGAAAT 350

351 TGGTTTTGCTATCGGCATGCCAGTGTGCGAATTTGATATGGTTAAAGATC 400
    ||||||||||||||||||||||||||| ||||| ||||||||||||||||
351 TGGTTTTGCTATCGGCATGCCAGTGTGTGAATTCGATATGGTTAAAGATC 400

401 CTGAAGTACAGGACTTCCGAAGAAATATTCTTAATGTTTGTAAAGAAGCT 450
    | ||||||||||||||||||||||||||||| ||||||||||||||||||
401 CAGAAGTACAGGACTTCCGAAGAAATATTCTCAATGTTTGTAAAGAAGCT 450
```

FIG. 17C

```
451  GTGGATCTTAGGGATCTTAATTCACCTCATAGTAGAGCAATGTATGTCTA  500
     ||||||||||||||||||||||||||||||||| ||||||||||||| |
451  GTGGATCTTAGGGATCTTAATTCACCTCATAGTAGAGCAATGTATGTTTA  500

501  TCCGCCACATGTAGAATCTTCACCAGAGCTGCCAAAGCACACATATATAATA  550
     |||  ||| |||||||||||||||||||| ||||||||||||||||||||
501  TCCTCCAAATGTAGAATCTTCACCAGAACTGCCAAAGCACACATATATAATA  550

551  AATTGGATAGAGAGGCCAAATAATAGTGGTGATTTGGGTAATAGTTTCTCCA  600
     |||||||||  ||  |||||||||||||||||||||||||||||||||||
551  AATTGGATAAAAGGGCAAATAATAGTGGTGATTTGGGTAATAGTTTCTCCA  600

601  AATAATGACAAGCAGAAGTATACTCTGAAAATCAACCATGACTGTGTGCC  650
     ||||||||||| |||||||||||||||||||||||||||||||||||||
601  AATAATGACAAACAGAAGTATACTCTGAAAATCAACCATGACTGTGTGCC  650

651  AGAACAAGTAATTGCTGAAGCAATCAGGAAAAACTAGAAGTATGTTGC  700
     |||||||||||||||||||||||||||||||||| |||||||||||||
651  AGAACAAGTAATTGCTGAAGCAATCAGGAAAAAACTCGAAGTATGTTGC  700
```

FIG. 17D

```
701  TATCATCTGAACAATTAAAACTCTGTGTTTTAGAATATCAGGGCAAGTAC  750
     ||||||||||||||||||| ||||||||||||||||||||||||||||||
701  TATCATCTGAACAACTAAAACTCTGTGTTTTAGAATATCAGGGCAAGTAT  750

751  ATTTTAAAAGTGTGTGGATGTGATGAATACTTCCTAGAAAAATATCCTCT  800
     |||||||||||||||||||||||||||||||||||||||||||||||||
751  ATTTTAAAAGTGTGTGGATGTGATGAATACTTCCTAGAAAAATATCCTCT  800

801  GAGTCAGTATATAAGAAGCTGTATAATGCTTGGGAGGATGCCCA  850
     ||||||||||||||||||||||||||||||||||||||||||||
801  GAGTCAGTATATAAGAAGCTGTATAATGCTTGGGAGGATGCCCA  850

851  ATTTGAAGATGATGGCTAAAGAAAAGCCTTTATTCTCAACTGCCAATGGAC  900
     ||||| ||| ||||||||||||||||||||| ||||||||||||||||||
851  ATTTGATGCTGATGGCTAAAGAAAAGCCTCTATTCTCAACTGCCAATGGAC  900

901  TGTTTTACAATGCCATCTTATTCCAGACGCCATTCCAGCTACACCATA  950
     |||||||||||||||||| |||||||||||| ||||||||| ||||||
901  TGTTTTACAATGCCATCATATATTCCAGACGCCATCTCCAGCTACGCCATA  950
```

FIG. 17E

```
 951  TATGAATGGAGAGAAACATCTACAAAATCCCTTTGGGTTATAAATAGAGCAC  1000
      ||||||||||||||||||||||||||||||| |||  ||||||||| ||||
 951  TATGAATGGAGAGAAACATCTACAAAATCCCTTTGGGTTATAAATAGTGCAC  1000

1001  TCAGAATAAAAATTCTTTGTGCAACCTACGTGAATCTAAATATTCGAGAC   1050
      ||||||||| ||||||||||||||||| ||||| ||||||||||||||||
1001  TCAGAATAAAAATTCTTTGTGCAACCTATGTGAATGTAAATATTCGAGAC   1050

1051  ATTGACAAGATTTATGTTCGAACAGGTATCTACCATGGAGGAGAACCCTT   1100
      ||||||||||||||||||||||||||||||||||||||||||||||||||
1051  ATTGACAAGATTTATGTTCGAACAGGTATCTACCATGGAGGAGAACCCTT   1100

1101  ATGTGACAATGTGAACACTCAAAGAGTACCTTGTTCCAATCCCAGGTGGA   1150
      |||| ||| |||||||||||||||||||||||||||||||||||||||||
1101  ATGTGATAACGTGAACACTCAAAGAGTACCTTGTTCCAATCCCAGGTGGA   1150

1151  ATGAATGGCTGAATTATGATATATACATTCCTGATCTTCCTGTGCTGCT   1200
      ||||||||||||||| || |||||||||||||||||||||||||||||||
1151  ATGAATGGCTGAATTACGATATATACATTCCTGATCTTCCTGTGCTGCT   1200
```

FIG. 17F

```
1201 CGACTTTGCCTTTCCATTGCTCTGTTAAAGGCCGAAAGGGTGCTAAAGA 1250
     ||||||||||||||||||||||||||||||||||||||||||||||||||
1201 CGACTTTGCCTTTCCATTGTTCTGTTAAAGGCCGAAAGGGTGCTAAAGA 1250

1251 GGAACACTGTCCATTGGGCATGGGGAAATATAAACTTGTTTGATTACACAG 1300
     ||||||||||||||||||||||||||||||||||||||||||||||||||
1251 GGAACACTGTCCATTGGCCTGGGGAAATATAAACTGTTTGATTACACAG 1300

1301 ACACTCTAGTATCTGGAAAAATGGCTTTGAATCTTTGGCCAGTACCTCAT 1350
     | |||||||||||| ||||||||||||||||||||||||||||||||||
1301 ATACTCTAGTATCTGGAAAAATGGCTTTGAATCTTTGGCCAGTACCTCAT 1350

1351 GGATTAGAAGATTTGCTGAACCCTATTGGTGTTACTGGATCAAATCCAAA 1400
     ||| ||||||||||||||||||||||||||||||||||||||||||||||
1351 GGACTAGAAGATTTGCTGAACCCTATTGGTGTTACTGGATCAAATCCAAA 1400

1401 TAAAGAAACTCCATGCTTAGAGTTTGACTGGTTCAGCAGTGTGG 1450
     ||||||||||||||||||||||||||||||||||||||||||||
1401 TAAAGAAACTCCATGTTTAGAGTTTGACTGGTTCAGCAGTGTGG 1450
```

FIG. 17G

```
1451  TAAAGTTCCCAGATATGTCAGTGATTGAAGAGCATGCCAATTGGTCTGTA  1500
      |||||  ||||||||||||||||||||||||||||||||||||||||||
1451  TAAAGTTTCCAGATATGTCAGTGATTGAAGAGCATGCCAATTGGTCTGTA  1500

1501  TCCCGAGAAGCAGGAGATTTAGCTATTCCCACGCAGGACTGAGTAACAGACT  1550
      |||| ||| ||||||||||||||| ||||||  ||||||||||||||||
1501  TCCCGTGAAGCAGGAGATTTAGTTTATTCCCATGCAGGACTGAGTAACAGACT  1550

1551  AGCTAGAGACAATGAATTAAGGGAAAATGACAAAGAACAGCTCAAAGCAA  1600
      |||||||||||||||||||  |||||||  |||||||||||  ||||||
1551  AGCTAGAGACAATGAATTAAGAGAAAATGATAAAGAACAGCTCCGAGCAA  1600

1601  TTTCTACACGAGATCCCTCTCTGAAATCACTGAGCAGGAGAGAAAGATTTT  1650
      ||| ||| |||||||||||||||||||||||||||||| ||||||||||
1601  TTTGTACACGAGATCCCTCTATCTGAAATCACTGAGCAAGAGAAAGATTTT  1650

1651  CTATGGAGTCACAGACACTATTGTGTAACTATCCCCGAAATTCTACCCAA  1700
      || ||||||||||||||||||||||||||||| |||||||||||| |||
1651  CTGTGGAGCCACAGACACTATTGTGTAACTATCCCCGAAATTCTACCCAA  1700
```

FIG. 17H

```
1701  ATTGCTTCTGTCTGTTAAATGGAATTCTAGAGATGAAGTAGCCCAGATGT  1750
      ||||||||||||||||||||||||||||| |||||||||||| |||||||
1701  ATTGCTTCTGTCTGTTAAATGGAACTCTAGAGATGAAGTAGCTCAGATGT  1750

1751  ATTGCTTGGTAAAAGATTGGCCTCCAATCAAACCTGAACAGGCTATGGAA  1800
      ||||||||||||||||| |||||||||||||| |||||||||||||| |
1751  ACTGCTTGGTAAAAGATTGGCCTCCAATCAAGCCTGAACAGGCTATGGAG  1800

1801  CTTCTGGACTGTAATTACCCAGATCCTATGGTTCGAGGTTTTGCTGTTCG  1850
      ||||||||| || |||||||||||||||||||||||||||||||||||||
1801  CTTCTGGACTGCAATTACCCAGATCCTATGGTTCGAGGTTTTGCTGTTCG  1850

1851  GTGCTTGGAAAAATATTTAACAGATGACAAACTTTCTCAGTATTTAATTC  1900
      |||||||||| ||||||| ||||||||||||||||||||||| |||||||
1851  GTGCTTAGAAAAATATTTTACAGATGACAAACTTTCTCAGTACCTAATTC  1900

1901  AGCTAGTACAGGTCCTAAAATATGAACAATATATTTGGATAACTTGCTTGTG  1950
      ||||||||||||| |||||||||||||||| ||||||||||| ||||||||
1901  AGCTAGTACAGGTACTAAAATATGAACAGTATTTGGATAACCTGCTTGTG  1950
```

FIG. 171

```
1951  AGATTTTTACTGAAGAAAGCATTGACTAATCAAAGGATTGGGCACTTTTT  2000
      |||||||||| ||||| ||  ||||   |||||||| || ||||||||
1951  AGATTTTTACTCAAAAAGCGTTAACTAATCAAAGGATCGGTCACTTTTT   2000

2001  CTTTTGGCATTTAAAATCTGAGATGCACAATAAAACAGTTAGCCAGAGGT  2050
      |||||||||||||||||||||||||||||||||||||||| ||||||||
2001  CTTTTGGCATTTAAAATCTGAGATGCACAATAAAACAGTTAGTCAGAGGT  2050

2051  TTGGCCTGCTTTGGAGTCCTATTGTCGTGCATGTGGGATGTATTTGAAG   2100
      |||||||||||||||||||||| ||||||||||||||||| |||||||
2051  TTGGCCTGCTTTTGGAGTCCTATTGCCGTGCATGTGGGATGTATCTGAAG  2100

2101  CACCTGAATAGGCAAGTCGAGGCAATGGAAAAGCTCATTAACTTAACTGA  2150
      ||||| |||||||||||| |||||||||||||||||||||||| |||||
2101  CACCTTAATAGGCAAGTTGAGGCTATGGAAAAGCTCATTAACTTGACTGA  2150

2151  CATTCTCAAACAGGAGAGGAAGAAGATGAAACAAAAGGTACAGATGAAGT  2200
      ||||||||||| ||| |||| ||||||||||||||||||||||||||||
2151  CATTCTCAAACAAGAGAAGAAGAAGATGAAACAAAAGGTACAGATGAAGT  2200
```

FIG. 17J

```
2201 TTTTAGTTGAGCAAATGAGGGCGACCAGATTTCATGGATGCCCTACAGGGC 2250
     |||||||||||||||||||||||||||||||  ||||| ||| |||||||
2201 TTTTAGTTGAGCAAATGCGGGCGACCAGATTTCATGGATGCTCTCCAGGGC 2250

2251 TTGCTGTCTCCTCTAAACCCTGCTCATCAACTAGGAAACCTCAGGCTTAA  2300
     || ||||||||||||||||||||||||||| || || |||| |||||| |
2251 TTTCTGTCTCCTCTAAACCCTGCTCATCAGCTGGGAAATCTCAGGCTTGA  2300

2301 AGAGTGTCGAATTATGTCTTCTGCAAAAGGCCACTGTGGTTGAATTGGG   2350
     ||||||||||||||||||||||||||||| ||||||||||||||||||||
2301 AGAGTGTCGAATTATGTCTTCTGCAAAAAGGCCACTGTGGTTGAATTGGG   2350

2351 AGAACCCAGACATCATGTCAGAGTTACTGTTTCAGAACAATGAGATCATC  2400
     ||||||||||||||||||||| || |||| ||||||||||||||||||||
2351 AGAACCCAGACATCATGTCAGAATTACTCTTTCAGAACAATGAGATCATC  2400

2401 TTTAAAAATGGGGATGATGATTTACGGCAAGATATGCTAACACTTCAAATTAT 2450
     |||||||||||| ||||||||||||||||||||||||||||||  |||||||
2401 TTTAAAAATGGGGATGATTTACGGCAAGATATGCTAACCCTTTCAGATTAT 2450
```

FIG. 17K

```
2451  TCGTATTATGGAAAATATCTGGCAAAATCAAGGTCTCTTGATCTTCGAATGT  2500
      |||  ||||||||||||||||||||||||||||||||||||||||||||||
2451  TCGCATTATGGAAAATATCTGGCAAAATCAAGGTCTTGATCTTCGAATGT   2500

2501  TACCTTATGGTTGTCTGTCAATCGGTGACTGTGTGTGGGACTTATTGAGGTG  2550
      ||||||||| |||| ||||||||||||||||||||||||||||| |||||
2501  TACCTTATGGATGTCTCGTCAATCGGTGACTGTGTGTGGGACTTATCGAGGTG  2550

2551  GTGCCGAATTCTCACACTATTATGCAAATTCAGTGCAAAGGCGGGCTTGAA  2600
      || |||||||||||||||| |||| ||||||||||| || ||| ||||||
2551  GTGAGAAATTCTCACACTATAATGCAGATTCAGTGTAAAGGAGGCCTGAA   2600

2601  AGGTGCACTGCAGTTCAACAGCCACACACTACACATCAGTGGCTCAAAGACA  2650
      |||||||||||||||| |||||||||||||||||||||||||||||||||
2601  AGGTGCACTGCAGTTTAACAGCCACACACTCCATCAGTGGCTCAAAGACA   2650

2651  AGAACAAAGGAGAAAATATGATGCAGCCATTGACCTGTTTACACGTTCA    2700
      |||||||| || |||||||||| ||||||||| ||||| |||||||| ||
2651  AGAACAAGGGGAAAATATGATGCGGCCATTGATTGTTTACACGATCA     2700
```

FIG. 17L

```
2701  TGTGCTGGATACTGTGTAGCTACCTTCATTTTGGGAATTGGAGATCGTCA  2750
      |||||||||||  ||||  ||  || |||||||||||||||||||||||
2701  TGTGCTGGATATTGTGTTGCCACCTTCATTTGGGAATTGGAGATCGTCA  2750

2751  CAATAGTAACATCATGGTGAAAGACGATGGACAACTGTTTCATATAGATT  2800
      |||||||||||||||||  ||||  ||| |||||||||||||||||||||
2751  CAATAGTAATATCATGGTTAAAGATGATGGACAACTGTTTCATATAGATT  2800

2801  TTGGACACTTTTTTGGATCACAAGAAGAAAAAATTTGGTTATAAACGAGAA  2850
      |||||||||||||||||||||||||  ||||||||||||||||||||
2801  TTGGACACTTTTTTGGATCACAAGAAGAAAAAATTTGGTTATAAACGAGAG  2850

2851  CGTGTGCCATTTGTTTTGACACAGGATTTCTTAATAGTGATTAGTAAAGG  2900
      || |||||||| ||||||||||||||| |||||||||||||||||||||
2851  CGCGTGCCGTTTGTTTTGACACAAGATTTCTTAATAGTGATTAGTAAAGG  2900

2901  AGCCCAAGAATGCACAAAGACAAGAGAATTTGAGAGGTTTCAGGAGATGT  2950
      ||||||||||||||||||||||||| |||||||||||||||||||||||
2901  AGCCCAAGAATGCACAAAGACAAGAGAATTTGAGAGGTTTCAGGAGATGT  2950
```

FIG. 17M

```
2951 GTTACAAGGCTTATCTAGCTATTCGACAGCATGCCAATCTCTTCATAAAT 3000
     ||||||||||||||||||||||| ||||||||||||||||||||||||||
2951 GTTACAAGGCTTATCTAGCTATTCGGCAGCATGCCAATCTCTTCATAAAT 3000

3001 CTTTTCTCAATGATGCTTGGCTCTGGAATGCCAGAACTACAATCTTTTGA 3050
     ||||||||||||||||||||| ||||||||||||| ||||||||||||||
3001 CTTTTCTCAATGATGCTTGGCTCTGGAATGCCAGAACTGCAATCTTTTGA 3050

3051 TGACATTGCATACATTCGAAAGACCCTAGCCTTTAGATAAAACTGAGCAAG 3100
     |||  ||||||||.|||||||||||||||| |||||||||||||||||||
3051 TGATATTGCATACATTCGAAAGACCCTAGCTTTAGATAAAACTGAGCAAG 3100

3101 AGGCTTTGGAGTATTTCATGAAACAAATGAATGATGCACATCATGGTGGC 3150
     ||||| |||||||||||||||||||||||||||||||||||||||||||
3101 AGGCTTTGGAGTATTTCATGAAACAAATGAATGATGCACCATGGTGGC 3150

3151 TGGACAACAAAAATGGATTGGATCTTCCACACAATTAAACAGCATGCATT 3200
     ||||||||| |||||||||||||||||||||||||||| ||||||||| |
3151 TGGACAACAAAAATGGATTGGATCTTCCACACAATTAAGCAGCATGCTTT 3200

3201 GAACTGAAAAGATAACTGAGAAAATGAAAGCTCACTCTGGA........
     |||||||
3201 GAACTGA..........................................
```

FIG. 18A

```
              10         20         30         40         50         60
h  MPPRPSSGELWGIHLMPPRILVECLLPNGMIVTLECLREATLVTIKHELFKEARKYPLHQ
   ||||||||||||||||||||||||||||||||||| ||||:|||||||||||||||||||
b  MPPRPSSGELWGIHLMPPRILVECLLPNGMIVTLECLREATLITIKHELFKEARKYPLHQ
              10         20         30         40         50         60

70         80         90        100        110        120
h  LLQDESSYIFVSVTQEAEREEFFDETRRLCDLRLFQPFLKVIEPVGNREEKILNREIGFA
   ||||||||||||||||||||||||||||||||||||||||||||||||||||||||||||
b  LLQDESSYIFVSVTQEAEREEFFDETRRLCDLRLFQPFLKVIEPVGNREEKILNREIGFA
              70         80         90        100        110        120

130        140        150        160        170        180
h  IGMPVCEFDMVKDPEVQDFRRNILNVCKEAVDLRDLNSPHSRAMYVYPPHVESSPELPKH
   |||||||||||||||||||||||||||||||||||||||||||||||:||||||||||||
b  IGMPVCEFDMVKDPEVQDFRRNILNVCKEAVDLRDLNSPHSRAMYVYPPNVESSPELPKH
             130        140        150        160        170        180
```

FIG. 18B

```
              190       200       210       220       230       240
h IYNKLDRGQIIVVIWVIVSPNNDKQKYTLKINHDCVPEQVIAEAIRKKTRSMLLSSEQLK
  ||||||||:|||||||||||||||||||||||||||||||||||||||||||||||||
b IYNKLDKGQIIVVIWVIVSPNNDKQKYTLKINHDCVPEQVIAEAIRKKTRSMLLSSEQLK
              190       200       210       220       230       240

250       260       270       280       290       300
h LCVLEYQGKYILKVCGCDEYFLEKYPLSQYKYIRSCIMLGRMPNLKMMAKESLYSQLPMD
  ||||||||||||||||||||||||||||||||||||||||||::|||||||||||||||
b LCVLEYQGKYILKVCGCDEYFLEKYPLSQYKYIRSCIMLGRMPNLMLMAKESLYSQLPMD
              250       260       270       280       290       300

310       320       330       340       350       360
h CFTMPSYSRRIISTATPYMNGETSTKSLWINRALRIKILCATYVNLNIRDIDKIYVRTGI
  |||||||||||||||||||||||||||||||||||:|||||||||:||||||||||||||
b CFTMPSYSRRIISTATPYMNGETSTKSLWINSALRIKILCATYVNVNIRDIDKIYVRTGI
              310       320       330       340       350       360
```

FIG. 18C

```
            370         380         390         400         410         420
h  YHGGEPLCDNVNTQRVPCSNPRWNEWLNYDIYIPDLPRAARLCLSICSVKGRKGAKEEHC
   ||||||||||||||||||||||||||||||||||||||||||||||||||||||||||||
b  YHGGEPLCDNVNTQRVPCSNPRWNEWLNYDIYIPDLPRAARLCLSICSVKGRKGAKEEHC
            370         380         390         400         410         420

430         440         450         460         470         480
h  PLAWGNINLFDYTDTLVSGKMALNLWPVPHGLEDLLNPIGVTGSNPNKETPCLELEFDWF
   ||||||||||||||||||||||||||||||||||||||||||||||||||||||||||||
b  PLAWGNINLFDYTDTLVSGKMALNLWPVPHGLEDLLNPIGVTGSNPNKETPCLELEFDWF
            430         440         450         460         470         480

490         500         510         520         530         540
h  SSVVKFPDMSVIEEHANWSVSREAGFSYSHAGLSNRLARDNELRENDKEQLKAISTRDPL
   |||||||||||||||||||||||||||||||||||||||||||||||||| ::||||||
b  SSVVKFPDMSVIEEHANWSVSREAGFSYSHAGLSNRLARDNELRENDKEQLRAICTRDPL
            490         500         510         520         530         540
```

FIG. 18D

```
         550        560        570        580        590        600
h SEITEQEKDFLWSHRHYCVTIPEILPKLLSVKWNSRDEVAQMYCLVKDWPPIKPEQAME
  |||||||||||||||||||||||||||||||||||||||||||||||||||||||||||
b SEITEQEKDFLWSHRHYCVTIPEILPKLLSVKWNSRDEVAQMYCLVKDWPPIKPEQAME
         550        560        570        580        590        600

610        620        630        640        650        660
h LLDCNYPDPMVRGFAVRCLEKYLTDDKLSQYLIQLVQVLKYEQYLDNLLVRFLLKKALTN
  |||||||||||||||||||||||||||||||||||||||||||||||||||||||||||
b LLDCNYPDPMVRGFAVRCLEKYLTDDKLSQYLIQLVQVLKYEQYLDNLLVRFLLKKALTN
         610        620        630        640        650        660

670        680        690        700        710        720
h QRIGHFFWHLKSEMHNKTVSQRFGLLLESYCRACGMYLKHLNRQVEAMEKLINLTDILK
  |||||||||||||||||||||||||||||||||||||||||||||||||||||||||||
b QRIGHFFWHLKSEMHNKTVSQRFGLLLESYCRACGMYLKHLNRQVEAMEKLINLTDILK
         670        680        690        700        710        720
```

FIG. 18E

```
           730        740        750        760        770        780
h  QERKDETQKVQMKFLVEQMRRPDFMDALQGLLSPLNPAHQLGNLRLKECRIMSSAKRPLW
   ||:||||||||||||||||||||||||||||||:|||||||||||||||:||||||||||
b  QEKKDETQKVQMKFLVEQMRRPDFMDALQGFLSPLNPAHQLGNLRLEECRIMSSAKRPLW
           730        740        750        760        770        780

790        800        810        820        830        840
h  LNWENPDIMSELLFQNNEIIFKNGDDLRQDMLTLQIIRIMENIWQNQGLDLRMLPYGCLS
   ||||||||||||||||||||||||||||||||||||||||||||||||||||||||||||
b  LNWENPDIMSELLFQNNEIIFKNGDDLRQDMLTLQIIRIMENIWQNQGLDLRMLPYGCLS
           790        800        810        820        830        840

850        860        870        880        890        900
h  IGDCVGLIEVVRNSHTIMQIQCKGGLKGALQFNSHTLHQWLKDKNKGEIYDAAIDLFTRS
   ||||||||||||||||||||||||||||||||||||||||||||||||||||||||||||
b  IGDCVGLIEVVRNSHTIMQIQCKGGLKGALQFNSHTLHQWLKDKNKGEIYDAAIDLFTRS
           850        860        870        880        890        900
```

FIG. 18F

```
           910        920        930        940        950        960
h CAGYCVATFILGIGDRHNSNIMVKDDGQLFHIDFGHFLDHKKKKFGYKRERVPFVLTQDF
  ||||||||||||||||||||||||||||||||||||||||||||||||||||||||||||
b CAGYCVATFILGIGDRHNSNIMVKDDGQLFHIDFGHFLDHKKKKFGYKRERVPFVLTQDF
           910        920        930        940        950        960

970        980        990       1000       1010       1020
h LIVISKGAQECTKTREFERFQEMCYKAYLAIRQHANLFINLFSMMLGSGMPELQSFDDIA
  ||||||||||||||||||||||||||||||||||||||||||||||||||||||||||||
b LIVISKGAQECTKTREFERFQEMCYKAYLAIRQHANLFINLFSMMLGSGMPELQSFDDIA
           970        980        990       1000       1010       1020

1030       1040       1050       1060       1070       1080
h YIRKTLALDKTEQEALEYFMKQMNDAHHGGWTTKMDWIFHTIKQHALNXKITEKMKAHSG
  |||||||||||||||||||||||||||||||||||||||||||||||||||
b YIRKTLALDKTEQEALEYFMKQMNDAHHGGWTTKMDWIFHTIKQHALNX
          1030       1040       1050       1060
```

FIG. 19A

```
  1  MPPRPSSGEL WGIHLMPPRI LVECLLPNGM IVTLECLREA TLVTIKHELF
 51  KEARKYPLHQ LLQDESSYIF VSVTQEAERE EFFDETRRLC DLRLFQPFLK
101  VIEPVGNREE KILNREIGFA IGMPVCEFDM VKDPEVQDFR RNILNVCKEA
151  VDLRDLNSPH SRAMYVYPPH VESSPELPKH IYNKLDRGQI IVVIWVIVSP
201  NNDKQKYTLK IAEAIRKKTR SMLLSSEQLK LCVLEYQGKY
251  ILKVCGCDEY FLEKYPLSQY KYIRSCIMLG RMPNLKMMAK ESLYSQLPMD
301  CFTMPSYSRR ISTATPYMNG ETSTKSLWVI NRALRIKILC ATYVNLNIRD
351  IDKIYVRTGI YHGGEPLCDN VNTQRVPCSN PRWNEWLNYD IYIPDLPRAA
401  RLCLSICSVK GRKGAKEEHC PLAWGNINLF DYTDTLVSGK MALNLWPVPH
451  GLEDLLNPIG VTGSNPNKET PCLELEFDWF SSVVKFPDMS VIEEHANWSV
```

FIG. 19B

```
 501  SREAGFSYSH AGLSNRLARD NELRENDKEQ LKAISTRDPL SEITEQEKDF
 551  LWSHRHYCVT IPEILPKLLL SVKWNSRDEV AQMYCLVKDW PPIKPEQAME
 601  LLDCNYPDPM VRGFAVRCLE KYLTDDKLSQ YLIQLVQVLK YEQYLDNLLV
 651  RFLLKKALTN QRIGHFFFWH LKSEMHNKTV SQRFGLLIES YCRACGMYLK
 701  HLNRQVEAME KLINLTDILK QERKDETQKV QMKFLVEQMR RPDFMDALQG
 751  LLSPLNPAHQ LGNLRLKECR IMSSAKRPLW LNWENPDIMS ELLFQNNEII
 801  FKNGDDLRQD MLTLQIIRIM ENIWQNQGLD LRMLPYGCLS IGDCVGLIEV
 851  VRNSHTIMQI QCKGGLKGAL QFNSHTLHQW LKDKNKGEIY DAAIDLFTRS
 901  CAGYCVATFI LGIGDRHNSN IMVKDDGQLF HIDFGHFLDH KKKKFGYKRE
 951  RVPFVLTQDF LIVISKGAQE CTKTREFERF QEMCYKAYLA IRQHANLFIN
1001  LFSMMLGSGM PELQSFDDIA YIRKTLALDK TEQEALEYFM KQMNDAHHGG
1051  WTTKMDWIFH TIKQHALN*
```

FIG. 20

```
  1  GGAGACGACTGGCGACAGGATCAACTTATTCTTCAAATCATTCACTC
     GlyAspAspLeuArgGlnAspGlnLeuLeuGlnIleIleSerLeu

49  ATGGACAAGCTGTTACGGAAAGAAATCTGGACTTGAAATTGACACCT
     MetAspLysLeuArgLysGluAsnLeuAspLeuLysLeuThrPro

97  TATAAGGTGTTAGCCACCAGTACAAAACATGGCTTCATGCAGtTTATC
     TyrLysValLeuAlaThrSerThrLysHisGlyPheMetGlnPheIle

145  CAGTCAGTtCCTGTGGCTGAAGTTCTTGATACAGAGGAAGCATTCAG
     GlnSerValProValAlaGluValLeuAspThrGluGlySerIleGln

193  AACTTTTTAGAAATATGCACCAAGTGAGAATGGGCCAAATGGGATT
     AsnPhePheArgLysTyrAlaProSerGluAsnGlyProAsnGlyIle

241  AGTGCTGAGGTCATGGACACTtACGTTAAAAGCTGTGCTGGATATTGC
     SerAlaGluValMetAspThrTyrValLysSerCysAlaGlyTyrCys

289  GTGATCACCTATATACTTGGAGTTGGAGACAGGCACCTGGATAACCTT
     ValIleThrTyrIleLeuGlyValGlyAspArgHisLeuAspAsnLeu

337  TTGCTAACCAAAACAGGCAAACTCTTCCACATCGATTTCGGCCAC
     LeuLeuThrLysThrGlyLysLeuPheHisIleAspPheGlyHis
```

FIG. 21

```
  1  GGGGATGACTTACGGCAGGACATGCTAACGCTGCAGATGATTCGCATC
     GlyAspAspLeuArgGlnAspMetLeuThrLeuGlnMetIleArgIle

49  ATGAGCAAGATCTGGGTCCAGGAGGGCTGGACATGCCATGGTCATC
     MetSerLysIleTrpValGlnGluGlyLeuAspMetArgMetValIle

97  TTCCGCTGCTTCTCCACCGGCAGAGGGATGGTGGAGATGATC
     PheArgCysPheSerThrGlyArgGlyMetValGluMetIle

145  CCTAATGCTGAGACCCTGCGTAAGATCCAGGTGGAGCATGGGGTGACc
     ProAsnAlaGluThrLeuArgLysIleGlnValGluHisGlyValThr

193  GGCTCGTTCAAGGACCGGCCCCTGGCAGACCGGCTGCAGAAACACAAC
     GlySerPheLysAspArgProLeuAlaAspArgLeuGlnLysHisAsn

241  CCTGGGGAGGACGAGTATGAGAAGGCTGTGGaGAACTTTATCTACTCC
     ProGlyGluAspGluTyrGluLysAlaValGluAsnPheIleTyrSer

289  TGCGCTGGCTGCTGCTGCCACGTACGTCTTGGGCATCTGTGACga
     CysAlaGlyCysCysValAlaThrTyrValLeuGlyIleCysAspArg

337  CATAAATGACAACATCATGCTGAAGACCACTGGTCACATGTTCCACATC
     HisAsnAspAsnIleMetLeuLysThrThrGlyHisMetPheHisIle

385  GACTTCGGC
     AspPheGly
```

FIG. 22

```
                1                                                      50
vps34       GDDLRQDqLvvQIIslMnellknEnvDLkLtPYkiLaTGpqeGaIEfIpN
PITR-c      GDDLRQDqLiLQIIslMdkllrkEnLDLkLtPYkvLaTstkhGFmqfIqs
humpl10     GDDLRQDmLtLQIIriMeniwqngqLDLrMlPYgcLsiGdcvGLIEvVrN
PITR-f      GDDLRQDmLtLQmIriMskiwvqEgLDMrMviFrcFsTGrgrGMVEmIpN
Consensus   GDDLRQD-L-LQII---M-----E-LDL---PY--L-TG---G--IE-I-N 51                                                    100
vps34       dtlasilskyhGIiGy........LklhypdeNatlgVqgwvlDnFVkSCA
PITR-c      vpvaevldtegsIqmf........FrkYapseNgpngIsaevmDtYVkSCA
humpl10     shtimqiqckgGLkGalqfnshtLhqWlkdkNkge.IydaaiDlFtrSCA
PITR-f      aetlrkiqvehgGVtGs..fkdrpLadrlqkhNpgedeyekavEnFIySCA
Consensus   ------------GI-G-------L------N-----I-----D-FV-SCA 101                                         133
vps34       GYCViTYILGVGDRHIDNlLvtpdGhFFHaDEG
PITR-c      GYCViTYILGVGDRHIDNlLltktGkLFHIDEG
humpl10     GYCVaTFILGIGDRHnsNiMvkddGqLFHIDEG
PITR-f      GCCVaTYVLGIcDRHnDNiMlkttGhMFHIDEG
Consensus   GYCV-TYILG-GDRH-DN------G-LFHIDEG
```

POLYPEPTIDES HAVING KINASE ACTIVITY, THEIR PREPARATION AND USE

This application is a Divisional of Ser. No. 08/162,081 filed Feb. 7, 1994.

This invention relates to new polypeptides which exhibit kinase activity. More specifically, the invention is concerned with polypeptides which show phosphoinositide (hereinafter "PI")3-kinase activity, particularly molecules involved in pathways responsible for cellular growth and differentiation.

Major advances have taken place in our knowledge of the structure and function of the signal transducing molecules and second messenger systems coupled to cell surface receptors. Thus, a subset of polypeptide growth factor receptors belong to the family of protein-tyrosine kinases (hereinafter "PTK" and activation of these receptors following ligand binding involves autophosphorylation of the receptor as well as phosphorylation of a number of intracellular substrate proteins (reviewed in Ullrich, A et al., 1990). The importance of receptor autophosphorylation had been unclear until recently, when evidence from several laboratories has suggested that this event may mediate the formation of complexes between receptor proteins and putative growth regulatory proteins such as phospholipase Cγ(PLCγ) (Meisenhelder et al, 1989), phosphatidylinositol PI3-kinase (Coughlin, S R et al, 1989). GTPase-activating protein (GAP) (Kaplan et al, 1990), the serine/theonine kinase Raf (Morrison et al, 1989), and members of the src-family of protein-tyrosine kinases (Kypta, R M et al., 1990) (reviewed in Cantley, L C et al., 1991).

The association of PI kinase activity with activated receptors is of particular interest since increased turnover of PI and its phosphorylated derivatives has been implicated in the action of hormones, growth factors and transformation of cells by DNA and RNA viruses (reviewed in Whitman, M et al., 1988; Cantley et al., 1991). Several species of PI kinase are known to exist, but up to now none of these enzymes have been characterised by cloning and expression and the demonstration of PI kinase activity. Fibroblasts contain at least two PI kinase activities which are distinguishable on the basis of their detergent sensitivity and kinetic properties (Whitman, M et al., 1987). These two activities were classified as Type I (inhibited by non-ionic detergents) and Type II (stimulated by non-ionic detergents and inhibited by adenosine). A third distinct species (Type III) has been identified in bovine brain but remains poorly characterised (Enderman, G et al., 1987). One species of PI kinase activity in particular has become of major interest in the search for second messenger systems linked to protein-tyrosine kinases because this activity was shown to co-immunoprecipitate with activated platelet-derived growth factor (PDGF) receptors (Kaplan, D R et al., 1987; Coughlin, S R et al., 1989) and with the polyoma middle T antigen/pp60$^{c-src}$ (mT:pp60$^{c-src}$) complex (Whitman, M et al., 1985). This activity has been shown to be due to a Type I PI kinase which produces novel inositol lipids phosphorylated at the D-3 position of the inositol ring (Whitman, M et al., 1988). More recently this enzyme has also been shown to associate with the CSF-1 receptor (Varticovski, L et al., 1989) kit (Lev et al, 1991), the epidermal growth factor (EGF) receptor (Bjorge et al, 1990), the PDGF α-receptor (Yu et al, 1991), the insulin receptor (Ruderman et al, 1990), the hepatocyte growth factor receptor, Met (Graziani et al, 1991), and with activated non-receptor protein-tyrosine kinases (Fukui & Hanafusa, 1989; Chan et al, 1990; Varticovski et al, 1991).

PI3 kinase activity has been closely linked to the presence of 81/85 kD proteins in these immunoprecipitates which can be phosphorylated on tyrosine residues by the associated protein-tyrosine kinase both in vitro and in vivo (Kaplan, D R et al., 1987; Courtneidge, S A et al., 1987; Cohen et al, 1990). Recently a 650 fold purification of PI3-kinase from bovine brain was described which, among other proteins present in the purest preparation, contained an 85 kD protein which was shown to be an in vitro substrate for the PDGF and EGF receptors (Morgan, S J et al., 1990). Using sequence information from tryptic peptides derived from this protein, two homologous bovine p85 proteins, denoted p85α and p850β (Otsu, M et al., 1991) have recently been cloned. Two other groups have independently cloned murine and human p85α homologues using different strategies (Escobedo, J A et al., 1991b; Skolnik, E Y et al., 1991). Both of these p85 proteins can be demonstrated to bind directly to phosphorylated PDGF receptor in vitro (Otsu, M et al., 1991; Escobedo, J A et al., 1991b). These proteins may function as the receptor binding subunits of the PI3-kinase since neither of them can be shown to encode intrinsic PI3-kinase activity when expressed in a variety of cell systems (Otsu, M et al., 1991; Escobedo, J A et al., 1991b). However, immunoprecipitation of $^{125}$I-labelled bovine brain PI3-kinase with antibodies raised against p85 proteins precipitates an 85 kD protein together with a second protein of molecular weight 110 kD (Otsu, M et al., 1991).

PI3-kinase is one of a growing number of potential signalling proteins which associate with protein-tyrosine kinases activated either by ligand stimulation or as a consequence of cell transformation. A common feature of all these proteins (apart from Raf), is that they contain one or more SH2 domains (src homology) (Koch, C A et al., 1991). Both p85α and p85β proteins contain two SH2 domains. Experiments from a number of laboratories have suggested that these domains may function by binding to peptide sequences usually phosphorylated on tyrosine residues, and thus mediate the complex formation which follows activation of protein-tyrosine kinases (Anderson et al, 1990; Meyer & Hanafusa, 1990; Moran et al, 1990; Matsuda et al, 1991; Meyer et al, 1991; reviewed in Koch, C A et al., 1991). In support of this, several studies suggest that tyrosine phosphorylation of the PDGF receptor or polyoma mT is essential for its association with proteins such as the PI3-kinase (Kazlauskas, A et al., 1989; Talmage, D A et al., 1989) GAP (Kaplan et al, 1990; Kazlauskas, A et al., 1990) and PLCγ (Anderson et al, 1990; Margolis et al, 1990). The precise tyrosine residue required for binding of the PI3-kinase activity (and an 85 kD phosphoprotein) to the human PDGF receptor has been mapped to tyrosine 751 which lies within the kinase insert region of the protein-tyrosine kinase domain (Kazlauskas & Cooper, 1989, 1990; Kazlauskas et al, 1991). The binding sites for other proteins to this receptor (eg., PLCγ, GAP and src-family kinases) have yet to be mapped, but these proteins may associate via other phosphorylated tyrosine residues.

This invention has been facilitated by the finding that certain synthesized peptides from the human PDGF β-receptor, namely peptides derived from the sequence around tyrosine 751 of the PDGF receptor, can be used to bind and isolate bovine brain PI3-kinase, making it possible to purify further partially purified bovine brain PI3-kinase (as described by Morgan et al, 1990) to apparent homogeneity and to obtain reasonably pure p110 protein. As will be described hereinafter, the PI3-kinase requires a phosphopeptide column containing a YXXM motif for its isolation by such a technique, the tyrosine being phosphorylated. Only if a column of this type is used are both the 85 kD and 110 kD proteins secured whereas 85 kD subunit binds to all phosphopeptide affinity columns tested and only fails to bind to non-phosphorylated peptides. Moreover, the relatively small size of the phosphopeptides used for such columns gives good specificity and a high density of affinity groups per unit volume of column.

This purification has allowed amino acid sequence information to be provided, and cDNA cloning to be performed. Such cloning has revealed some interesting facts. Thus, p110 is a 1068 amino acid protein having an unexpectedly high (compared to SDS-PAGE Figures) calculated molecular weight of about 124 kD (124247). The protein is related to Vps34p, a Saccharomyces cerevisiae protein involved in the sorting of proteins to the vacuole. Surprisingly, p110 when expressed in COS-1 cells was inactive and activity was only seen when complexed with p85. However, when expressed in insect cells, p110 could be shown to possess intrinsic kinase activity. The novel p100 polypeptide can be associated with p85α into an active p85α/p110 complex which binds the activated colony stimulating factor-1 receptor. The invention is also based upon these discoveries and unpredictable findings.

Thus, in one aspect the present invention provides an isolated polypeptide of calculated molecular weight approximately 124 kD which possesses PI3-kinase activity when produced by recombinant production in insect cells, or a polypeptide derivable therefrom which has PI3-kinase activity and binds, when associated with a p85 mammalian PI3 kinase subunit, to a phosphopeptide which includes the YXXM motif, the tyrosine being phosphorylated. Such polypeptides are preferably those capable of association with p85 subunits of mammalian PI3-kinases to produce active p85/p110 complexes. Preferably, the polypeptides have either the amino acid sequence of FIG. 9 hereof or exhibit significant sequence homology therewith. Preferred are polypeptides having at least amino acids 272 to 1068 of the seqeunce of FIG. 9 hereof.

As used herein, the term "PI3-kinase activity" means phosphoinositide-3 kinase activity.

The invention embraces polypeptides as defined and exhibiting sequence homology with any chosen mammalian species of PI3-kinase. A human sequence is given in FIG. 16 hereof. Amino acids 37(tyr)-834 (stop codon) (see FIG. 16) are >99% conserved with the bovine p110 CDNA sequence and correspond to amino acids 272–1069 (stop codon) of the sequence of FIG. 9. Upstream of amino acid 37 (human sequence) there is no sequence similarity between the p110 cDNA sequences from the two species.

The invention includes antibodies, monoclonal or otherwise, against the polypeptides of the invention.

In another aspect the invention includes a DNA sequence comprising either: (a) a sequence set out in FIG. 9 hereof; (b) any one of the subsequences A to N of FIG. 9 hereof; (c) the sequence represented by bases 816 to 3204 of FIG. 9 hereof; (d) a sequence set out in FIG. 16 hereof; or (e) a DNA sequence hybridizable to (a), (b), (c) or (d); which sequence (a), (b), (c), (d) or (e) encodes a polypeptide which has PI3-kinase activity if expressed in insect cells or can complex with a p85 mammalian PI3-kinase subunit to produce such activity. Subsequences A to N, referred to above, are themselves part of the present invention.

Hybridization conditions which may be used to find active sequences include, but are not limited to, 1M NaCl/10×Denhardt's solution/50 mM Tri-HCl (pH 7.4)/10 mM EDTA/0.1% SDS/100 μg/ml denatured herring sperm DNA (Sigma) at 65° C. for 16 h, with the following washing conditions, i.e. 2×SSC/0.1% SDS, 42° C.→0.5×SSC/0.1% SDS, 50° C.→0.1×SSC/0.1% SDS, 65° C.→0.1×SSC/0.1% SDS, 68° C.

The invention further provides a DNA construct comprising a DNA sequence as defined above under the control of a control sequence and in proper reading frame in an expression vector.

The control sequence may include a regulatable promoter (e.g. Trp). Selected host cells which have been genetically altered to permit expression of the encoded polypeptide by the incorporation of such a construct are another aspect of the invention, and the invention also includes both a method of making such a polypeptide by cultivating such host cells and, of course, the resulting polypeptides.

In general, new polypeptides of the invention can be used to provide PI3-kinase activity, either directly or after complexing with a mammalian p85 subunit. Enzymatically active complexes involving the above-defined polypeptides are part of the invention.

The invention envisages a method of prophylaxis or therapy which involves the encouragement or discouragement of cell proliferation by the action of an agonist or antagonist, respectively, for the PI3-kinase activity of a polypeptide of the invention or complex including the same, wherein said cell proliferation is mediated through a cell surface receptor interactive with said activity. The present invention opens up for the first time, by providing pure sequenced active protein, the opportunity to screen (using standard techniques) for such agonists or antagonists.

Another aspect of the invention is a pharmaceutical or veterinary formulation comprising an agonist or antagonist as defined above formulated for pharmaceutical or veterinary use, respectively, optionally together with an acceptable diluent, carrier or excipient and/or in unit dosage form. Conventional pharmaceutical or veterinary practice may be employed to provide suitable formulations or compositions.

Thus, the formulations of this invention can be applied to parenteral administration, for example, intravenous, subcutaneous, intramuscular, intraorbital, ophthalmic, intraventricular, intracranial, intracapsular, intraspinal, intracisternal, intraperiotoneal, topical, intranasal, aerosol, scarification, and also oral, buccal, rectal or vaginal administration.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences". Formulations for parenteral administration may, for example, contain as excipients sterile water or saline, polyalkylene glycols such as polyethylene glycol, oils of vegetable origin, or hydrogenated naphthalenes. Biocompatible, biodegradable lactide polymers, lactide/glycolide copolymers, or polyoxyethylene-polyoxypropylene copolymers may be used to control the release of the present factors. Other potentially useful parenteral delievery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, lactose or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

The concentration of PI3-kinase agonist or antagonist in the formulations of the invention will vary depending upon a number of issues, including the dosage to be administered, and the route of administration.

In general terms, such agonists or antagonists may be provided in an aqueous physiological buffer solution containing about 0.1 to 10% w/v compound for parenteral administration. General dose ranges are from about 1 μg/kg to about 1 g/kg of body weight per day; a preferred dose range is from about 0.01 mg/kg to 100 mg/kg of body weight per day. The preferred dosage to be administered is likely to depend upon the type and extent of progression of the condition being addressed, the overall health of the patient, the make up of the formulation, and the route of administration.

The invention also includes the use of a polypeptide of the invention, or active complex containing the same, or an agonist or antagonist thereof in affecting the level of stimulation of platelets or neutrophils or in regulating blood glucose levels (the action of insulin may be mediated by PI3-kinase activity), and such use when employed for prophylactic or therapeutic purposes is envisaged.

The polypeptides of the invention (or complexes containing them) have a particular utility in the in vitro enzymatic production of 3-phosphorylated phosphoinositides eg PI(3)P, PI(3,4)P2, PI(3,4,5)P3). Such materials are of considerable biochemical interest, and are often very difficult to synthesize by conventional chemical techniques. This invention provides, for the first time, appreciable amounts of purified and reliable enzymatic activity for such in vitro synthesis.

In general, the first step in the purification and cloning upon which the invention is based involved partial purification of PI3-kinase from bovine brain as previously described (Morgan et al, 1990) and then further purification by affinity chromatography on an immobilised 17 amino acid phosphotyrosine peptide whose sequence is based on that surrounding tyrosine 751 of the human PDGF-β receptor. Following this final purification, p110 and p85 were eluted from the resin with SDS-containing buffers. The p85/p110 mixture was either digested directly with lysylendopeptidase, or p110 was further purified by SDS-agarose gel electrophoresis (see below) and digested following elution from the gel. Peptides were separated by reverse phase HPLC and sequenced using a modified Applied Biosystems 477A sequencer. Amino acid sequence analysis of 14 peptides (A to N, FIG. 9) generated 235 residues which could be assigned with certainty (see FIG. 9, attached).

It is important to note that the successful production of sequence information herein was dependent upon a novel SDS-agarose gel electrophoresis technique. Although, SDS-PAGE is widely used for high resolution protein separations, and is a method which resolves components primarily by their differences in molecular weight, as the polyacrylamide matrix is not readily disrupted, protein recovery following SDS-PAGE generally requires techniques involving electroelution from gel slices, electroblotting, or passive diffusion. Elution of proteins from polyacrylamide gels that have been previously stained using sensitive reagents (such as Coomassie Blue) is slow and recoveries are frequently low. Furthermore, these methods may concentrate impurities present in the polyacrylamide matrix and in the relatively large buffer volumes required for elution. Preparative SDS-PAGE systems using continuous flow collection have also been developed, but these frequently exhibit decreased resolution and low recoveries.

The novel method employed herein uses SDS-agarose gel electrophoresis (SDS-AGE) and allows a combination of the high resolving capacity of slab gel electrophoresis and the detection of proteins using sensitive stains with a rapid recovery technique that isolates proteins in high yield and in small volumes. The recovered protein is highly purified and in a form that can be either readily precipitated or digested directly in SDS containing buffers. Peptides produced by this method can be fractionated by HPLC and then analysed by automated amino acid sequencing. The recovery of long hydrophobic peptides is particularly efficient using these digestion conditions. The following protocol guides the skilled reader.

PROTOCOL

Materials

All chemicals should be of analytical or purer grades. Guanidinium hydrochloride was Aristar grade (BDH, UK). FMC Prosieve was purchased from Flowgen (UK) and ultrapure agarose was from BRL (USA). Other electrophoresis reagents were from Biorad (UK, Electrophoresis grade). Standard molecular weight proteins were from Bio-Rad (UK) and Amersham International (UK). Sequencing grade trypsin (porcine, EC 3.4.21.4) was from Boehringer Mannheim (UK) and lysylendopeptidase (Achromobacter lyticus, EC 3.4.21.50) was from Wako Chemicals GmbH (Germany). Glass capillaries were those supplied by Applied Biosystems Inc (USA) for use on the 430A HPEC system, but were frosted by abrasion with an aqueous carborundum suspension (C150 grade) and a steel rod. Frosted slab gel plates were obtained from Hoefer (UK).

Slab SDS-AGE

Slab Prosieve resolving gels of 0.75 or 1.5 mm thickness were poured essentially as described by the manufacturer using pairs of 16×18 cm glass plates, one of which was frosted in order to prevent the gel from slipping out of the electrophoresis assembly. It is important to ensure that the gel plates be thoroughly warmed to 60° C. prior to pouring the resolving gel. The inability to warm the gel plates prior to pouring an agarose stacking gel, the insertion of the comb into a rapidly cooling gel, and the removal of the comb from the fragile agarose stacking gel initially caused severe problems. In order to remove these difficulties a 5% T, 2.6% C polyacrylamide stacking gel was used in place of agarose in later preparations.

Samples were denatured at 100° C. in sample buffer (190 mM Tris/HCl, pH 6.8, 6% (w/v) SDS, 30% (v/v) glycerol, 10 mM DTT, 0.01% (w/v) bromophenol blue) and gels were run using Laemmli cathode buffer (0.192M glycine, 0.025M Tris, 0.1% (w/v) SDS) with a modified anode buffer (1M Tris/HCl, pH 8.3) at 200 v (approximately 50 mA for 1.5 mm and 25 mA for 0.75 mm gels) for about 4 h using a SE400 gel apparatus (Hoefer, USA). Gels were stained using either Coomassie Blue G-250 (Bio-Rad, UK) with rapid destaining or 4M ammonium acetate solution. In the latter case proteins were identified within a few minutes by optical contrast using incident light reflection observed against a dark background. Protein bands were immediately excised and gel slices stored at −20° C.

HPEC Electroelution

Gel slices were thawed and washed twice in 1 ml of 62.5 mM Tris/HCl, pH 6.8 for 5 min each at 20° C. Slices containing Coomassie Blue were prewashed with 1 ml of 50% (v/v) methanol, 5% (v/v) acetic acid for 5 min at 20° C.

The volume of the gel slice was estimated, then 10% SDS and 20% DTT were added to final concentrations of 2% and 0.2% (w/v) respectively. The gel slice was melted and homogenized by immersion in boiling water for 5 min with occasional mixing. The sample volume was then measured and made up to the required amount (see Table 1 below) with prewarmed 62.5 mM Tris/HCl, pH 6.8. The diluted sample was heated for a further 5 min and loaded into a prewarmed glass HPEC capillary. It was important not to exceed 90% of the capillary volume at this stage. The capillary was incubated at 4° C. for at least 10 min to allow the sample gel to solidify, before the slow addition of 0.8% agarose, 1M Tris/HCl, pH 8.8 to overfill the capillary. After a further 10 min at 4° C., the ends of the gel were trimmed flush, sealed with Zytex discs, and applied to an Applied Biosystems 230A HPEC system. Electroelution was performed using an elution buffer pressure of 2.5 psi (generating a flow rate of approximately 1 µl/min), an upper reservoir buffer pressure of 3.5 psi and a lower reservoir buffer pressure of 0.9 psi. These settings were changed from the manufacturer's recommendations in order to stop the gel from collapsing upwards during the run. The current settings were as described in the text and 3 min fractions were collected while monitoring the eluate at 280 nm. The fraction collector rack was cooled to 4° C. and the gel compartment was cooled to 10° C.

TABLE 1

HPEC Elution Gel Parameters

| Capillary size (mm) | | Gel volume (µl)[a] | | | |
| --- | --- | --- | --- | --- | --- |
| Length | i.d.[a] | Total | Sample | Focussing | Current (mA) |
| 50 | 2.5 | 245 | 220 | 25 | 1,0–1.5 |
| 50 | 3.5 | 480 | 432 | 48 | 1.5 |
| 100 | 2.5 | 491 | 441 | 49 | 2.0–2.5 |
| 100 | 3.5 | 960 | 864 | 96 | 2.5 |

[a]These values are underestimated due to the variable increase in the internal diameter of the capillaries caused by the frosting procedure.

Preparation of Proteins for Sequence Analysis

Fractions were assayed for protein content and purity either by monitoring radioactivity or by SDS-PAGE and silver staining. Samples required for trypsin or lysylendopeptidase digestion and subsequence sequence analysis were separated from Coomassie Blue by sequential precipitation on ice using 10% (w/v) TCA and then 20% TCA with centrifugation for 10 min at 4° C. Pellets were washed with 1 ml of acetone at −20° C. overnight and then washed again briefly in order to remove trace contamination by TCA and SDS before air drying and the addition of the required digestion buffer. Tryptic digestions were performed in 0.1M Tris/HCl, pH 8.0 at 37° C. and lyslendopeptidase digestions in 20 mM Tris/HCl, pH 8.8 containing 0.1% (w/v) SDS at 30° C. Solid guanidinium hydrochloride was added to tryptic digests (6M final concentration) and incubated for 1 h at 37° C. Products were applied directly to HPLC columns using a Hewlett-Packard 1090M system and the effluent was monitored with a 79880A diode array detector. Trypsin digests were fractionated using an Applied Biosystems RP-300 column (2.1×100 mm) while lysylendopeptidase products required an Applied Biosystems AX-300 (2.1×30 mm) and an OD-300 column (2.1×100 mm) connected in series essentially as described by Kawasaki and Suzuki (1990).

The following Examples are given to illustrate the present invention without limiting the same. The Examples refer to the accompanying drawings.

In the accompanying drawings:

FIGS. 1 to 9 are concerned with Example 1, sections A and B.

FIGS. 1A–1D. Phosphorylation and purification of Y751 phosphopeptide.

Panel A. HPLC profile for separation of the phosphorylated from the non-phosphorylated Y751 peptide on a $C_{18}$ reverse phase column. The trace shows the spectra monitored at 214 nm during the course of the elution. The peaks corresponding to the phosphorylated and non-phosphorylated peptide are indicated by arrows. The small peaks observed are derived from the A431 membranes.

Panel B. Spectral analysis of the purified phosphorylated and non-phosphorylated Y751 peptides between 240 and 300 nm as measured by the diode-array detector. The absorption maximum for the peptide is observed to shift to a lower wavelength following tyrosine phosphorylation.

Panels C & D. Phosphoamino acid analysis of Y751 peptide phosphorylated by either purified EGF receptor (left panel) or A431 cell membranes (right panel). Following the phosphorylation reaction the phosphopeptide was purified by reverse phase HPLC. The peptide was subjected to acid hydrolysis and the phosphoamino acids separated by two-dimensional thin layer electrophoresis. Internal standards were stained with ninhydrin and the $^{32}$P-labelled phosphoamino acids were detected by autoradiography. The positions of inorganic phosphate ($P_i$), and phosphoserine (S), phosphothreonine (T) and phosphotyrosine (Y) standards are indicated.

FIG. 2. Purification of PI 3-kinase complex on the Y751 phosphopeptide affinity column.

Panel A. Peak 1 (P1) and peak 2 (P2) of PI 3-kinase fractions from the second MonoQ step were analysed on a 7.5% SDS-PAGE gel. Proteins in these two peak fractions were visualised by silver staining. The migration positions of molecular weight markers are indicated.

Panel B. Affinity purification of peak 1 (P1) and peak 2 (P2) PI 3-kinase using the Y751 phosphopeptide column. Silver stain of a 7.5% SDS-PAGE gel showing PI 3-kinase associated proteins from MonoQ P1 and P2 which bound to, and were eluted from, the Y751 phosphopeptide column with 0.1% SDS-containing phosphate buffer at 80° C. Lanes 1, 2 and 3 for both the P1 and P2 material indicates the proteins eluted by successive 50 µl elutions.

Figure 3:
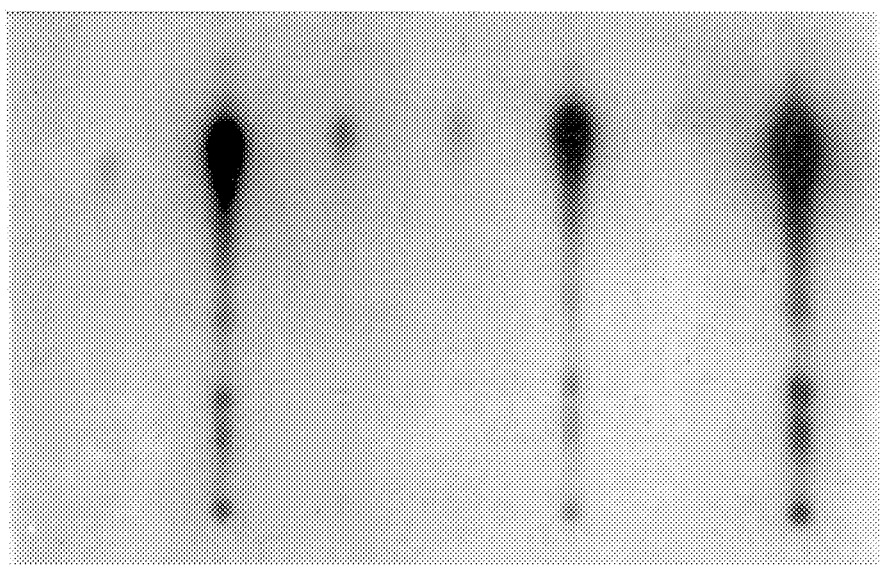
Figure 4A:
Figure 4B:
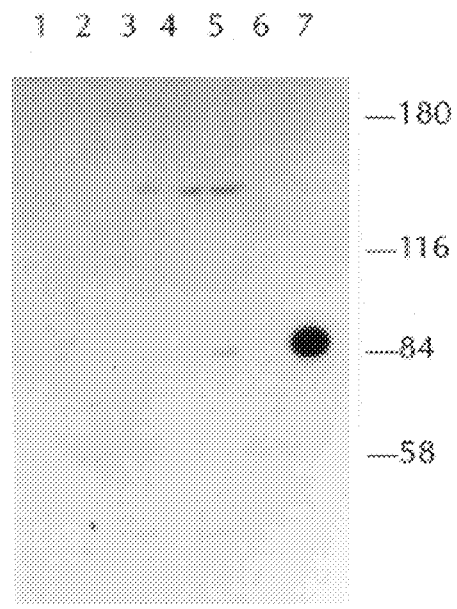
Figure 4C:
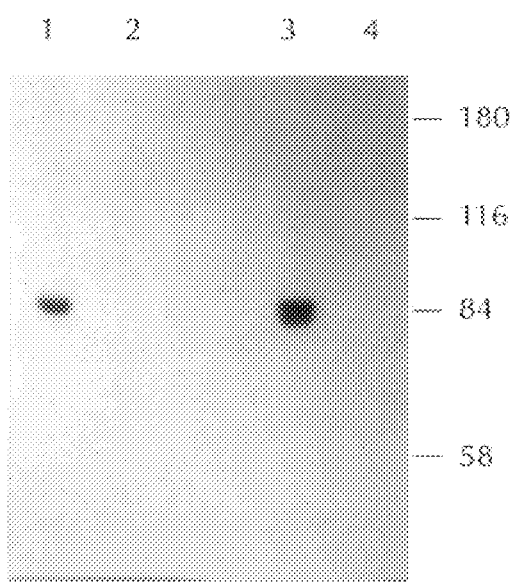
Figure 4D:
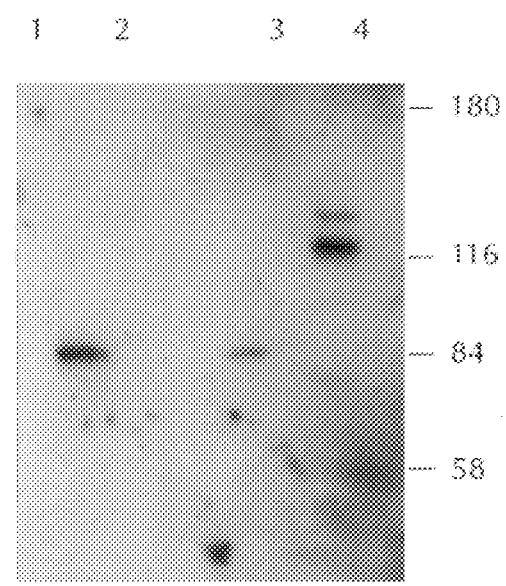

FIG. 3. Characterisation of the binding of PI 3-kinase activity to Y751 derived peptide columns.

One microgram of partially purified peak 1 bovine brain PI 3-kinase was applied to 10 µl of the Y751 derived peptide resins in 100 µl of binding buffer. Bound proteins were assayed for PI 3-kinase activity. Lane 1, PI 3-kinase activity bound to non-phosphorylated Y751 column. Lane 2, PI 3-kinase activity bound to phosphorylated Y751 column. Lane 3, PI 3-kinase activity removed from supernatant of column in lane 2 by fresh phosphorylated Y751 column. Lane 4, PI 3-kinase activity remaining associated with the column from lane 2 following removal of the bound material using 0.1% SDS at 80° C. Lane 5, PI 3-kinase activity bound to recycled phosphorylated Y751 column as used in lane 2 following addition of a fresh aliquot of bovine brain PI 3-kinase in binding buffer. Lane 6, Equivalent amount of peak 1 soluble bovine brain PI 3-kinase activity as applied to columns in lane 2 or lane 5.

FIG. 4. Identify of p85 species in peak 1 and 2 of bovine brain PI 3-kinase preparation.

Protein samples were separated on 7.5% SDS-PAGE gels and transferred to nitrocellulose. The blots were then probed with antisera raised against the COOH-terminal peptide sequences of p85α or p85β.

Panel A. Western blot probed with anti-p85α COOH-terminal antisera.

Lane 1, peak 1 bovine brain PI 3-kinase; lane 2, peak 2 bovine brain PI 3-kinase; lane 3, Cos-1 cell lysate from pMT2 vector alone transfected cells; lane 4, Cos-1 cell lysate from pMT2p85α transfected cells; lane 5, Cos-1 cell lysate from pMT2p85β transfected cells; lane 6 Sf9 cell lysate containing p85α; lane 7, Sf9 cell lysate containing p85β Panel B. Western blot probed with anti-p85β COOH-terminal antisera.

Lanes are as described for panel A.

Panel C. Competition of peptides with antibodies in Western blots. Samples in lanes 1 and 2 were probed with p85α specific antiserum while samples in lanes 3 and 4 were probed with the p85β specific antiserum. Lanes 1 and 2. Sf9 cell lysate containing baculovirus expressed p85α. Lanes 3 and 4, Sf9 cell lysate containing baculovirus expressed p85β. In the odd numbered lanes the nitrocellulose was probed with specific antiserum alone. In the even numbered lanes the antiserum was competed with 100 μg/ml of p85α (lane 2) and p85β (lane 4) specific C-terminal peptides respectively.

Panel D. Anti p85α western blot of bound and soluble PI 3-kinase material after chromatography using the Y751 phosphopeptide column.

Peak 1 (P1) and peak 2 (P2) of bovine brain PI 3-kinase were immobilised on the Y751 phosphopeptide column. Material which did not bind was collected and then the resin was washed extensively. Bound proteins were eluted from the column with SDS-PAGE sample buffer. Bound and unbound proteins were separated by SDS-PAGE on a 7.5% gel and then transferred to nitrocellulose. The filter was then probed with anti-p85α COOH-terminal antisera and visualised with $^{125}$I Protein A-Sepharose. Lane 1, P1 bound material; Lane 2, peak 1 material which did not bind to column; Lane 3, peak 2 bound material; Lane 4, peak 2 material which did not bind to column.

Figure 5A:
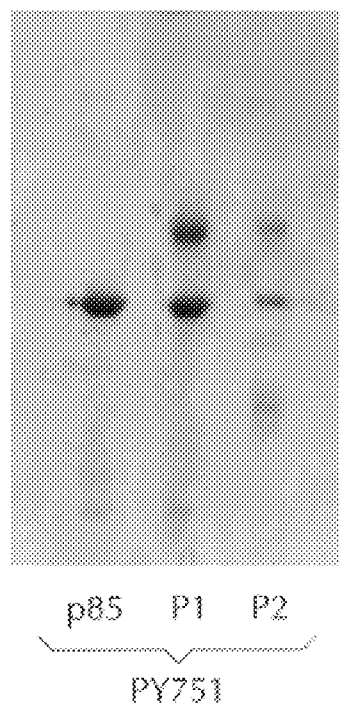
Figure 5B:
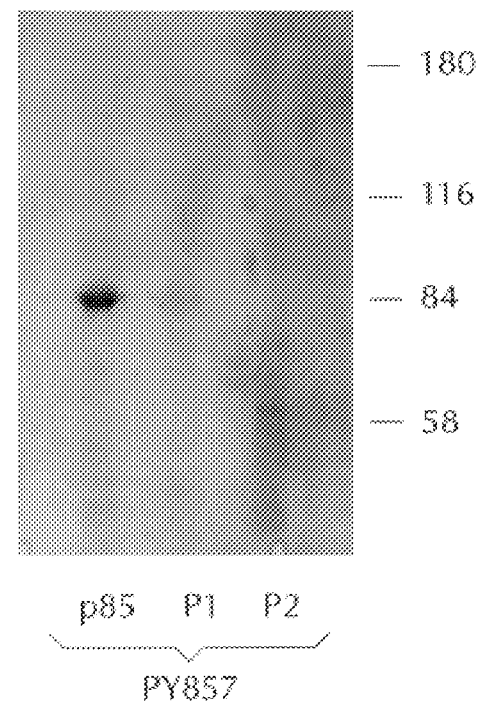

FIG. 5. Specificity of binding of PI 3-kinase complex to Y751 peptide column:-comparison with Y857 phosphopeptides.

Sf9 cell lysates containing p85α proteins or one microgram of partially purified bovine brain PI 3-kinase (P1 and P2 MonoQ) was allowed to bind to the columns for 4 h at 4° C. as described. The columns were then washed repeatedly with binding buffer, bound proteins were eluted with SDS-containing buffers and then analysed by electrophoresis on 7.5% SDS-PAGE gels. Bound proteins were visualised by silver staining. Panel A. Proteins bound to Y751 phosphopeptide column. Panel B. Proteins bound to Y857 phosphopeptide column. The migration position of molecular weight markers are indicated.

Figure 6A:
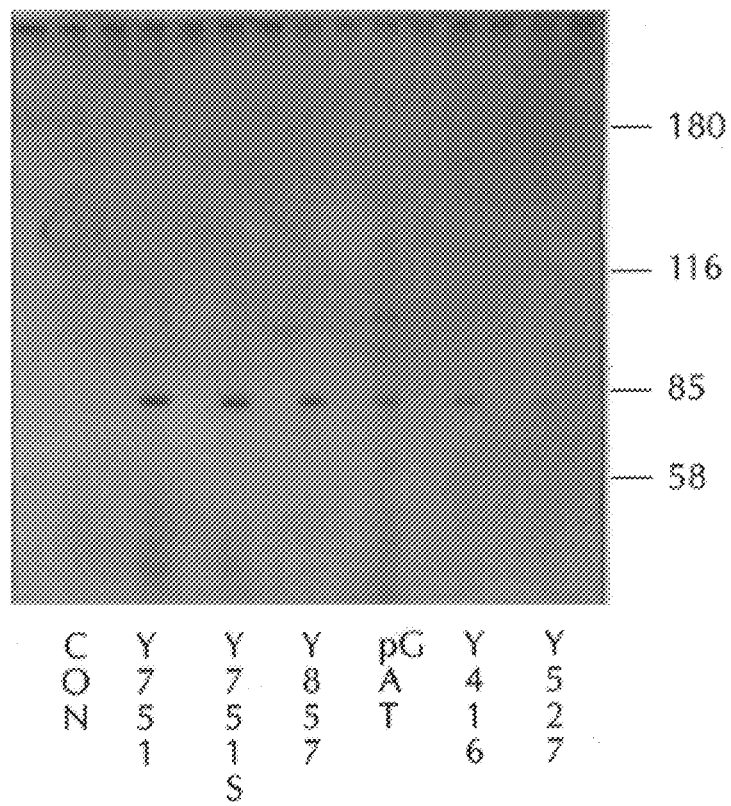
Figure 6B:
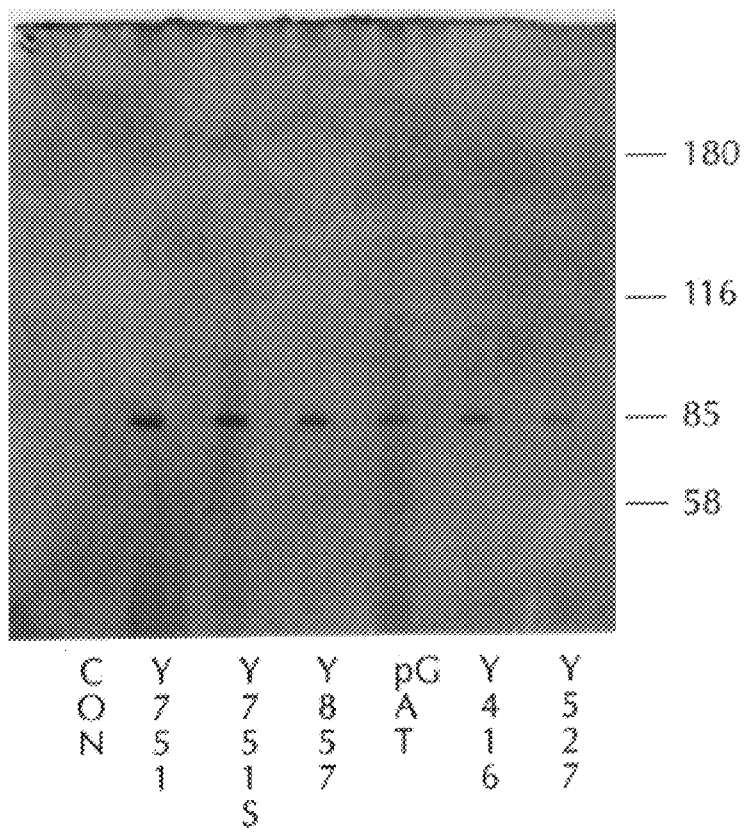

FIG. 6. Binding of recombinant baculovirus expressed p85 proteins to a panel of phosphopeptide columns.

P85 proteins in SF9 cell lysates were tested for their ability to bind to the various peptide column. After extensive washing, bound proteins were eluted from the columns, separated on 7.5% SDS-PAGE gels and the visualised by staining with Coomassie Blue. Panel A. Bound p85α. Panel B. Bound p85β. CON, 17 amino acid non-phosphorylated Y751 column; Y751, 17 amino acid phosphopeptide from the kinase insert region of the PDGF β-receptor; Y751.S, 11 amino acid version of Y751 phosphopeptide; Y857, 17 amino acid phosphopeptide derived from the sequence around the second major tyrosine phosphorylation site in the PDGF β-receptor; pGAT, poly Glu:Ala:Tyr phosphopeptide; Y416 and Y527, 13 and 16 amino acid phosphopeptides derived respectively from the two major tyrosine phosphorylation sites of pp60$^{c-src}$.

Figure 7A:
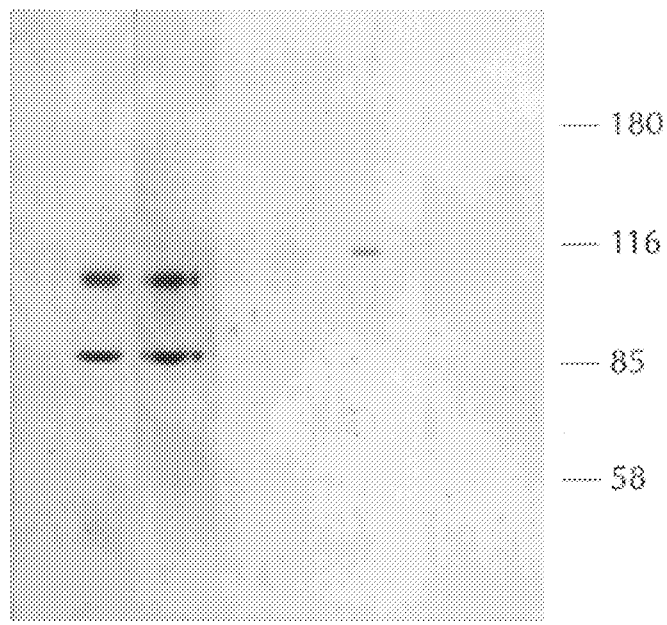
Figure 7B:
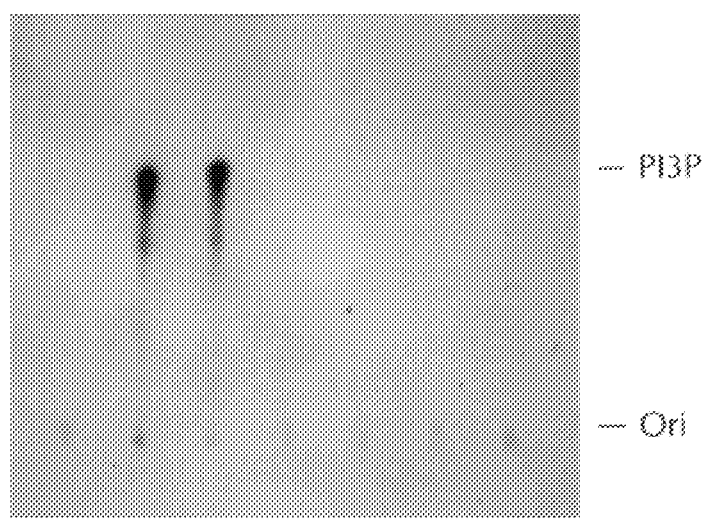

FIGS. 7A and 7B. The p85/100 complex and PI 3-kinase activity show specificity in the range of phosphopeptides to which they will bind.

One microgram of partially purified bovine brain PI 3-kinase (P1 MonoQ) was allowed to bind to peptide affinity columns for 4 h at 4° C. as described. The columns were then washed repeatedly with binding buffer. Bound proteins were then either eluted with SDS-containing buffers and then analysed by electrophoresis on 7.5% SDS-PAGE gels or assayed for PI 3-kinase activity bound to the column.

Panel A. Bound proteins were visualised by silver staining. The migration of molecular weight markers is indicated.

Panel B. PI 3-kinase activity bound to various phosphopeptide columns. The $^{32}$P-labelled lipid products were separated by TLC and the visualised by autoradiography. PI3P indicates the migration position of a P13P standard. Ori indicates the origin of the TLC plate.

Figures 8A, 8B:
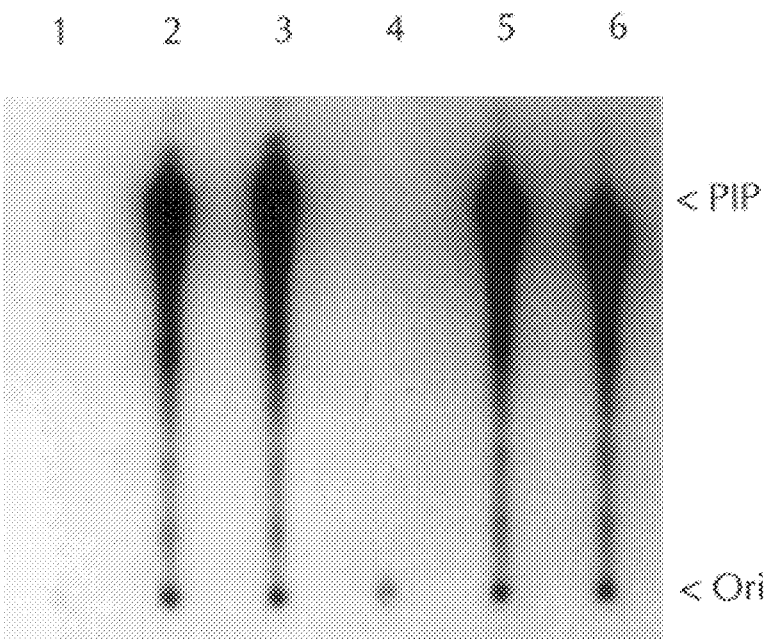

FIG. 8. Binding of PI 3-kinase activity of phosphopeptides containing the YXXM motif.

Panel A. One microgram of partially purified peak 1 bovine brain PI 3-kinase was bound to 10 μl of the indicated peptide columns. Following extensive washing the columns were assayed for bound PI 3-kinase activity. Lane 1, PI 3-kinase activity bound to non-phosphorylated Y751 column; Lane 2, PI 3-kinase activity bound to phosphorylated Y751 column; Lane 3, PI 3-kinase activity bound to phosphorylated Y751.S column; Lane 4 PI 3-kinase activity bound to phosphorylated Y857 column; Lane 5, PI 3-kinase activity bound to phosphorylated Y740 column;

Lane 6, PI 3-kinase activity bound to phosphorylated Met Y1313 column. PIP indicates the migration position of a P14P standard. Ori indicates the origin of the TLC plate.

Panel B. Comparison of identified PI 3-kinase binding sites in the peptides tested. The proposed consensus sequence for binding is also shown for comparison (Cantley et al., 1991).

FIGS. 9 to 15 are concerned with Example 1, sections C and D, and FIGS. 16 to 25 relate to Example 2.

Figure 9I:
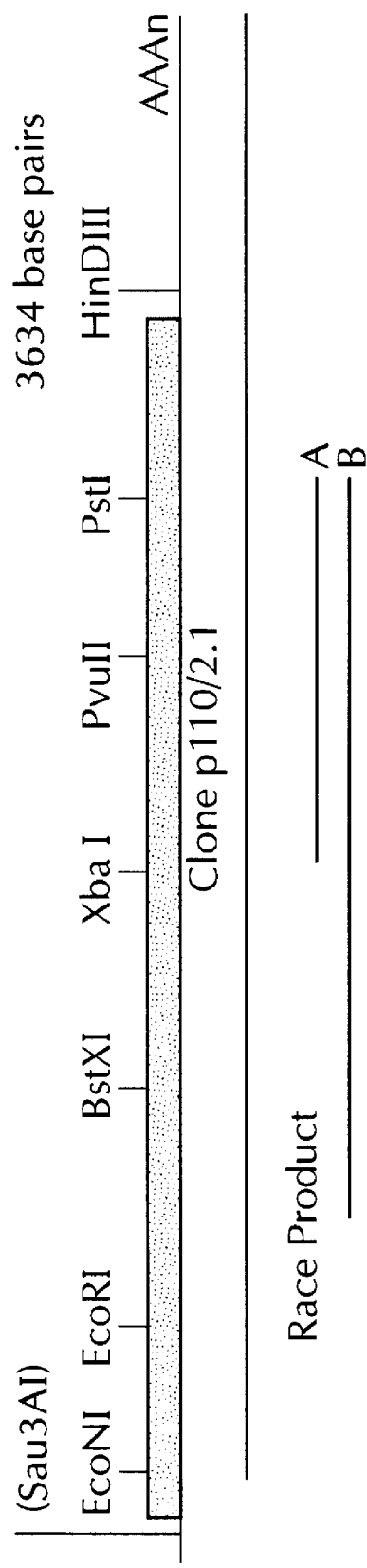

FIG. 9. Nucleotide Sequence and Deduced Amino Acid Sequence of p110.

(Top Panel) The nucleotide sequence of the coding region and the deduced amino acid sequence in one letter code are shown. Peptide sequences (lettered from A-N) obtained by protein sequencing are highlighted.

(Lower Panel) Schematic representation of the p110 cDNA. The bold line indicates coding sequence. (p2.1): extent of clone p2.1, (Race Product): region amplified by RACE PCR, (a): probe used in Southern blot analysis, (b): probe used in northern blot analysis, (S): Sau3AI site changed to BamHI site for expression in Sf9 cells.

Figure 10A:
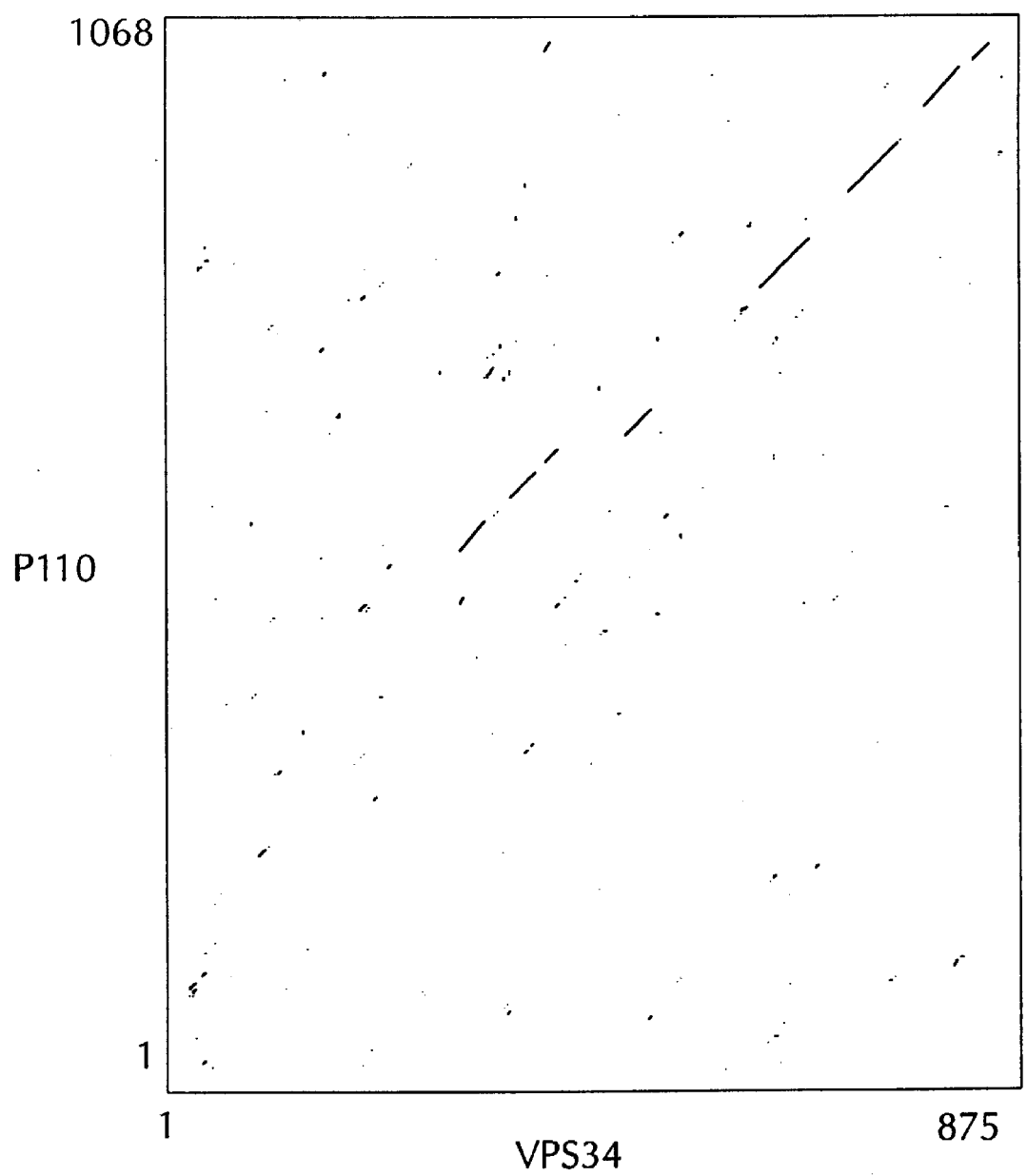
Figure 11A:
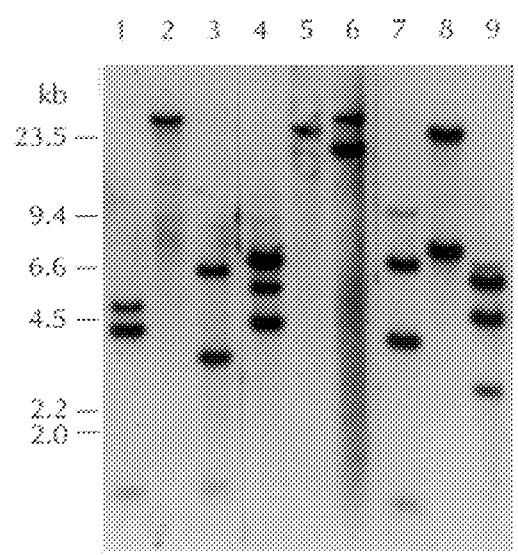
Figure 11B:
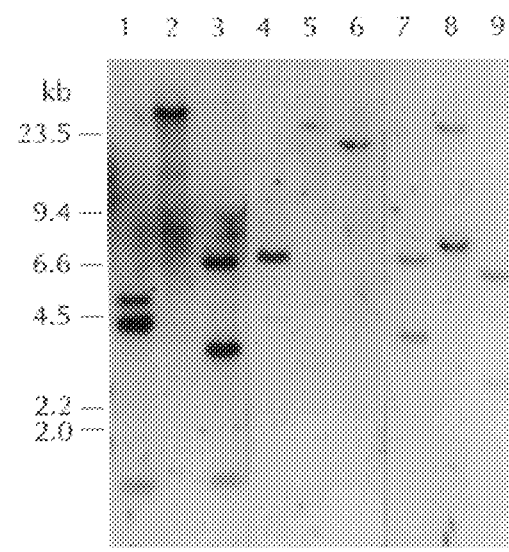

FIGS. 10A–10B. Comparison of p110 and Vps34p Protein Sequences (A) Dot plot comparison of Vps34p (875 amino acids: horizontal axis) and p110 (1068 amino acids: vertical axis) using the Compare program (UWGCG package; Devereux et al., 1984).

(B) The optimal alignment of p110 (upper sequence) and Vps34p (lower sequence) over the region of homology, using the Gap program (UWGCG package: Devereux et al., 1984). Identical residues are indicated by (I), conserved residues are indicated by (:). Residues proposed to be involved in ATP binding are marked with (*).

FIG. 11. Genomic Southern Analysis of p110

High molecular weight DNAs (3 μg) of bovine (lanes 1, 2, 3), human (lanes 4, 5, 6) and rat (lanes 7, 8, 9) origin were digested with EcoRI (lanes 1, 4, 7), BamHI (lanes 2, 5, 8) of HindIII (lanes 3, 6, 9), fractionated through a 0.5% agarose gel and transferred to a nitrocellulose membrane as described in Example 1. The filter was probed with a $^{32}$P-labelled XbaI-PstI fragment (probe a in FIG. 9, lower panel). The filter was washed in 0.5×SSC, 0.1% SDS at 50° C. and exposed overnight (Panel A). The filter was then washed in 0.1×SSC, 0.1% SDS at 68° C. and exposed for seven days (Panel B). The marker track shows the positions of lambda HindIII markers.

FIG. 12. Analysis of Tissue Distribution of p110 Message (A) Northern Blot Analysis of p110 5 µg of poly(A)$^+$RNA isolated from total bovine brain (lane 1) or the SGBAF-1 cell line (lane 2) were fractionated on a 0.9% agarose gel and immobilised on membranes as described in Example 1. The filter was probed with a $^{32}$p labelled antisense RNA probe (probe b in FIG. 9, lower panel). After washing in 0.1×SSC, 0.1% SDS at 60° C., the filter was treated with 1 µg ml$^{-1}$ RNAase A and autoradiographed overnight.

(B) PCR Analysis to Detect p110 Transcripts Poly(A)$^+$ RNA was isolated from various sources and PCR performed as described in Example 1. Bands of 218 bp and 212 bp indicate the specific amplification of human and bovine transcripts, respectively. Lane 1; Human T-cell blasts, lane 2; Human peripheral blood acute lymphocytic leukaemia cells, lane 3; A431 cells (Human), lane 4; COS-1 cells (Simian), lane 5; bovine brain, lane 6; SGBAF-1 cells (Bovine), lane 7; ZNR cells (Porcine).

(C) PCR Analysis to Detect p85α Transcripts Poly (A)$^+$ RNA was isolated from various sources and PCR performed. Specific amplification of p85α message gives a bind of 190 bp. Lanes are the same as indicated for (B).

FIG. 13. Expression of p85α and p110 in Sf9 Cells Using Baculovirus Vectors (A) Sf9 cells were infected with a wild type baculovirus (lanes 1 and 2) or with baculoviruses expressing p85α (lane 3), p110 (lane 4) or p85α and p110 (lanes 5 and 6). Immunoprecipitates were prepared with either anti-p85α (lanes 1, 3, and 5) or anti-p110 antisera (lanes 2, 4 and 6), samples fractionated on a 7.5% SDS-PAGE gel and visualised by staining with Coomassie blue.

(B) PI3-kinase assays were performed on Immmunoprecipitates of p85α and p110 expressed in Sf9 cells. lanes 1–6 the same as Panel (A); lane 7: pI3-kinase activity from 1 µl of the partially purified bovine brain PI3-kinase preparation.

FIG. 14. In Vitro Association of PI3-Kinase Activity with the CSF-1 Receptor

An in vitro PI3-kinase assay was performed on anti-CSF-1 receptor immunocomplexes prepared from Sf9 cells infected with a baculovirus expressing the CSF-1 receptor and treated as follows; lane 1: anti-CSF-1 receptor immunoprecipitates, untreated; lane 2; anti-CSF receptor immunoprecipitate, pre-treated with ATP and incubated with a p85α/p110 containing Sf9 cell lysate; lane 3: anti-CSF-1 receptor immunoprecipitate, treated in the absence of ATP and incubated with a p85α/p110 containing Sf9 cell lysate; lane 4: anti-CSF-l receptor immunoprecipitate, pre-treated with ATP and incubated with a p85α containing Sf9 cell lysate; lane 5; anti-CSF-1 receptor immunoprecipitate, pre-treated with ATP and incubated with a p110 containing Sf9 cell lysate.

FIG. 15. Expression of p85α and p110 in COS-1 Cells

COS-1 cells were transfected with 5 µg of the respective DNAs and harvested 48 h later. Transfected cells were labelled with 100 µCi ml-$^{1}$ of $^{35}$S-methionine for the last 4 h of this period. Immunoprecipitations were performed with either an p85α polyclonal antiserum or a p110 C-terminal peptide antiserum. After washing, the pellet was divided in two and half was then analyses on a 10% SDS-PAGE gel while the other half was subjected to P13-kinase assay.

(A) $^{35}$S-labelled proteins immunoprecipitated with anti-p85α antiserum.

(B) PI3-kinase activity immunoprecipitated with anti-p85α antiserum.

(C) $^{35}$S-labelled proteins immunoprecipitated with 110 C-terminal peptide antiserum.

(D) p13-kinase activity immunoprecipitated with 110 C-terminal peptide antiserum.

Lanes contain results from COS-1 cells transfected with the following DNAs; lane 1: vector DNA, lane 2: pMT2-p85α, lane 3: pSG5-p110, lane 4: pMT2-p85α and pSG5-110, lane 5 in panels B and D show the PI3-kinase activity immunoprecipitated with the two antisera from 1 µl of the partially purified bovine brain p13-kinase preparation. The exposure times for panels A and C, and B and D are identical.

FIG. 16. CDNA for human p110

The figure shows the sequence of human p110 cDNA, together with the corresponding amino acid sequence.

FIG. 17. A comparison of the human p110 sequence and bovine p110 sequence at the DNA level.

FIG. 18. A comparison of the human p110 sequence and bovine p110 sequence at the protein level.

FIG. 19. The protein sequence of human p110.

FIG. 20. The sequence of a CDNA related to p110, PITR-c.

FIG. 21. The sequence of a cDNA related to p110, PITR-f.

FIG. 22. The alignment of human p110, PITR-c, PITR-f and the yeast PI3-kinase VPS34.

Figure 23A:
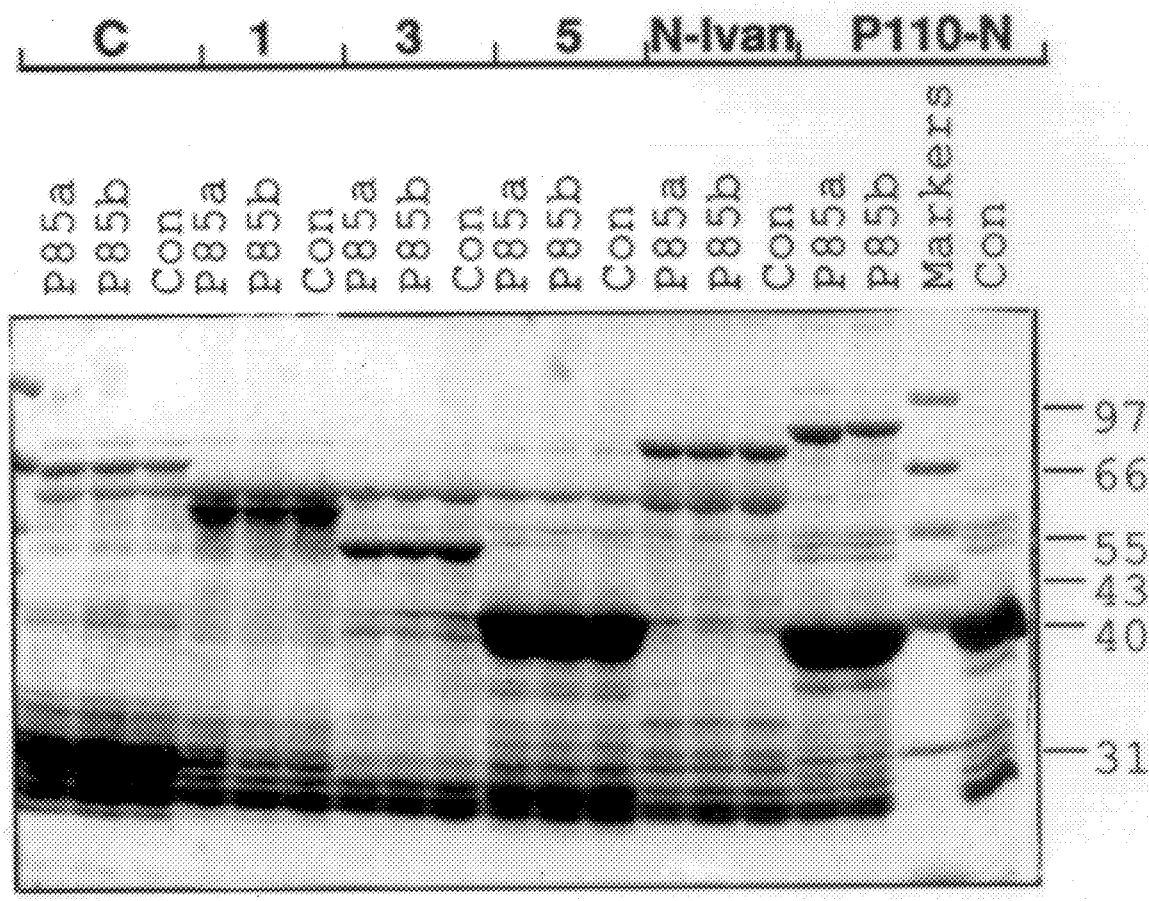

FIG. 23A. SDS PAGE analysis of proteins able to bind to various domains of human p110.

Figure 23B:
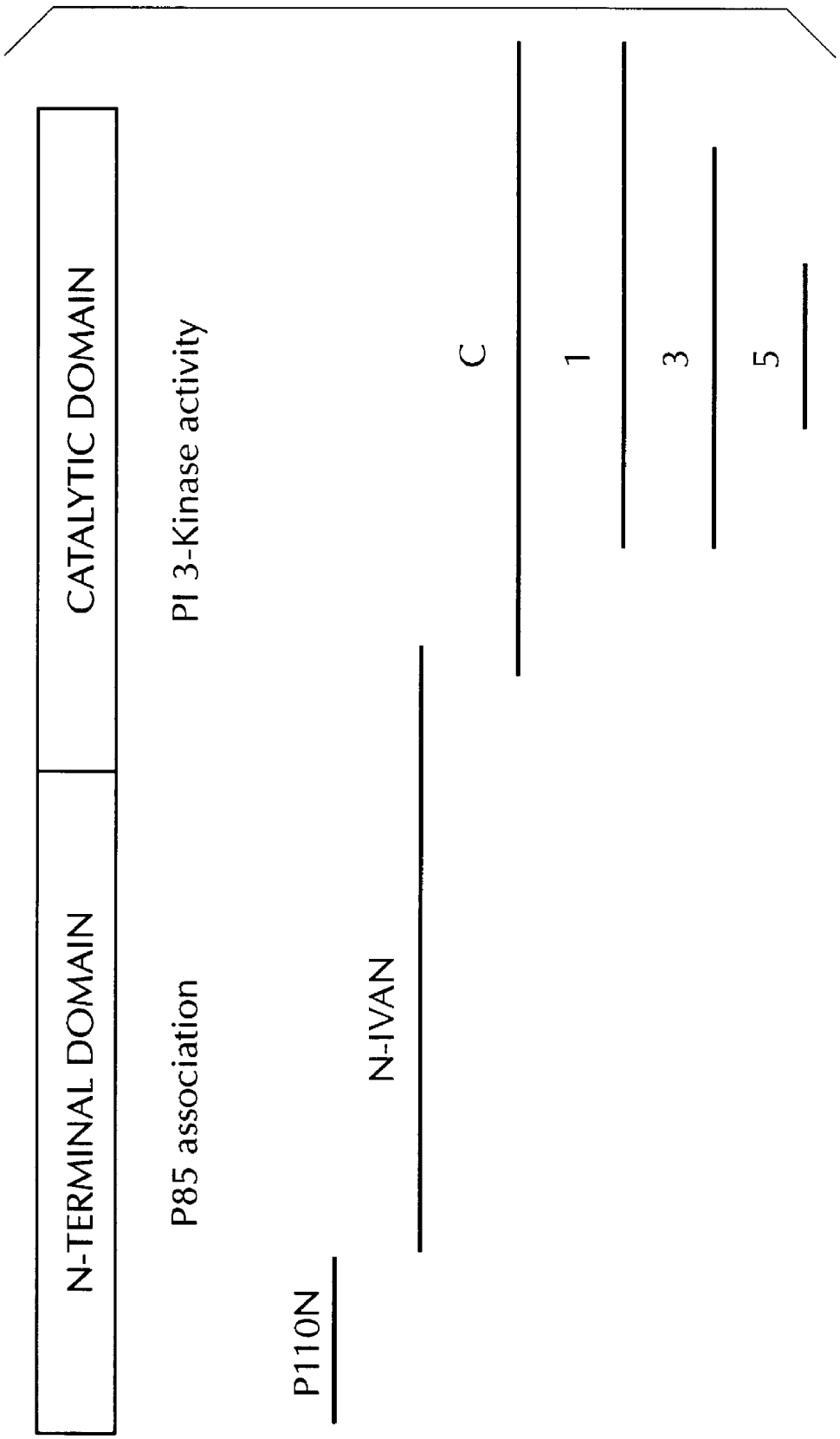

FIG. 23B. Schematic representation of the domains of p110 analysed for their ability to bind p85.

Figure 24:
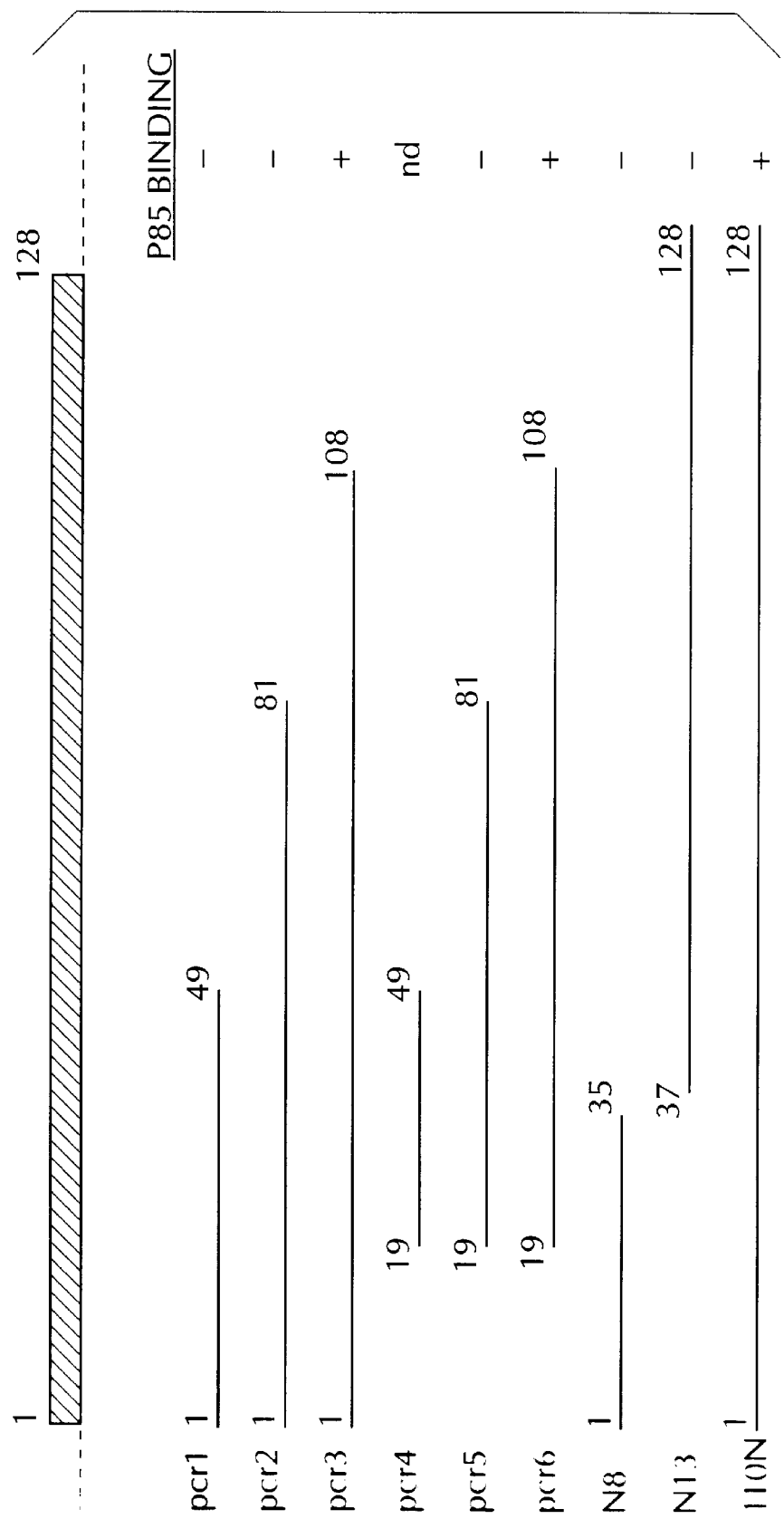

FIG. 24. Various deletion mutants and PCR fragments of p110 fragment p110-N.

Figure 25A:
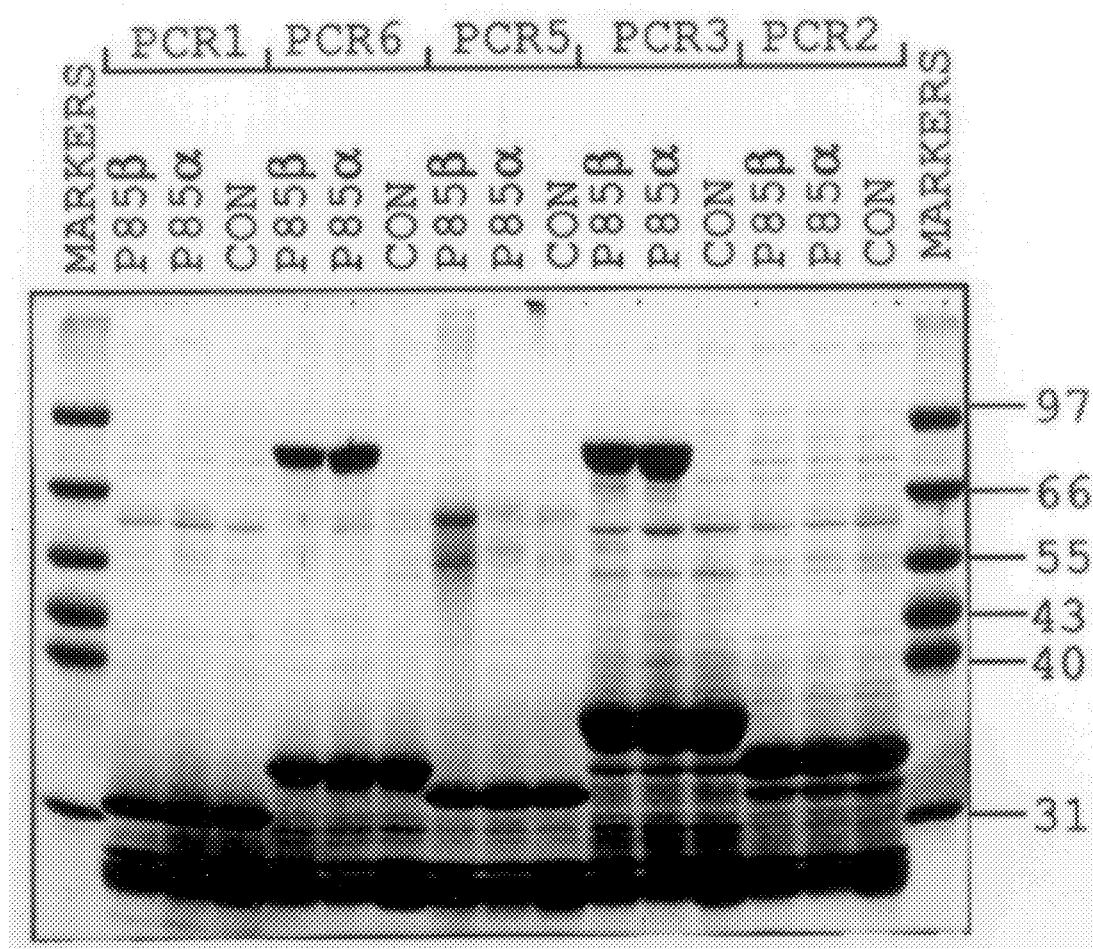
Figure 25B:
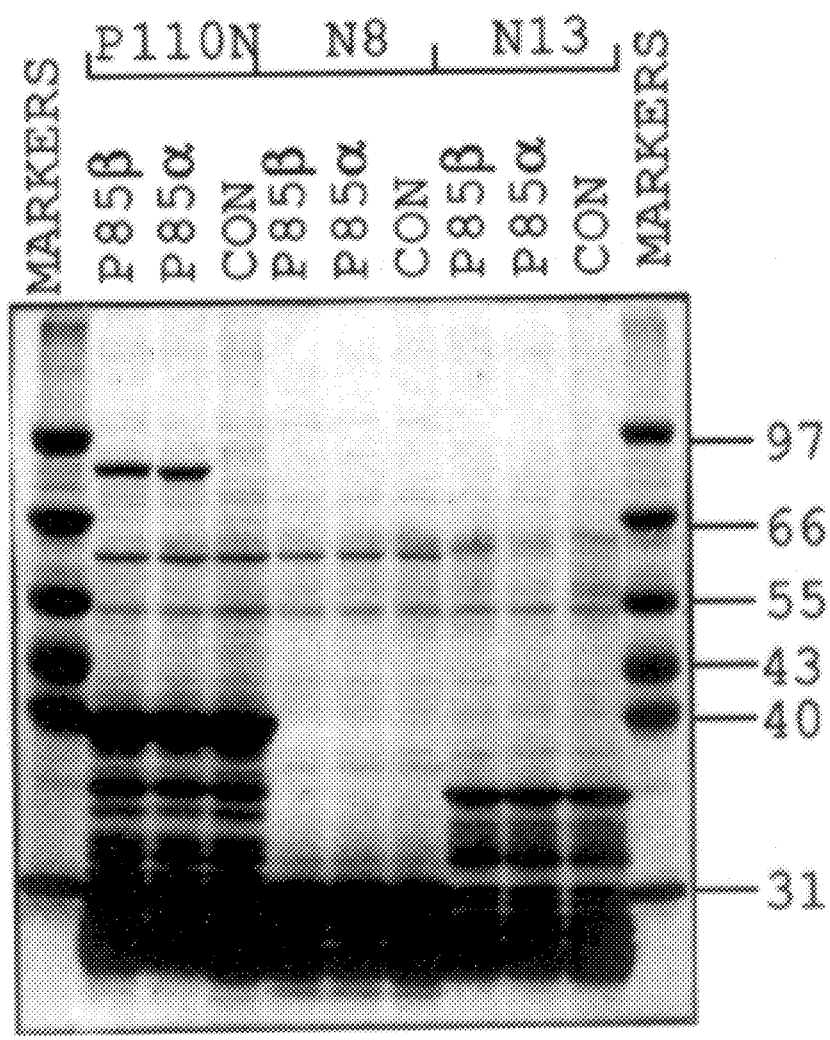

FIGS. 25A and 25B. The ability of the various deletion mutants and PCR fragments of p110-N to bind the p85 subunits.

EXAMPLE 1

Protein Purification

A. Methods and Materials

Cells

A431 cells were maintained in Dulbecco's modified Eagle's medium containing 10% foetal calf serum. Maintenance of insect cell culture and infection of Spodoptera frugiperda (Sf9) cells were carried out as described in Summers and Smith (1987).

Preparation of A431 Membranes

This preparation was modified from that described by Thom et al (1977). Harvesting solution (0.05M boric acid (pH 7.2), 0.15M NaCl), extraction solution (0.02M boric acid (pH 10.2), 0.2 mM EDTA) and borate solution 0.5M Boric acid (pH 10.2) were all prepared fresh. Cells were washed once with ice-cold harvesting solution and then scraped into fresh harvesting solution. Cells were pelleted by low speed centrifugation at 200 g, and then resuspended by pipetting in 2 pellet volumes of harvesting solution. This was added slowly, with stirring, to 100 pellet volumes of extraction solution. After 10 min, 8 pellet volumes of borate solution was added and stirring continued for a further 5 min. This solution was filtered through nylon gauze (Av. mesh size 900 µm), and spun at 500 g for 10 min at 2° C. to pellet any nuclei/whole cells. Finally, the supernatant was centrifuged at 12,000 g in a ultracentrifuge SW28 rotor at 4° C. for 30 min. The membrane pellet was resuspended in a minimum volume of 50 mM Hepes (pH 7.5) and stored at −70° C.

Synthesis of Peptides

Peptides described in Table 2 below were synthesized on an Applied Biosystems 430A peptide synthesizer using FMOC chemistry and an appropriate amino acid addition program according to ABI's recommendations. Peptides were then purified by preparative reverse-phase HPLC. Composition of the peptides was checked by analytical HPLC, amino acid analysis and protein sequencing on an 477A automated pulse-liquid sequencer.

TABLE 2

| Peptide | Sequence | |
|---|---|---|
| Y740 | G E S D G G Y M D M S K | (SEQ ID NO: 1) |
| Y751 | D M S K D E S V D Y V P M L D M K | (SEQ ID NO: 2) |
| Y751.S | C D E S V D Y V P M L | (SEQ ID NO: 3) |
| Y857 | A R D I M R D S N Y I S K G S T F | (SEQ ID NO: 4) |
| Y1313 | E F C P D P L Y E V M L K | (SEQ ID NO: 5) |
| Y527 | R R F T S T E P Q Y Q P G E N L | SEQ ID NO: 6) |
| Y416[a] | R R L I E D N E Y T A R G | (SEQ ID NO: 7) |

[a]This peptide was purchased from Sigma Chemical Co Ltd rather than synthesized.

Phosphorylation of Peptides

Peptides were lyophilised to dryness to remove any contaminating chemicals remaining from synthesis/purification and then dissolved in HPLC grade water at a concentration of ~4 mg/ml.

For small scale phosphorylation: 20 $\mu$g of peptide, 10 $\mu$l 5×kinase buffer (250 mM Hepes (pH 7.4), 750 mM NaCl, 0.1% Triton X-100, 10 nM MnCl$_2$, 60 mM MgCl$_2$, 50% glycerol, 500 mM sodium orthovanadate), 5 $\mu$l A431 membrane preparation and ATP/[$\gamma$-$^{32}$P]ATP (relative amounts depends on aim of phosphorylation). Water was added to adjust the volume to 50 $\mu$l.

For preparative phosphorylation, 2–3 mg of peptide was dissolved in 1.5 ml of water and added to 450 $\mu$l 5×kinase buffer. The pH was adjusted to 7.0. 250 $\mu$l of 0.1M ATP and 500 $\mu$l of A431 plasma membranes (~2 mg/ml) was added and then the reaction was allowed to proceed for 18 h at room temperature with continual mixing.

Isolation of Phosphorylated Peptides by Reverse Phase HPLC

One millilitre of buffer A (Buffer A: 0.08% trifluoracetic acid, 1% acetonitrile in water; Buffer B: 0.08% trifluoracetic acid, 90% acetonitrile) was added to the kinase reaction and mixed. This solution was then spun for 20 min at 10,000 g to pellet the membranes. The supernatant containing the phosphopeptide was then loaded onto a Sep-Pak column (C$_{18}$) equilibrated with buffer A. The column was washed with 20 ml buffer A to elute ATP and then the peptide was eluted with 3×1 ml of 40% buffer B. The OD of the fractions was monitored at 268 nm and fractions containing peptide were pooled and then lyophilised to dryness (note that the phosphorylated Y751 peptide has essentially no absorption at 280 nm). The phosphopeptide was then separated from non-phosphorylated peptide using a 1090 HPLC system. For preparative separation a C$_{18}$ column (Aquapore OD-300, 250×7 mm) equilibrated with 100% buffer A (214 nm (sen. 50 mV)/280 nm (sen. 200 mV) was used with a 2 ml/min flow rate. The peptide was dissolved in 200 $\mu$l HPLC grate water and then loaded via a 500 $\mu$l loop. The column was then washed for 10 min with 100% buffer A before eluting the peptide and phosphopeptide with a 30 min linear gradient 0 to 45% buffer B followed by 5 min linear gradient to 100% buffer B. Peak fractions were collected manually. The pool fractions were diluted with water, lyophilised and then stored at −20° C.

Phosphoamino Acid Analysis of Phosphorylated Peptides

Peptides phosphorylated in the presence of [$\gamma$-$^{32}$P]ATP using either purified EGF receptor or A431 cell membranes were purified by C$_{18}$ Sep-Pak column and HPLC as described above. This material was then hydrolysed at 110° C. for 1 h in 1 ml of 6M HCl. One millilitre of HPLC grade water was added and the sample was centrifuged at 10,000 g for 10 min to removed debris. The remaining supernatant was frozen and lyophilised to dryness. The pellet was resuspended in 2 ml of water, frozen and then lyophilised once more. This material was analysed by two dimensional thin-layer electrophoresis (essentially as described by Cooper et al, 1983).

Coupling of Peptides to Actigel Resin

Peptides were coupled to the matrix essentially as described by the manufacturers. Briefly, 500 $\mu$l (packed volume) of Actigel-ALD Superflow resin (Sterogene, Calif., USA) was washed five times with 100 mM phosphate buffer (pH 7.8) (coupling buffer). Phosphorylated or non-phosphorylated peptide (1 mg) was dissolved in 200 $\mu$l of coupling buffer and added to the resin. NaCNBH$_3$ (coupling solution) was added to a final concentration of 100 mM and this was then mixed at 4° C. for 6 h. The resin was washed with 10 column volumes of 500 mM NaCl and then incubated with 100 mM Tris-HCl (pH 8.0) for 1 h in the presence of coupling solution to block any unreacted sites on the resin. The resin was washed with 500 mM NaCl and finally with coupling buffer plus 500 $\mu$M vanadate and 0.02% NaN$_3$ and then stored at 4° C. Phosphopeptides bound to the Actigel matrix were stable for several months under these conditions.

Binding of Proteins to the Phosphopeptide Columns

Proteins were diluted in binding buffer (50 mM phosphate buffer (pH 7.2), 150 mM NaCl, 0.02% Triton X-100, 2 mM EDTA and 200 $\mu$M sodium orthovanadate), mixed with the appropriate peptide affinity resin and then allowed to bind for 2 h at 4° C. with rotation. The column material was washed repeatedly (>6×) with 50 column volumes of the same buffer and then with various elution buffers containing NaCl, urea or detergents. Bound proteins were either assayed for PI3-kinase activity or were removed from the column by boiling in SDS-PAGE sample buffer and then analysed by SDS-PAGE.

PI3-kinase Assay

PI3-kinase assays were carried out essentially as described in Whitman et al, (1987) in 50 $\mu$l containing 50 mM Tris-HCl (pH 7.5), 50 mM NaCl, 1 mM DTT, 0.5 mM EDTA, 5 mM MgCl$_2$, 100 $\mu$M ATP (plus 0.5 $\mu$Ci [$\gamma$-$^{32}$P] ATP/assay), 1 mM PI plus soluble or column immobilised bovine brain PI3-kinase. Incubation was for 5 min at room temperature. The reaction was terminated by the addition of 100 $\mu$l of 0.1N HCl and 200 $\mu$l chloroform:methanol (1:1). The mixture was vortexed and then centrifuged to separate the phases. The upper phase was discarded and the lower organic phase washed with 80 $\mu$l of methanol: 1N HCl (1:1). After centrifugation the upper phase was again discarded and the lower phase evaporated to dryness. Reaction products were spotted on thin layer Silica gel 60 plates (pretreated with 1% oxalic acid, 1 mM EDTA in water:methanol (6:4)) and developed in chloroform:methanol:4N ammonia (9:7:4).

Preparation of C-terminal Specific Antisera for p85$\alpha$ and p85$\beta$

C-terminal peptide antisera were prepared against the bovine C-terminal sequences determined by cDNA cloning (Otsu et al, 1991). The peptides TLAYPVYAQQRR (SEQ ID NO:8) for p85$\alpha$ and TLAHPVRAPGPGPPAAR (SEQ ID NO:9) for p85β were synthesized by FMOC chemistry and purified by HPLC. The peptides were coupled using gluteraldehyde to KLH and then injected into the lymph nodes of rabbits using methods described in Kypta et al, (1988). Positive antisera as determined by enzyme-linked immunoassay were affinity purified on specific peptide-Actigel affinity columns.

B. Procedure and Results of Purification

Preparation of Y751 Phosphopeptide Column

A 17 amino acid peptide which contains Y751 of the human PDGF-β receptor was chosen for synthesis in an attempt to inlcude all necessary sequence determinants following a survey of the known binding sites for the PI3-kinase (see Table 2 above; reviewed in Cantley et al, 1991). In addition to the peptide context of Y751 of the PDGF β-receptor, the sequences around Y315 of polyoma middle T (Talmage et al, 1989) and Y721 of the human CSF-1 receptor (Shurtleff et al, 1990) were also considered. Using the phosphorylation protocol described above, greater than 50% phosphorylation of the Y751 peptide was achieved using either purified human EGF receptor or A431 membranes as a source of protein-tyrosine kinase. The phosphorylated Y751 peptide could be clearly identified during reverse phase HPLC analysis, where it eluted approximately one minute earlier than the nonphosphorylated peptide, since it produced a strong 214 nm absorbance, but little or no 280 nm signal (FIG. 1, panel A). Analysis of the absorption properties showed that phosphorylation of the Y751 peptide let to a shift in the absorption maximum from 280 to 267 nm (FIG. 1, panel B). For large scale phosphorylations A431 membranes were the preferred source of protein-tyrosine kinase activity since they could be more easily generated. However, as the Y751 peptide contains two serines, as well as a single tyrosine residue, it was thought important to demonstrate that peptide was phosphorylated exclusively at the tyrosine residue. This was established by two separate methodologies; analysis of HPLC purified phosphopeptide by phosphoamino acid analysis or by protein microsequencing. Phosphoamino acid analysis of the Y751 peptide, phosphorylated by either purified EGF receptor or A431 membranes, demonstrated that phosphorylation of the Y751 peptide was occuring exclusively at the tyrosine residue (FIG. 1, panel C). Sequence analysis of the phosphorylated and non-phosphorylated peptides also confirmed that both these peptides were 17 amino acids in length and that their sequences were identical except at cycle 10 where as expected no phenylthiohydantoin-Tyr derivative was observed for the phosphorylated peptide due to its modification.

Extended Purification of Bovine Brain PI3-kinase Using a Y751 Phosphopeptide Affinity Column A 650-fold purification of PI3-kinase from bovine brain has recently been described (Morgan et al, 1990), and this same method was used except that the gradient for the second Mono Q column was extended to give two distinct peaks containing PI3-kinase activity (FIG. 2, panel A). Both of these peaks (referred to hereafter as peak 1 (P1) and peak 2 (P2)) contained no PI kinase activity other than PI3-kinase activity as determined by HPLC analysis of deacylated product lipids (data not shown). However, both of these fractions still contained greater than 20 peptides detectable after SDS-PAGE gel analysis by silver staining (see FIG. 2, panel A). The precise subunit composition of the active PI3-kinase complex was still a point of some contention, so an attempt was made to address this question by affinity purifying the PI3-kinase activity from these two Mono Q pools. The bovine brain PI3-kinase preparation was diluted 10-fold in binding buffer and allowed to bind batchwise to the Y751 phosphopeptide affinity resin for 4 h at 4° C. After washing the column extensively with binding buffer, those proteins which remained bound were eluted with SDS-containing buffers and examined by SDS-PAGE. Two major polypeptide species of approximate molecular weights 85 and 110 kD, which bound specifically to the phosphopeptide column, but not to an identical column prepared with unphosphorylated Y751 peptide, were identified in both Mono Q peaks and were observed to be quantitatively depleted from the bovine brain PI3-kinase preparation (FIG. 2, panel B). Assaying the bound material, the presence of these two proteins appeared to be sufficient to generate full PI3-kinase activity (FIG. 3, lane 2). With fresh preparations of bovine brain PI3-kinase this column routinely removed >90% of the PI3-kinase activity present in Mono Q peaks 1 or peak 2 (c.f., FIG. 3, lanes 2 and 3) following a single incubation. Neither the 85 and 110 kD proteins, nor PI3-kinase activity bound to a column with an equivalent concentration of non-phosphorylated Y751 peptide (FIG. 3, lane 1) or to a column prepared with phosphotyramine, a phosphotyrosine analogue (data not shown). It should also be noted that binding of the PI3-kinase complex to the phosphopeptide column did not result in any apparent increase in the total enzyme activity present (FIG. 3, c.f., lanes 2 and 6). In fact a slight decrease in activity was often observed, but this was judged to be due to the unstable nature of the highly purified enzyme which was found to be inhibited by traces of metal ions and reversibly inhibited by oxidation. It is estimated that this affinity purification step results in a 7–8,000-fold purification of PI3-kinase from bovine brain relative to the DEAE load (the overall purification achieved from tissue is in fact much greater).

Elution of p85, p110 and P13-kinase Activity from the Phosphopeptide Column

Elution of the above PI3-kinase complex from the phosphopeptide column proved to be difficult to achieve due to the high affinity of the interaction. Kazlauskas and Cooper (1990) have previously noted that the binding of cellular p85 proteins to phosphorylated PDGF-receptor was stable to treatment with solutions containing ionic detergents, 2M NaCl, 1M urea or 0.2% SDS. The p85 subunits and PI3-kinase complex were also found to bind tightly to the Y751 phosphopeptide matrix, and were likewise not eluted under any of the above conditions. At 20° C. the 85 and 110 kD proteins remained bound in the presence of either 2M NaCl plus 0.5% Triton X-100, 5M NaCl, 6M Urea, 50 mM phosphotyrosine or up to 1 mg/ml free Y751 phosphopeptide. Several alternative elution protocols were investigated without success. An elution medium supplied with the Actigel resin was able to remove both proteins but led to a complete loss of activity. Interestingly no suitable conditions could be established whereby the 110 kD, but not the 85 kD, subunit was released from the column suggesting that the interaction between the 110 and 85 kD subunits is of high affinity. Elution of bound proteins was routinely carried out by heating the resin to 80° C. for 3 min in the present of 5 mM phosphate buffer (pH 7.0), 0.1% SDS, 0.1 mM DTT, 10% glycerol. The phosphopeptide column could be simply regenerated following elution by extensive washing in binding buffer (FIG. 3, lanes 4 and 5) and could be successfully used at least ten times before any deterioration in binding was observed.

Analysis of the p85 and 110 kD Proteins Bound to the Phosphopeptide Column

The relationship of the 85 kD proteins observed to bind to the Y751 phosphopeptide column to the recently cloned p85α and p85β proteins was investigated using the polyclonal antisera generated against the predicted C-terminal 12 and 18 amino acids of p85α and p85β, respectively. Despite the high degree of overall sequence similarity between p85α and p85β, the amino acid sequence over this segment is significantly different and thus p85α or p85β specific antisera were expected to be produced. Furthermore the amino acid sequence corresponding to this peptide in p85α is completely conserved between human, bovine and murine cDNAs suggesting that antibodies generated against this sequence might be useful for studying the expression of different p85 proteins in species other than bovine (Escobedo et al, 1991b; Otsu et al, 1991; Skolnik et al, 1991). The corresponding region of p85β in species other than bovine is currently unknown.

The p85 antisera generated against these peptides could specifically immunoprecipitate the appropriate species of expressed recombinant p85 from either COS-1 or Sf9 cells but were not very efficient at immunoprecipitating PI3-kinase activity from either cell lines or from the partially purified bovine brain PI3-kinase preparation. However, these antisera were found to work well in Western blots. The data presented in FIG. 4 shows that these two antisera specifically recognized expressed p85 proteins present in either COS cells or in Sf9 cells. Longer exposures also revealed the endogenous COS p85 protein(s), but no such proteins were detected in Sf9 cells with these antisera. No cross reactivity was observed even at high concentrations of the recombinant proteins suggesting that they are specific for p85α (FIG. 4, panel A) and p85β (FIG. 4, panel B) respectively. The ability of these antisera to interact with the appropriate p85 species was demonstrated to be completely blocked in the presence of the appropriate peptide used ot raise the antisera (FIG. 4, panel C). The p85 species in the two peaks of bovine brain PI3-kinase activity which bound to the Y751 phosphopeptide column was found to react exclusively with the anti C-terminal antisera raised against the p85α specific sequence (FIG. 4, panel A). Following immobilisation of the bovine brain PI3-kinase material on the Y751 phosphopeptide column, all the p85α immunoreactive material was bound to the column with none detectable by either silver staining or Western blot analysis in the supernatant (FIG. 4, panel D).

For sequence analysis of the PI3-kinase complex, the 110 and 85 kD subunits were eluted from the column, following extensive stringent washing, by briefly boiling the resin in 5 mM phosphate buffer (pH 7.0), 0.1% SDS, 0.1 mM DTT, 10% glycerol. Preparation of both 85 and 110 kD proteins for digestion with lysylendopeptidase and subsequent sequence analysis were performed in accordance with the protocol given hereinbefore. Amino acid sequence analysis of a lysylendopeptidase C digest of the p85 protein bound to be Y751 phosphopeptide column confirmed that the p85 protein present in both peak 1 and peak 2 from the mono Q column were identical to the previously cloned p85α (Otsu et al, 1991). No peptides corresponding to p85β were found in either peak. Extensive sequencing of the 110 kD protein affinity purified from both mono Q peak 1 and peak 2 material enabled the isolation of a novel cDNA (see below).

Specificity of Binding of the Purified Bovine Brain PI3-kinase

In order to evaluate the specificity of the Y751 phospopeptide column for purifying the PI3-kinase, other phosphopeptide columns were prepared using peptides based on the amino acid sequences which surround known protein-tyrosine kinase phosphorylation sites. Tyrosine 857 is the other major autophosphorylation site in the human PDGF β-receptor and has been shown to be required for the binding of GAP, but not for association with the PI3-kinase (Kazlauskas & Cooper, 1989, 1990; Kazlauskas et al, 1991). For a direct comparison with the Y751 peptide a 17 amino acid peptide centred around tyrosine residue 857 was synthesized (see Table 2 above). A comparison the proteins from baculovirus expressing p85α Sf9 cell lysate or from bovine brain PI3-kinase fractions from mono Q peak 1 (P1) and peak 2 (P2) binding to either the Y751 (panel A) or Y587 (panel B) phosphopeptide columns is shown in FIG. 5. Whereas the baculovirus expressed p85α is observed to bind both columns to a similar extent, the 85 and 110 kD proteins from both peaks of activity are seen only to bind to the Y751 phosphopeptide column. Similarly, PI3-kinase activity is only found associated with the Y751 phosphopeptide column (FIG. 7, panel B).

To determine whether this binding specificity could be extended several other peptides were synthesized based on known tyrosine autophosphorylation sites (see Table 2 above). A shorter, 11 amino acid version of the Y751 peptide, termed Y751S, was also synthesized in an attempt to further refine the minimal SH2 recognition domain required. Two other peptides containing the YXXM motif were prepared, one based on the seqeunce around tyrosine 740 of the PDGF-β receptor, a second residue within the PDGF receptor kinase insert which may play a role in PI3-kinase binding (Escobedo et al, 1991a), and the second based around tyrosine Y1313 of Met, the hepatocyte growth factor receptor. To introduce a totally random sequence the synthetic peptide poly Glu:Ala:Tyr (6:3:1) was also phosphorylated and coupled to the Actigel matrix. Finally the peptides surrounding the two major phosphorylation sites from $pp60^{c-src}$ Y416 and Y527, were purchased and synthesized respectively. All peptides efficiently phosphorylated specifically on tyrosine residues using the EGF receptor and then were purified by HPLC as described above for the Y751 phosphopeptide.

Baculovirus expressed bovine p85α and p85β were chosen to test these columns (Otsu et al, 1991). Binding analysis was carried out under identical conditions to those previously established for the Y751 phosphopeptide column. Somewhat unexpectedly the baculovirus expressed p85 subunits bound to all phosphopeptide columns tested (see FIG. 7, panels A and B). They did not however bind to identical columns containing non-phosphorylated peptides (FIG. 6, panels A and B, lane 1 and data not shown). However when partially purified bovine brain PI3-kinase was applied to these columns it was found to bind exclusively to the phosphopeptide columns containing a YXXM motif (see FIG. 7 and FIG. 8, panel A).

That the Y751S phosphopeptide column appears to be as efficient at binding the active PI3-kinase complex as the longer Y751 phosphopeptide column suggests that the consensus sequence recently proposed by Cantley et al, (1991) does indeed contain all the sequence data necessary for correct recognition by the PI3-kinase SH2 domain (FIG. 8, panel B).

Cloning of p110

C. Experimental Procedures

Materials

Restriction enzymes and DNA modification enzymes were obtained from standard commercial sources and used according to the manufacturer's recommendations. Oligonucleotides were synthesized on an Applied Biosystems 380B DNA synthesizer and used directly in subsequent procedures.

Cells

The SGBAF-1 cell line was established by transfection of bovine adrenal cortex zona faciculata cells with pSV3neo as previously described for other cell types (Whitley et al, 1987). SGBAF-1 cells and COS-1 cells were maintained in Dulbecco's modified eagle medium (DMEM) containing a 10% foetal calf serum (FCS). Maintenance of Spodoptera frugiperda (Sf9) cells was carried out as described by Summers and Smith, 1987.

Protein Purification and Amino Acid Sequence Determination

The purification of the p85α and p110 proteins by chromatography on a peptide affinity column corresponding to amino acids 742–758 of the kinase insert region of the human PDGF-β receptor has been described above. The method used for the final purification of p110 for amino acid sequence analysis was in accordance with the Protocol given hereinbefore. This procedure was carried out on three separate PI3-kinase preparations. A fourth preparation was eluted from the matrix as before and boiled for 5 min. After cooling, the sample was diluted with 25 -mM Tris-HCl, pH 8.8 and digested directly with lysylendopeptidase for 72 h at 30° C. Peptides were separated as above. Peptide sequences were determined using a modified Applied Biosystems 477A automated pulse-liquid sequencer.

MRNA Isolation and CDNA Cloning

Total RNA was isolated from the SGBAF-1 by the method of Chirgwin et al. (1979) and poly(A)$^+$ mRNA selected by chromatography on oligo-dT cellulose (Maniatis et al., 1982). An oligo-dT primed cDNA library of $5 \times 10^6$ primary recombinants was constructed in lambda Uni-Zap (Stratagene) from 5 μg of this mRNA using the Stratagene Uni-Zap cDNA cloning system. The construction of the total bovine brain cDNA library in lambda Uni-Zap has been described previously (Otsu et al, 1991).

Library Screening and Hybridizations

The unamplified SGBAF-1 cDNA library ($10^6$ recombinants) was plated on E. coli K12 PLK-F' (Stratagene) at a density of $10^5$ plaques per 15 cm dish and lifts taken in duplicate onto nitrocellulose membranes (Millipore). For screening, filters were prehybridized for at least 1 h at 42° C. in 6xSSPE, 0.5% SDS, 10xDenhardt's solution, 100 μml$^{-1}$ denatured sonicated herring sperm DNA (Sigma). Hybridization was carried out in the same solution containing 10 ng ml$^{-1}$ radiolabelled oligonucleotide. oligonucleotides used were: Peptide N (MDWIFHT) (SEQ ID NO:11) 5'-AA(G/A)ATGGA(T/C)TGGAT(C/T/A)TT(T/C) CA(T/C)AC-3' (SEQ ID NO:12); Peptide J (D D G Q L F H I D F G H F) (SEQ ID NO:13) 5'-GATGATGGCCA(G/ A)CTGTT(T/C)CA(T/C)AT(T/A)GA(T/C)TTTGGCCA (T/C)TT (SEQ ID NO:14). Oligonucleotides were labelled with $^{32}$P at the 5' end in a 20 μl reaction containing 100 ng oligonucleotide, 1xkinase buffer (Promega), 0.1 mM spermidine, 5 mM dithiothreitol, 100 μCi [γ-$^{32}$P]ATP (5000 Ci mmol$^{-1}$, Amersham) and 2 μl (20 U) T4 polynucleotide kinase (Amersham). Filters were washed in 6xSSC, 0.1% SDS at room temperature and then subjected to autoradiography using Kodak XAR film. Hybridizing clones were plaque-purified and rescued as plasmids according to the manufacturers instructions.

Characterization of cDNA Clones

Sequencing was carried out by the chain termination method using the Sequenase system (United States Biochemicals). Clones for sequencing were obtained by directed cloning of restriction fragments into M13 mp18 and mp19 vectors (Yanisch-Perron et al., 1985) and by making a series of exonuclease III mediated deletions (Henikoff, 1984; Pharmacia Exonuclease III deletion kit). DNA sequences were analysed on a MicroVAX computer using the Wisconsin (UWGCG: Devereux et al., 1984) sequence analysis package.

RACE PCR

RACE PCR was carried out essentially as published previously (Frohman et al., 1988; Harvey and Garlison, 1991). Briefly, first strand cDNA primed with random hexamers (Amersham) was synthesized from 1 μg of SGBAF-1 cell mRNA using the Stratagene first strand cDNA synthesis kit. First strand cDNA was isolated by isopropanol precipitation and tailed with oligo-dA using terminal deoxynucleotidyl transferase (BRL). PCR was performed using oligo 2224 (5'-AATTCACACACTGGCATGCCGAT) (SEQ ID NO:15) and adaptor-dT (5'-GACTCGAGTCGACATCGATTTTTTTTTTTTTTTT) (SEQ ID NO:16) as primers using a Perkin Elmer/Cetus Tap polymerase PCR kit (conditions: 94° C. 1 min, 35° C. 1 min, 72° C. 2 min, 30 cycles). Products were fractionated on a 1.5% low melting point agarose gel and visualized by staining with ethidium bromide. The gel was sliced into 6 bands (size range 150–2000 bp) and DNA isolated from each gel slice. A further round of PCR was performed on this DNA using oligonucleotide 2280 (5'-TTTAAGCTTAGGCATTCTAAAGTCACTATCATCCC) (SEQ ID NO:17) and adaptor (5'-GACTCGAGTCGACATCGA) as primers (conditions: 94° C. 1 min, 56° C. 1 min, 72° C. 2 min, 35 cycles). Products were fractionated on an agarose gel and visualised by staining with ethidium bromide. A band 250 bp shorter than the size of the DNA in the gel slice used for the PCR was expected. An intensely staining band of 350 bp obtained from the ~600 bp gel slice was excised, digested with HindIII and SalI and ligated into Bluescript KS- digested with HindIII and XhoI to give plasmid pBS/race. Two independent inserts were completely sequenced.

Southern Transfer Hybridizations

High molecular weight DNAs were isolated from cell lines by standard techniques (Maniatis et al, 1982). DNAs were digested with restriction endonucleases, fractionated through 0.5% agarose gels and transferred to nitrocellulose (BA85, Schleicher and Schuell) as described in Maniatis et al (1982). Prehybridization was carried out in 1M NaCl, 10xDenhardt's solution, 50 mM Tris-HCl (pH 7.4), 10 mM EDTA, 0.1% SDS and 100 μg ml$^{-1}$ denatured sonicated herring sperm DNA at 65° C. Hybridization was carried out overnight in the same solution containing 20 ng ml$^{-1}$ radiolabelled probe fragment (0.88 kb XbaI-Psti fragment: Probe a, FIG. 9, lower panel) of specific activity >$10^8$ dpm μg$^{-1}$). Probe fragments were isolated from agarose gels be electroelution (Maniatis et al, 1982) and labelled by nick translation (Rigby et al, 1977) using [α-$^{32}$P] dATP(>3000 Ci mmol-1, Amersham). Membranes were washed extensively in 0.1xSSC, 0.1% SDS at 68° C. or at 50° C. in 0.5xSSC, 0.1% SDS to detect related sequences, and subjected to autoradiography with Kodak XAR film.

Northern Transfer Hybridizations

Poly(A)$^+$ RNA from total bovine brain or the SGBAF-1 cell line was modified with DMSO and glyoxal and fractionated on a 0.9% agarose gel run in 10 mM phosphate buffer (pH 7.5) (Maniatis et al, 1982). Nucleic acid was transferred to nylon membranes (Hybond-N, Amersham) and filters baked dry. Prehybridization was carried out at 60° C. in 50% formamide, 5xSSPE, 5xDenhardt's solution, 0.2% SDS, 200 μg ml$^{-1}$ denatured sonicated herring sperm DNA and 200 ug ml$^{-1}$ yeast RNA. Hybridization was carried out in the same solution containing $1 \times 10^7$ cpm ml$^{-1}$ antisense RNA probe. Probe was prepared by in vitro transcription of a 2 kb fragment (nucleotides 598–2608; Probe b, FIG. 9, lower panel) subcloned in pSPT19 (Boehringer), using SP6 RNA polymerase (Amersham) and [$\alpha^{32}$-p] UTP (Amersham) according to the manufacturers conditions. Membranes were washed in 0.1×SSC, 0.1% SDS at 60° C. Filters were treated with 1 μg ml$^{-1}$ RNAase A (Sigma) in 2×SSC for 15 min at room temperature and the filter rinsed at 50° C. in 0.1×SSC. Filters were then subjected to autoradiography against Kodak XAR film at −70° C.

PCR Determination of p85α and p110 mRNA

For p85α 125 ng of poly (A)$^+$ RNA was reverse transcribed with 2.5 units rtth DNA polymerase (Perkin-Elmer-Cetus) at 70° C. for 10 min in a 10 μl reaction containing 10 mM Tris-HCl (pH 8.3), 90 mM KCl, 1 mM MnCl, 0.5 mM dNPT mixture and 1.2 μM antisense primer (5'-CAGGCCTGGCTTCCTGT) (SEQ ID NO:19). For DNA polymerization the reaction volume was adjusted to 50 μl by adding a single mix giving the following final concentrations: 5% (v/v) glycerol, 10 mM Tris-HCl (pH 8.3), 100 mM KCl, 0.75 mM EGTA, 0.05% (v/v) Tween 20, 2 mM MgCl$_2$, 0.24 μM sense primer (5'-AACCAGGCTCAACTGTT) (SEQ ID NO:20). PCR was then performed under the following reaction conditions: 92° C. 1 min, 58° C. 1 min, 72° C. 1 min for 25 cycles on a Perkin Elmer-Cetus DNA thermal cycler.

Conditions for p110 were similar except concentration of the antisense primer (5$^1$-TGCTGTAAATTCTAATGCTG) (SEQ ID NO: 21) was increased to 4.8 μM during the reverse transcription step. DNA polymerisation conditions were the same except the final MgCl$_2$ concentration was increased to 2.5 mM and both primers (sense primer=5'-GTATTTCATGAAACAAATGA) (SEQ ID NO:22) were present at a final concentration of 0.96 μM. Taq DNA polymerase (Promega) was also added at 0.03 U μl$^{-1}$. PCR was performed as follows: 92° C. 30 sec, 54° C. 5 sec, 72° C. 30 sec for 35 cycles. 20 μl of each reaction was run on a 3% agarose gel (Maniatis et al, 1982) and visualised by staining with ethidium bromide.

Antibodies and Immunoprecipitations

For the preparation of the anti C-terminal p100 antiserum, peptide CKMDWIFHTIKQHALN (SEQ ID NO:23) was synthesized by FMOC chemistry and purified by HPLC. It was then coupled to KLH using glutaraldehyde, and injected into the lymph nodes of rabbits using methods described in Kypta, R M et al., (1990), Cell 62, 481–492. Positive antisera as determined by enzyme-linked immunoassay were affinity purified on specific peptide-Actigel affinity columns. Anti-p85α (Otsu et al, 1991) and anti CSF-1 receptor (Ashmun et al., 1989) antisera are previously documented. Immunoprecipitations were carried out as described in Otsu et al., 1991.

PI3-kinase Assay

The assay for PI3-kinase activity was carried out as described by Whitman et al. (1985).

Expression of p110 in Sf9 Cells

To clone the p110 coding region into the baculovirus transfer vector p36C (Page, 1989) a Sau 3A1 site (GGATCA) present 10 nucleotides upstream from the initiation codon (see FIG. 9) was changed to a BamHl (GGATCC site by PCR mediated mutagenesis. Briefly, a sense oligonucleotide substituting C for A at position 6 of the Sau3Al site was used in a PCR reaction with an antisense primer comprising nucleotides (102–124) of the p110 sequence (see FIG. 9) using Vent polymerase (New England Biolabs). Template DNA was random-primed first strand cDNA prepared from SGBAF-1 cell mRNA as described above; PCR conditions: 94° C. 1 min, 50° C. 1 min, 72° C. 2 min, 35 cycles. The PCR product was digested with BamHl-EcoNl and a 118 bp fragment isolated from a low melting point agarose gel. This BamHl-EcoNl fragment was cloned into p110/2.2 digested with BamHl (present in vector sequences) and EcoNl (nucleotide=108) giving plasmid p110/(BamHl). The BamHl-EcoNl fragment of p110/(BamHl) was sequenced and found to agree with that previously determined. A 3.4 kb BamHl-Kpnl (Kpnl site present in the vector) fragment was isolated from p110/(BamHl) and ligated into p36C baculovirus transfer vector (Page, 1989) previously digested with the same enzymes. Recombinant viruses were obtained as described in Summers and Smith (1987). Sf9 cells were infected at a multiplicity of infection of 10 with recombinant viruses in IPL-41 media supplemented with 10% FCS. Cells were harvested and lysed 2 days post-infection in EB lysis buffer (20 mM Tris-HCl (pH 7.4), 50 mM NaCl, 50 mM NaF, 1% NP40, 1 mM EDTA, 500 μM sodium orthovanadate, 2 mM PMSF, 100 Kallikrein inhibitor units of Aprotinin ml$^{-1}$) (Kazlauskas and Cooper, 1989) and lysates were analysed by immunoappreciation.

Association of p110 and p85α with CSF-1 Receptor

This assay was performed essentially as described by Kazlauskas and Cooper (1990). Sf9 cells were infected as already described and lysed 48 h post-infection in EB lysis buffer. CSF-1 receptor was immunoprecipitated from Sf9 cells and collected on Protein A-Sepharose beads. The immunocomplex was then subjected to extensive washing (3 times with EB lysis buffer, twice with kinase buffer; 50 mM HEPES (pH 7.4), 150 mM NaCl, 0.02% Triton X-100, 12 mM MgCl$_2$, 2 mM MnCl$_2$, 10% glycerol, 500 μM sodium orthovanadate) and the receptor phosphorylated for 15 min at 20° C. with ATP. The precipitates were then washed again to remove free ATP and incubated for 2 h at 4° C. with cell lysates prepared from Sf9 cells infected with viruses expressing (i) p85α, (ii) p110 or (iii) co-infected with viruses expressing p85α and p110. The immune complexes were washed and assayed for associated PI3-kinase activity.

Expression of p85α and p110 in COS-1 Cells

For transient expression of p85α in COS-1 cells the coding region for p85α was cloned into the adenovirus late promoter based expression vector pMT2 (Kaufman et al, 1989) as previously described (Otsu et al, 1991). For expression of the p110 cDNA plasmid pSG5-p110 was constructed as follows. The 3.4 kb BamHl-Hindlll fragment from cDNA p2.1 was ligated into pSG5 (Stratagene) cut with BamHl and Bglll, the Hindlll and Bglll overhangs of p2.1 and pSG5 respectively, being filled in with Klenow polymerase. This gave construct pSG5.2. Plasmid pBS/race (above) was digested with EcoRl and Hindlll, the 350 bp band gel purified by electroelution (Maniatis et al, 1982) and further digested with Sau3Al and Bsml. This mixture was then added to the gel purified Bsml-BstMl fragment from p2.1 and ligated in a three fragment ligation to pSG5.2 digested with BamHl and BstXl. 5 μg of each DNA was transfected into 10 cm dishes of 80% confluent COS-1 cells using Lipofectin (BRL) under conditions suggested by the manufacturers. Lysates were analysed by immunoprecipitation with anti-p85α polyclonal antiserum or with anti-p110 C-terminal peptide antiserum. Immunocomplexes collected on Protein A-Sepharose beads were analysed either on 10% SDS-PAGE gels followed by autoradiography or subjected to in vitro PI3-kinase assays as described.

D. Results of Cloning cDNA Cloning and Deduced Amino Acid Sequence of p110

Initially, an oligo(dT) primed bovine brain cDNA library (Otsu et al, 1991) was screened with oligonucleotide probes made against peptides J and N (see FIG. 9). No hybridizing clones were detected. Therefore, a new cDNA library of $5 \times 10^6$ primary recombinants was constructed from mRNA isolated from a pSV3neo transfected bovine adrenal cortex zona fasciculate cell line (SGBAF-1), which was known to contain PI3-kinase activity (Otsu et al, 1991). Screening of $1 \times 10^6$ primary recombinants from this library with the same oligonucleotides led to the detection of 66 clones positive with both probes. Twenty overlapping clones were characterized and found to possess inserts from 1–4 kb. The clone with the longest insert representing coding sequence (clone p110/2.1) was completely sequenced. This revealed a potential open reading frame (ORF) of 1053 amino acids with a predicted molecular weight of 123 kD. The ORF contained all the sequenced peptides, but was not preceded by in-frame stop codons. Since the predicted size of the p110 protein from SDS gels is 110 kD, it was possible that the protein could initiate from an internal methionine within this ORF.

Expression studies carried out in COS-1 cells using methionines 16, 30, 123 and 130 as potential start codons (initiation at Met 123 would give rise to a protein of 110 kD) did not lead to the syntheses of a protein corresponding to p110 or any augmentation of PI3-kinase activity in these cells. This suggested p110/2.1 is missing 5' coding sequence and that either p110 protein runs anomalously on SDS-PAGE gels or that it is synthesized as part of a larger precursor molecule. Characterization of the remaining 46 positive clones initially isolated, showed that all had inserts shorter than that in clone p110/2.1. To further extend the p110/2.1 cDNA in the 5' direction a RACE (rapid amplification of cDNA ends) polymerase chain reaction (PCR) (Frohman et al, 1988; Harvey and Garlison, 1991) was used. Two independent products which extended the known nucleotide sequence were characterized (see FIG. 9, lower panel). The nucleotide and deduced amino acid sequences for the coding region of the composite cDNA are presented in FIG. 9. The putative initiation codon is preceded by an in-frame stop codon and occurs in a Kozak consensus sequence (Kozak, 1987) for the initiation of translation (data not shown). The deduced amino, acid sequence encodes a protein of 1068 amino acids with a calculated relative molecular mass of 124,247.

Analysis of the p110 Nucleotide and Deduced Amino Acid Sequences

The coding region of the cDNA for p110 is extremely A+T rich (G+C content=39.3%) which is reflected in the failure to use codons TCG (Serine) and GTC (Valine). When the p110 amino acid sequence was compared with sequences in the Swissprot and NBRF protein databases, significant homology was found to only one protein, Vps34p (FIG. 10). This is a rare 100 kD protein from Saccharomyces cerevisiae involved in the sorting of proteins into the yeast vacuole and in the vacuole morphogenesis during budding (Herman and Emr, 1990). A search of the p110 sequence for amino acids conserved in the active sites of kinases, reveals $G_{842}$, $K_{863}$, $D_{916}$, $N_{921}$, and the DFG triplet at residues 933–935 (these residues are marked in FIG. 2B) which might be homologous to $G_{52}$, $K_{72}$, $D_{166}$, $N_{171}$ and the DFG triplet at residues 184–186 in cAMP-dependent protein kinase (Knighton et al, 1991a,b). Equivalent residues are present in Vps34p and are also marked in Figure X. The glycine rich P-loop (Saraste et al., 1990), found in many kinases (Hanks et al., 1988), does not appear to be present in either p110 or Vps34p.

Genomic Southern Blot Analysis of p110 Genes

Given the occurrence of at least two forms of p85 (Otsu et al, 1991), Southern blot analysis was used to analyse the number of p110 related genes which occur in genomic DNA isolated from bovine, human and rat sources. The analysis clearly provides evidence for a second, closely related, gene in rat and human genomic DNA (e.g. compare FIG. 11A lanes 4 and 9 with FIG. 11B lanes 4 and 9). For bovine DNA there appear to be no hybridization signals removed by washing at higher stringency (compare FIG. 11A lanes 1, 2 and 3 with FIG. 11B lanes 1, 2 and 3). However, it is possible that a related gene exists in bovine DNA, but, either it does not cross-hybridize under the conditions used, or it is too similar in sequence to be detected by differential washing.

Expression of p110 Cells and Tissues

Figure 12A:
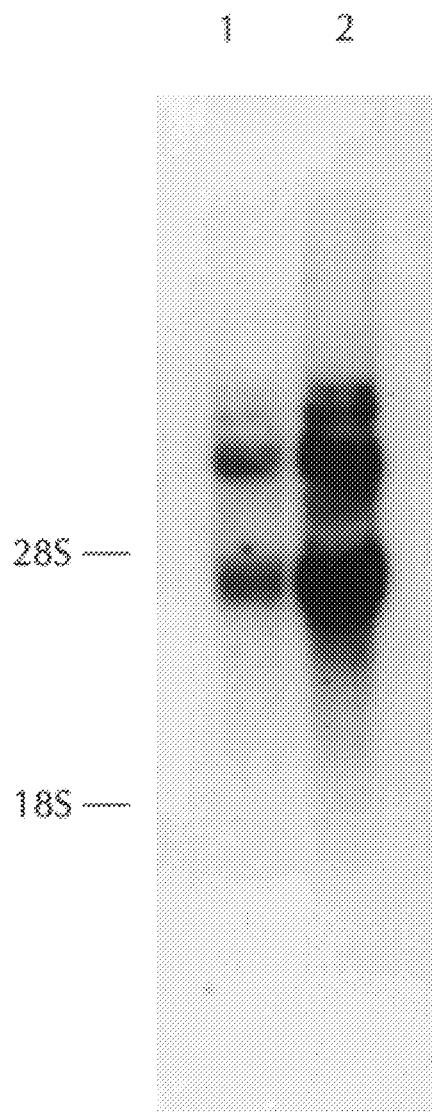
Figure 12B:
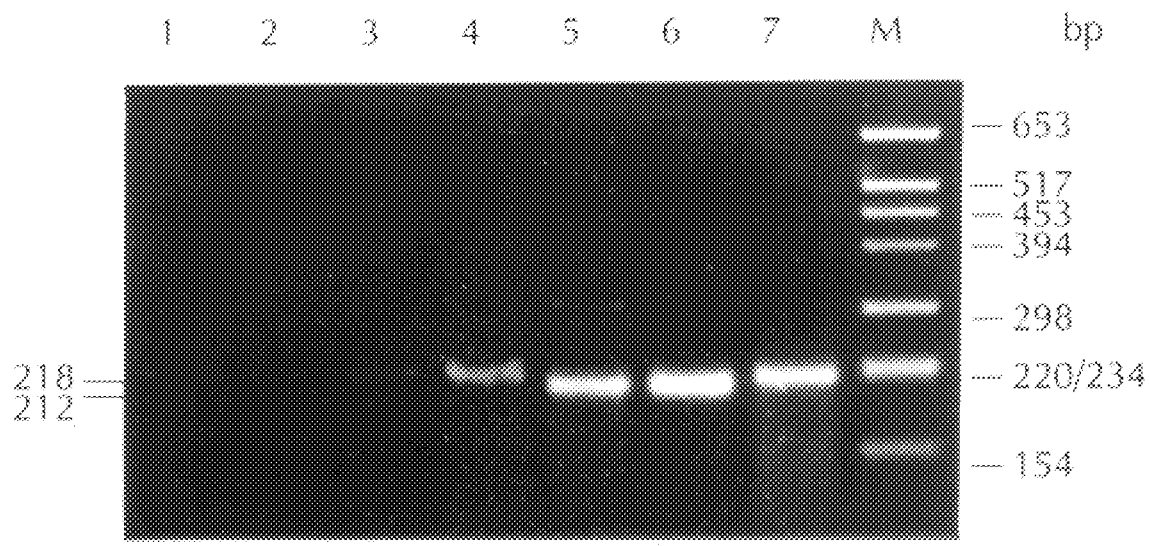
Figure 12C:
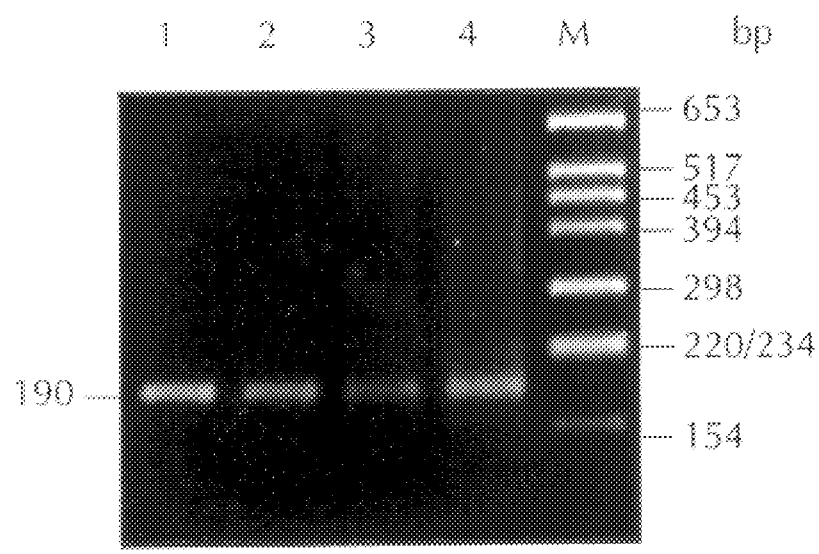
Figure 13A:
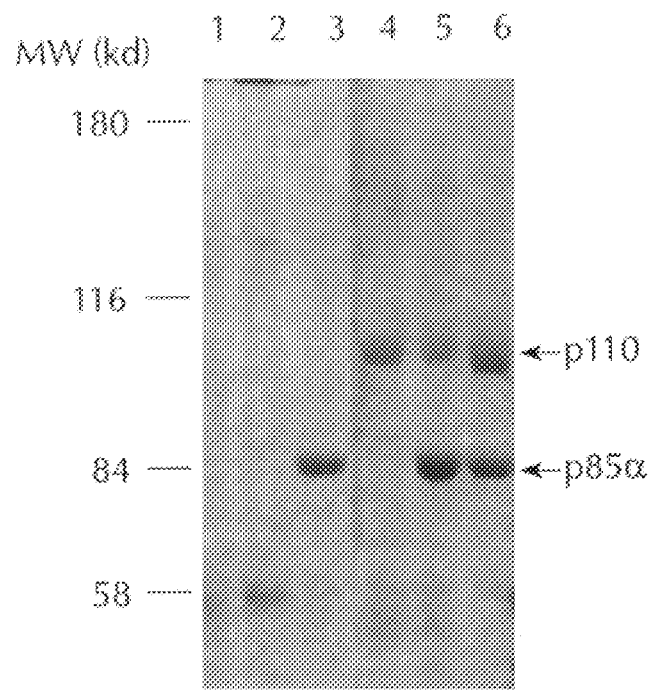
Figure 13B:
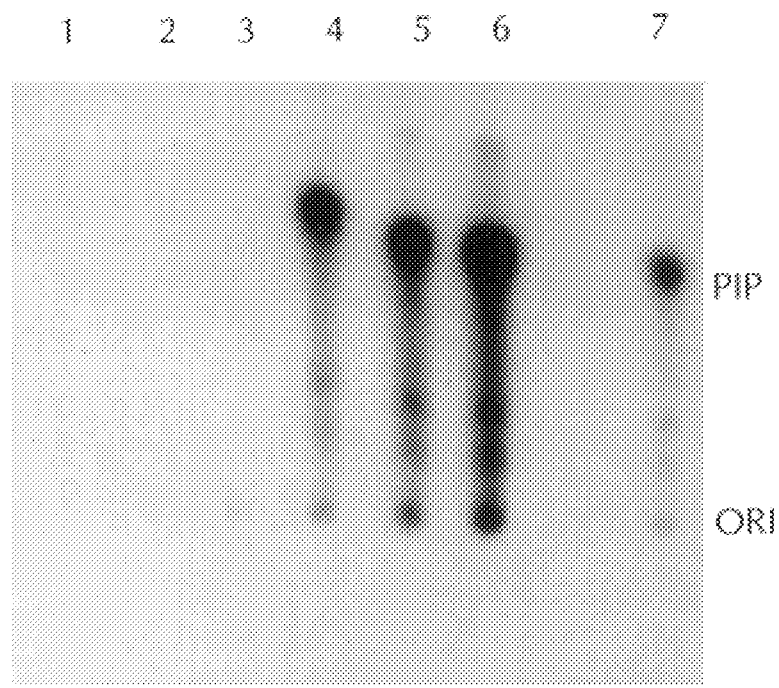

A northern blot analysis carried out on mRNA isolated from the SGBAF-1 cell line and total bovine brain is shown in FIG. 12A. Both mRNA samples contain major p110 specific transcripts of 4.8 kb and 9 kb, although there is substantially more p110 message present in mRNA isolated from SGBAF-1 cells (FIG. 12A, lane 2) than that isolated from total bovine brain (FIG. 12A, lane 1). A PCR based study was performed to examine the distribution and conservation of p110 mRNA in cell lines and tissue from several species. Amplification of a p110 specific fragment is seen for three human mRNAs (218 bp; FIG. 12B lanes 1, 2 and 3) and two bovine mRNAs (212 bp; FIG. 12B, lanes 5 and 6). Similar sized fragments are amplified from cell lines of simian and porcine origin (FIG. 12B, lanes 4 and 7, respectively), indicating the existence of a p110 homologue in these species. An additional band of 300 bp is amplified from bovine brain mRNA (FIG. 12B, lane 5) and its identity is currently being investigated. Since PI3-kinase activity may reside in a p85α/p110 complex (Carpenter et al, 1990; Otsu et al., 1991; Shibasaki et al., 1991), some of these cell lines were examined to see whether messages for p85α and p110 are co-expressed. Amplification of a p85α specific 190 bp fragment is seen for the three human omission (FIG. 12C, lanes 1, 2 and 3) cell lines and one simian (FIG. 12C, lane 4) cell line analysed. Thus, at least in these four cell lines, messages for p85α and p110 are co-expressed.

p110 cDNA Encodes a Protein of Apparent Molecular Weight 110 kD which Possesses PI3-kinase Activity To demonstrate that the p110 cDNA encodes the 110 kD subunit of PI3-kinase, it was expressed in the baculovirus expression system (Summers and Smith, 1987). Immunoprecipitation with an anti-p110 antiserum from Spodoptera frugiperda (Sf9) cells infected with the p36C-p110 virus revealed a novel protein of apparent molecular weight 110 kD (FIG. 13A, lane 4) which co-migrated with the p110 PI3-kinase subunit purified from bovine brain. No such protein was seen in anti-p110 immunoprecipitates prepared from cells infected with a control wild-type virus (FIG. 13A, lane 2). This baculovirus expressed p110 was used to examine whether p110, alone, possesses catalytic activity or whether a p85α/p110 complex is required. When assayed, p110-containing immunoprecipitates were found to possess significant levels of PI3-kinase activity (FIG. 13B, lane 4), the identity of the lipid product being confirmed as PI(3)P by HPLC analysis. No activity was detected in anti-p110 immunoprecipitates prepared from control infected cells (FIG. 13B, lane 2). These results clearly demonstrate that the p110 subunit of PI3-kinase is sufficient for catalytic activity.

p110 Expressed in Insect Cells Forms a Stable Complex with p85α

Since PI3-kinase purified from bovine brain is a complex of p85α and p110, the ability of p85α and p110 expressed in insect cells to reconstitute an active p85α/p110 complex was examined. Baculoviruses expressing either p85α (pAcC4-p85α; Otsu et al, 1991) or p110 (p36C-p110) were infected separately, or together, into Sf9 cells and expressed proteins analysed as described in experimental procedures. Immunoprecipitates of p85α alone (FIG. 13A, lane 3) were inactive in a PI3-kinase assay (FIG. 13B, lane 3) as previously demonstrated (Otsu et al, 1991). In double infection experiments, both p85α and p110 were detected in either anti-p85α (FIG. 13A, lane 5) or anti-p110 (FIG. 13A, lane 6) immunoprecipitates. As neither subunit-specific antiserum recognises the other subunit (see FIG. 15A, lane 3; FIG. 15C, lane 2), the simplest interpretation of this data is that, when expressed in Sf9 cells, p110 and p85α (FIG. 13B, lane 5) or the anti-p110 antisera (FIG. 13B, lane 6) were both active. Neither antiserum immunoprecipitated endogenous PI3-kinase activity from Sf9 cells infected with wild-type virus (FIG. 13B, lanes 1 and 2).

PI3-kinase Activity Expressed in Sf9 Cells Can Associate with the Activated CSF-1 Receptor PI3-kinase activity has been shown to associate with many activated PTK receptors, but particularly well studied have been those receptor PTKs possessing a kinase insert region, e.g., PDGF-β receptor (Coughlin, S R et al., (1989), Science 243, 1191–1193 and the CSF-1 receptor (Varticovski et al, 1989; Shurtleff et al, 1990). An in vitro association assay (Kazlauskas and Cooper, 1990) was used to study the association of PI3-kinase activity expressed in insect cells with the activated CSF-1 receptor. FIG. 14 shows that baculovirus expressed PI3-kinase activity can associate with the CSF-1 receptor, but only from an Sf9 cell lysate containing both p85α and p110 (FIG. 14, lane 2), and only when the receptor has been phosphorylated prior to incubation with Sf9 cell lysate (compare FIG. 14, lanes 2 (+ATP) and 3 (−ATP)). No PI3-kinase activity associates with CSF-1 receptors incubated with Sf9 cells lysates containing p85α alone (FIG. 14, lane 4) or p110 alone (FIG. 14, lane 5). No activity is found associated with the CSF-1 receptor immunoprecipitated from Sf9 cells (FIG. 14, lane 1). Thus, PI3-kinase subunits expressed in insect cells can be used to reconstitute an active p85α/p110 complex that binds to a phosphorylated PTK receptor.

Expression of PI3-kinase in COS-1 Cells

The results shown above were all obtained from expression studies carried out in insect cells. In order to study p110 and its interaction with p85α in a mammalian cell system, transient co-expression studies in COS-1 cells were performed. The p110 cDNA was cloned into the SV40 based expression vector, pSG5 (giving plasmid pSF5-p110) and transfected into COS-1 cells, either alone or together with a p85α expression construct, pMT2-p85α (Otsu et al., 1991). To enable proteins to be more easily visualised transfected COS-1 cells were metabolically labelled with $^{35}$S-methionine for 3–4 h prior to lysis. Radiolabelling at this time results in preferential labelling of proteins synthesized from transfected constructs. Cell lysates were immunoprecipitated with either anti-p85α (FIG. 15, panels A and B) or anti-p110 antisera (FIG. 15, panels C and D). Immunoprecipitated proteins were either visualised by autoradiography following fractionation on SDS-PAGE gels (FIG. 15, panels A and C) or subjected to an in vitro PI3-kinase assay (FIG. 15, panels B and D).

Figure 15A:
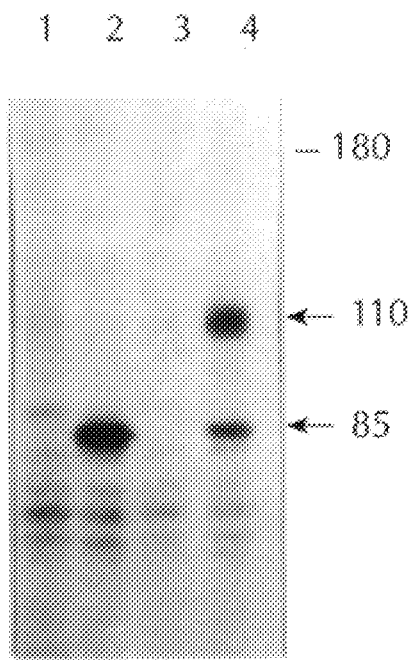
Figure 15B:
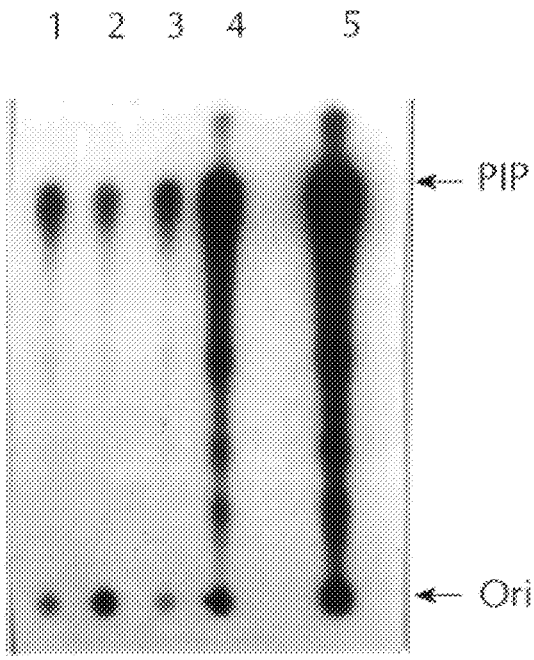
Figure 15C:
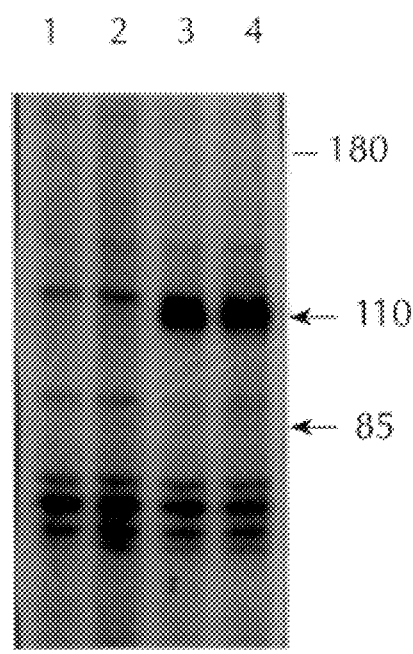

Transfection of pMT2-p85α resulted in a significant elevation of p85α over the background level due to endogenous simian p85α—compare FIG. 15A, lanes 2 and 4 with FIG. 15A, lane 1. In p85α/p110 co-transfectants, the anti-p85α antiserum co-immunoprecipitates p85α and p110 (FIG. 15A, lane 4), demonstrating the existence of a p85α/p110 complex. When assays for PI3-kinase activity were performed on the anti-p85α immunoprecipitates, enhanced activity (10 fold over the background due to endogenous simian PI3-kinase) was only detected with immunoprecipitates which contained both p85α and p110 (compare FIG. 15B, lane 4 with FIG. 15B lanes 1, 2 and 3). These results demonstrate that in COS-1 cells, as in Sf9 cells, the p110 cDNA directs the synthesis of a protein of molecular weight 110 kD, which associates with p85α to give a p85α/p110 complex that possesses PI3-kinase activity.

Figure 15D:
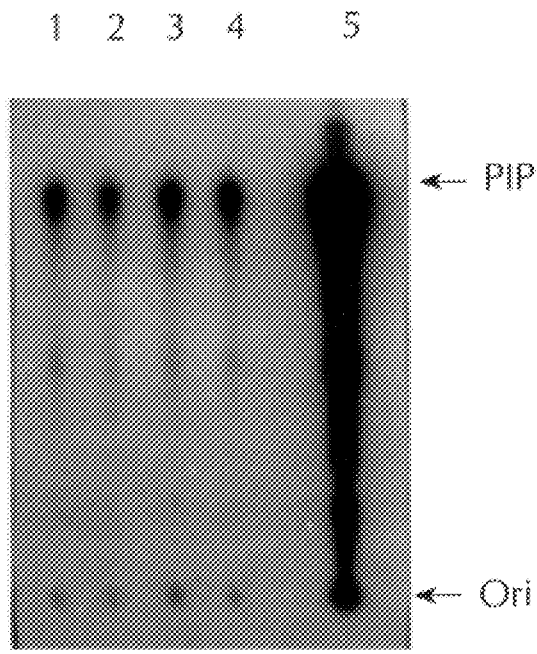

However, when proteins were immunoprecipitated from the same lysates with the anti-p110 antiserum and PI3-kinase assays performed, the results were surprising. As expected. the anti-p110 antiserum immunoprecipitated p110 from cells transfected with pSG5-p110 (FIG. 15C, lane 3). However, in addition, it would only immunoprecipitate free p110 from lysates prepared from cells co-transfected with p85α and p110 (FIG. 15C, lane 4) even though p85α/p110 complex was present in these lysates (FIG. 15A, lane 4). When assayed for PI3-kinase activity, no activity above that present in control immunoprecipitates (FIG. 15D, lanes 1 and 2), was present in p110 containing immunoprecipitates prepared from either p110 -transfected (FIG. 15D, lane 3) or, p85α and p110 co-transfected, cells (FIG. 15D, lane 4). Thus, the anti-p110 antiserum is capable of immunoprecipitating p110 from cell lysates of both infected Sf9 cells (FIG. 13A, lane 4) and transfected COS-1 cells (FIG. 15C, lane 3), but only the immunoprecipitates prepared from Sf9 cell lysates possess elevated levels of PI3-kinase activity (compare FIG. 13B, lane 4 and FIG. 15D, lane 3). Also, the anti-p110 antiserum immunoprecipitates the p85α/p110 complex when expressed in Sf9 cells, but not when expressed in COS-1 cells.

As indicated above, analysis of the cloned p110 cDNA shows it to encode a protein of 1068 amino acids with a calculated molecular weight of 124 kD. The reason for the difference in size between the calculated (124 kD) and observed molecular weight value 110 kD is unclear, but it is known that many proteins migrate anomalously on SDS-PAGE gels. Expression of the protein encoded by this ORF in Sf9 cells, COS-1 cells, reticulocyte lysate and E. coli all result in the production of a protein of apparent molecular weight 110 kD.

The deduced amino acid sequence of p110 contains all the peptide sequences determined by protein sequence analysis. Since the peptides were obtained from a lysylendopeptidase digestion, it is expected that they should all be preceded by an arginine residue. This is true in every case, except for peptide A which is preceded by an arginine residue (Arg 162). Nucleotide sequence data obtained from another cDNA clone covering this region confirms the presence of an arginine residue in this position. Thus, it seems likely that cleavage at this site by lysylendopeptidase results from a sequence polymorphism.

When a database search was performed on the p110 sequence no significant homology was detected with any proteins known to be involved in inositol lipid metabolism. However, as noted, p110 did show significant homology throughout its C-terminal half to the Saccharomyces cerevisiae protein Vps34p. The possibility that Vps34p is a yeast PI-kinase is currently being investigated. If p110 and Vps34p are homologous proteins then it is interesting to speculate that p110 might also be involved with protein targeting and/or vesicular transport. PI3-kinase activity has previously been implicated in vesicle mediated responses in higher eukaryotes. Hence, PI3-kinase activity is seen to increase following stimulation of platelets with thrombin (Kucera and Rittenhouse, 1990) and neutrophils with f-Met-Leu-Phe (Traynor-Kaplan et al, 1988). In both cases, ligand stimulation promotes the fusion of vesicular structures necessary for the biological response. A role for PI3-kinase in intracellular vesicles following the activation of PTKs has also been suggested (Cantley et al, 1991; Kelly et al, 1992).

Southern blotting data suggests there may be two genes for PI3-kinase in rats and humans. Evidence for the existence of a second gene in rat DNA is also provided by the results of Carpenter et al., (1990), who identified two forms of p110 in their purified PI3-kinase preparation. In situ hybridization confirms the presence of two closely related sequences in human DNA, although one could be a pseudogene. Two forms of p85 (p85α and p85β) have been characterized (Otsu et al, 1991), although only p85α is found associated with p110 in PI3-kinase from bovine brain. It is possible to speculate that p85β associates with a second form of p110.

Although, at present, the function of the 3-phosphorylated phosphoinositides produced by PI3-kinase is unclear, the availability of expression systems which allow their generation will aid in the determination of their function.

EXAMPLE 2

Using the bovine cDNA probe constituted by the XbaI-PstI fragment of the sequence of FIG. 9 (probe a, bottom panel) and genomic DNAs from several species, Southern blot analyses prove positive against the bovine probe in the following species: bovine (calf thymus), human (HeLa cells), rat (liver), simian (COS cells), porcine (ZNR cells), chicken (from Promega), and Xenopus (liver).

The human cDNA was isolated from a cDNA library, made from mRNA isolated from the human cell line KG1a using standard techniques. The probe was a partial cDNA from the second half of the bovine p110 cDNA. The probe was labelled with $^{32}P$ and hybridised overnight to the library filters at 65° C. in 1M NaPi, 7% SDS buffer. The filters were washed in 2×SSC at 50° C., and exposed to X-ray film at −70° C. The nucleotide sequence is shown in FIG. 16 together with the corresponding amino acid sequence. The human p110 sequence has 95% homology to the bovine p110 sequence at the DNA level and is 98% identical at the protein level (FIGS. 17 and 18). The protein sequence is shown in FIG. 19. Primers (357) AAG GAT CAG AAC AAT GCC T (SEQ ID NO:24) and (416) AGG CTT TCT TTA GCC ATC A (SEQ ID NO:25) were used to amplify, using RT-PCR (94° C. 30 sec 50° C. 30 sec, 72° C. 60 secs; for 35 cycles) the partial sequence of a highly related p110 gene (p110-11). P110-11 has 96% nucleotide homology to p110 (sequence not provided).

Two novel cDNAs related to p110 have been cloned. Degenerate primers were designed to conserved sequences between human p110 and the related yeast gene VPS34 (Sense (GDDLRQD) (SEQ ID NO:26) 5' GGN GAT/C GAT/C T/C TA/G CGN CAA/G GA-3' (SEQ ID NO:27) antisense (FHIDFGHF) (SEQ ID NO:28) 5'A/GAA A/GTG ICC A/GAA A/GTC A/G/TAT A/GTG A/GAA-3') (SEQ ID NO:29). These were used in RT-PCR reactions using mRNA from the human cell lines MOLT4 and U937 (94° C. 30 sec, 50° C. 30 sec, 72° C. 30 sec for 35 cycles). [Two novel cDNA's, PITR-c and PITR-f, related to p110, were isolted.] The PITR-c nucleotide sequence is shown in FIG. 20. This gene is highly related to the yeast gene VPS34, the VPS34 protein is involved in the protein sorting from the golgi to the vacuole and has an intrinsic PI3-kinase activity. The PITR-f nucleotide sequence is shown in FIG. 21 and is more similar to p110 than PITR-c and is likely also to possess PI3-kinase activity. The alignment of human p110, the human PI3-kinase related genes PITR-c and PITR-f and the yeast PI3-kinase VPS34 are shown in FIG. 22. The amino acids conserved in 3 or more of the proteins are shown in the upper case.

The interation of the p85 and p110 subunits of PI3-kinase are thought to be required for the activity of the kinase in mammalian cells. Thus inhibiting the interaction between the subunits could provide a means of inhibiting the activity of this signal transduction pathway. In order to design reagents to p110 which will block the interaction, it is useful to define the region of p110 which binds to the p85 subunits. To do this a series of mutants were constructed which express various domains of the p110 protein (FIG. 23B). These fragments were expressed as GST fusion proteins in bacteria. The proteins were then bound to a glutathione sepharose coluirn (Pharmicia) according to the manufacturer's instructions (Panayotou G et al (1992) EmboJ 11:4261–4272). The ability of these protein fragments to bind the p85 subunits was assessed by the ability of the column specifically to retain p85 subunits purified from baculovirus (Otsu et al(1991) Cell 65:91–104). As shown in FIG. 23A, only p110-N (αα1–128) was capable of binding the p85α and β subunits. To further characterise the binding domain, deletion mutants and PCR fragments were made from the p110-N fragment as shown in FIG. 24. The results in FIG. 25 demonstrate that a domain containing amino acids 19–110 of human p110 is sufficient to associate with the p85 subunits. Removal of a further 20 amino acids from either the amino or carboxy termini led to loss of binding activity. Now that this domain has been identified it allows the design of specific peptides, antibodies or small molecules which can inhibit the interaction between the subunits.

The invention includes a human PI3-kinase p110 subunit sequence comprising amino acids 19 to 110 of human p110, or an amino terminal truncated or carboxy terminal truncated derivative thereof having less than 20 amino acids deleted from the amino terminal or carboxy terminal end, respectively, but which is capable of binding to a PI3-kinase p85 subunit; and also included is a method of inhibiting p85 and p110 mammalian PI3-kinase subunit interaction, which comprises utilizing a molecule which blocks the binding domain located between amino acids 19 and 110 of human p110.

The invention further provides the use of a sequence or derivative as defined above in screening for a therapeutic or prophylactic agent which operates by inhibiting interaction between p85 and p110 mammalian PI3-kinase subunits.

References

Anderson, D et al., (1990), Science 250, 979–982.
Ashmum, R A et al., (1989), Blood 73, 827–837.
Auger, K R et al., (1989), J. Biol. Chem. 264, 20181–20184.
Auger, K R et al., (1991), Cancer Cells 3, 263–270.
Berridge, M J et al., (1989), Nature 341, 197–205.
Bjorge, J D et al., (1990), Proc. Natl. Acad. Sci. USA 87,, 3816–3820.
Cantley, L C et al., (1991), Cell 64, 281–302.
Carpenter, C L et al., (1990), Biochemistry 29, 11147–11156.
Carpenter, C L et al., (1990), J. Biol. Chem. 265, 19704–19711.
Chan, T O et al., (1990), Mol. Cell. Biol. 10, 3280–3283.
Chirgwin, J M et al., (1979), Biochemistry 18, 294–299.
Cohen, B et al., (1990), Mol. Cell. Biol. 10, 2909–2915.
Cooper, J A et al., (1983), Methods Enzymol. 99, 387–402.
Coughlin, S R et al., (1989), Science 243, 1191–1194.
Courtneidge, S A et al., (1987), Cell 50, 1031–1037.
Devereux, J et al., (1984), Nucleic Acids Res. 12, 387–395.
Downes, C P et al., (1990), Eur. J. Biochem. 193, 1–18.
Downes, C P et al., (1991), Cellular Signalling 3, 501–513.

Enderman, G et al., (1987), Biochemistry 26, 6845–6852.
Escobedo, J A et al., (1988), Nature 335, 85–87.
Escobedo, J A et al., (1991a), Mol. Cell. Biol. 11, 1125–1132.
Escobedo, J A et al., (1991b), Cell 65, 75–82.
Frohman, M A et al., (1988), Proc. Nat. Acad. Sci. USA 85, 8998–9002.
Fukui, Y et al., (1989), Mol. Cell. Biol. 9, 1651–1658.
Graziani, A et al., (1991), J. Biol. Chem. 266, 22087–22090.
Hanks, S K et al., (1988), Science 241, 42–52.
Hanks, S K (1991), Current Opinion in Structural Biology 1, 369–383.
Harvey, R J et al., (1991), Nuc. Acids. Res. 19, 4002.
Henikoff, S (1984), Gene 28, 351–359.
Herman, P K et al., (1990), Mol. Cell. Biol. 10, 6742–6754.
Hu, P et al., (1992), Mol. Cell. Biol. 12, 981–990.
Kaplan, D R et al., (1986), Proc. Natl. Acad. Sci. USA 83, 3624–3628.
Kaplan, D R et al., (1987), Cell 50, 1021–1029.
Kaplan, D R et al., (1990), Cell 61, 125–133.
Kaufman, R J et al., (1989), Mol. Cell. Biol. 9, 946–958.
Kawasaki, H et al., (1990), Anal. Biochem. 186, 264–268.
Kazlauskas, A et al., (1989), Cell 58, 1121–1133.
Kazlauskas, A et al., (1990), EMBO J. 9, 3279–3286.
Kazlauskas, A et al., (1990), Science 247, 1578–1581.
Kazlauskas, A et al., (1991), Cell Regulation 2, 413–425.
Kelly, K L et al., (1992), J. Biol. Chem. 267, 3423–3428.
Kemp, B E et al., (1990), TIBS 15, 342–346.
Knighton, D R et al., (1991a), Science 253, 407–414.
Knighton, D R et al., (1991b), Science 253, 414–420.
Koch, C A et al., (1991), Science 252, 668–674.
Kozak, M (1987), Nucl. Acids Res. 15, 8125–8148.
Kucera, G L et al., (1990), J. Biol. Chem. 265, 5345–5348.
Kypta, R M et al., (1988), EMBO J. 7, 3837–3844.
Kypta, R M et al., (1990), Cell 62, 481–492.
Lev, S et al., (1991), EMBO J. 10, 647–654.
Lips, D L (1989), J. Biol. Chem. 264, 8759–8763.
Majerus, P W et al., (1990), Cell 63, 459–465.
Maniatis, T et al., (1982) Molecular Cloning: a laboratory manual (Cold Spring Harbor Laboratory).
Margolis, B et al., (1990), EMBO J. 9, 4375–4380.
Matsuda, M et al., (1991), Mol. Cell. Biol. 11, 1607–1613.
Mayer, B J et al., (1990), Proc. Natl. Acad. Sci. USA 87, 2638–2642.
Mayer, B J et al., (1991), Proc. Natl. Acad. Sci. USA 88, 627–631.
Meisenhelder, J et al., (1989), Cell 57, 1109–1122.
McGlade, C J et al., (1992), Mol. Cell. Biol. 12, 991–997.
Moran, M F et al., (1990), Proc. Natl. Acad. Sci. USA 87, 8622–8626.
Morgan, S J et al., (1990), Eur. J. Biochem. 191, 761–767.
Morrison, D K et al., (1989), Cell 58, 649–657.
Otsu, M et al., (1991), Cell 65, 91–104.
Page, M J (1989), Nucl. Acids Res. 17, 454.
Pendergast, A M et al., (1991), Cell 66, 161–171.
Rhee, S G (1991), Trends Biochem. Sci. 16, 297–301.
Rigby, P W J et al.,(1977), I. J. Mol. Biol. 113, 237–251.
Robinson, J S et al., (1988), Mol. Cell. Biol. 8, 4936–4948.
Ruderman, N B et al., (1990), Proc. Natl. Acad. Sci. USA 87, 1411–1415.
Saraste, M et al., (1990), Trends Biochem. Sci. 15, 430–434.
Serunian, L A et al., (1989), J. Biol. Chem. 264, 17809–17815.
Shurtleff, S A et al., (1990), EMBO J. 9, 2415–2421.
Shibasaki, F et al., (1991), J. Biol. Chem. 266, 8108–8114.
Skolnik, E Y et al., (1991), Cell 65, 83–90.
Shurtleff, S A et al., (1990), EMBO J. 9, 2415–2421.
Stephens, L R et al., (1991), Nature 351, 33–39.
Summers, M D et al., (1987), A Manual of Methods for Baculovirus Insect Vectors and Insect Cell Culture Procedures;
Texas Agri. Exp. Station Bull. No 1555.
Talmage, D A et al., (1989), Cell 59, 55–65.
Thom D, et al., (1977), Biochem. J. 168, 187–194.
Traynor-Kaplan, A E et al., (1988), Nature 334, 353–356
Ullrich, A et al., (1990), Cell 61, 203–212.
Ulug, E T et al., (1990), J. Virol. 64, 3895–3904.
Varticovski, L et al., (1989), Nature 342, 699–702.
Varticovski, L et al., (1991), Mol. Cell. Biol. 11, 1107–1113.
Whitley, G S J et al., (1987), Mol. Cell. Endocrinol. 52, 279–284.
Whitman, M et al., (1985), Nature 315, 239–242.
Whitman, M et al., (1987), Biochem. J. 247, 165–174.
Whitman, M et al., (1988), Biochem. Biophys. Acta. 948, 327–344.
Whitman, M et al., (1988), Nature 332, 644–646.
Woodgett, J R (1989), Anal. Biochem. 180, 237–241.
Yanisch-Perron, C et al., (1985), Gene 33, 103–119.
Yu, J C et al., (1991), Mol. Cell. Biol. 11, 3780–3785.

We claim:

1. An isolated nucleic acid molecule which encodes the catalytic (110 kD) subunit of PI-3 kinase, selected from the group consisting of:
    (a) the nucleotide sequence set forth in SEQ ID NO: 32,
    (b) the nucleotide sequence set forth in SEQ ID NO: 35, and
    (c) a nucleotide sequence which hybridizes to the complement of at least one of (a) and (b).

2. The isolated nucleic acid molecule of claim 1, wherein said isolated nucleic acid molecule encodes a polypeptide consisting of the amino acid sequence encoded by the nucleotide sequence set forth in SEQ ID NO: 32 SEQ ID NO: 35.

3. The isolated nucleic acid molecule of claim 1, wherein said isolated nucleic acid molecule encodes a polypeptide consisting of the amino acid sequence set forth in SEQ ID NO: 37.

4. Expression vector comprising the isolated nucleic acid molecule of claim 2, operably linked to a promoter.

5. The expression vector of claim 4, wherein said promoter is regulatable.

6. Host cell transformed or transfected with the expression vector of claim 4.

7. The host cell of claim 6, wherein said host cell is an insect cell.

8. Isolated nucleic acid molecule consisting of any one of
    (a) nucleotides 487–525 of SEQ ID NO: 32,
    (b) nucleotides 876–1011 of SEQ ID NO: 32,
    (c) nucleotides 1321–1392 of SEQ ID NO: 32,
    (d) nucleotides 1864–1944 of SEQ ID NO: 32,
    (e) nucleotides 1969–2016 of SEQ ID NO: 32,
    (f) nucleotides 2035–2097 of SEQ ID NO: 32,
    (g) nucleotides 2134–2160 of SEQ ID NO: 32,
    (h) nucleotides 2602–2646 of SEQ ID NO: 32,
    (i) nucleotides 2653–2724 of SEQ ID NO: 32,
    (j) nucleotides 2773–2823 of SEQ ID NO: 32,
    (k) nucleotides 2845–2898 of SEQ ID NO: 32,
    (l) nucleotides 2959–3030 of SEQ ID NO: 32,
    (m) nucleotides 3091–3189 of SEQ ID NO: 32, and
    (n) nucleotides 3163–3189 of SEQ ID NO: 32.

* * * * *

UNITED STATES PATENT AND TRADEMARK OFFICE
CERTIFICATE OF CORRECTION

PATENT NO. : 5,846,824
DATED : Dec. 8, 1998
INVENTOR(S) : Hiles et al.

It is certified that error appears in the above-identified patent and that said Letters Patent is hereby corrected as shown below:

column 2, line 11, change "p850B" to -- p85$\beta$ --.
column 19, line 26, change "MRNA" to -- mRNA --.
column 19, line 26, change "CDNA" to -- cDNA --.
column 21, line 13, change "rtth" to -- rTth --.
column 23, line 40, change "aminic" to -- amino --.
column 28, line 12, change "coluirn" to -- column --.

Signed and Sealed this

Twenty-fourth Day of October, 2000

Attest:

Q. TODD DICKINSON

*Attesting Officer*              *Director of Patents and Trademarks*

SEQUENCE LISTING ( 1 ) GENERAL INFORMATION:

( i i i ) NUMBER OF SEQUENCES: 50

( 2 ) INFORMATION FOR SEQ ID NO: 1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO: 1:

Gly  Glu  Ser  Asp  Gly  Gly  Tyr  Met  Asp  Met  Ser  Lys
    1                     5                                         1 0

( 2 ) INFORMATION FOR SEQ ID NO: 2:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( x i ) SEQUENCE DESCRIPTION: SEQ ID NO: 2:

```
Asp Met Ser Lys Asp Glu Ser Val Asp Tyr Val Pro Met Leu Asp Met
1               5                   10                  15
Lys
```

( 2 ) INFORMATION FOR SEQ ID NO: 3:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO: 3:

```
Cys Asp Glu Ser Val Asp Tyr Val Pro Met Leu
1               5                   10
```

( 2 ) INFORMATION FOR SEQ ID NO: 4:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO: 4:

```
Ala Arg Asp Ile Met Arg Asp Ser Asn Tyr Ile Ser Lys Gly Ser Thr
1               5                   10                  15
Phe
```

( 2 ) INFORMATION FOR SEQ ID NO: 5:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( x i ) SEQUENCE DESCRIPTION: SEQ ID NO: 5:

```
Glu Phe Cys Pro Asp Pro Leu Tyr Glu Val Met Leu Lys
1               5                   10
```

( 2 ) INFORMATION FOR SEQ ID NO: 6:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO: 6:

```
Arg Arg Phe Thr Ser Thr Glu Pro Gln Tyr Gln Pro Gly Glu Asn Leu
1               5                   10                  15
```

( 2 ) INFORMATION FOR SEQ ID NO: 7:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( x i ) SEQUENCE DESCRIPTION: SEQ ID NO: 7:

Arg Arg Leu Ile Glu Asp Asn Glu Tyr Thr Ala Arg Gly
1               5                           10

( 2 ) INFORMATION FOR SEQ ID NO: 8:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO: 8:

Thr Leu Ala Tyr Pro Val Tyr Ala Gln Gln Arg Arg
1               5                       10

( 2 ) INFORMATION FOR SEQ ID NO: 9:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO: 9:

Thr Leu Ala His Pro Val Arg Ala Pro Gly Pro Gly Pro Pro Ala Ala
1               5                   10                      15

Arg ( 2 ) INFORMATION FOR SEQ ID NO: 10:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO: 10:

Tyr Xaa Xaa Met
1

( 2 ) INFORMATION FOR SEQ ID NO: 11:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO: 11:

Met Asp Trp Ile Phe His Thr
1               5

( 2 ) INFORMATION FOR SEQ ID NO: 12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

AARATGGAYT GGATHTTYCA YAC                                    2 3

( 2 ) INFORMATION FOR SEQ ID NO: 13:

( i ) SEQUENCE CHARACTERISTICS:

(A) LENGTH: 13 amino acids
        (B) TYPE: amino acid
        (C) STRANDEDNESS: single
        (D) TOPOLOGY: linear (xi) SEQUENCE DESCRIPTION: SEQ ID NO: 13:

Asp Asp Gly Gln Leu Phe His Ile Asp Phe Gly His Phe
    1               5                   10

(2) INFORMATION FOR SEQ ID NO: 14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 14:

GATGATGGCC ARCTGTTYCA YATWGAYTTT GGCCA                                35

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 15:

AATTCACACA CTGGCATGCC GAT                                             23

(2) INFORMATION FOR SEQ ID NO: 16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 16:

GACTCGAGTC GACATCGATT TTTTTTTTT TTTTT                                 35

(2) INFORMATION FOR SEQ ID NO: 17:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 17:

TTTAAGCTTA GGCATTCTAA AGTCACTATC ATCCC                                35

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 18:

GACTCGAGTC GACATCGA                                                   18

(2) INFORMATION FOR SEQ ID NO: 19:

(i) SEQUENCE CHARACTERISTICS:
        (A) LENGTH: 17 base pairs (B) TYPE: nucleic acid
(C) STRANDEDNESS: single
(D) TOPOLOGY: linear (xi) SEQUENCE DESCRIPTION: SEQ ID NO: 19:

CAGGCCTGGC TTCCTGT    17

(2) INFORMATION FOR SEQ ID NO: 20:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 20:

AACCAGGCTC AACTGTT    17

(2) INFORMATION FOR SEQ ID NO: 21:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 21:

TGCTGTAAAT TCTAATGCTG    20

(2) INFORMATION FOR SEQ ID NO: 22:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 22:

GTATTTCATG AAACAAATGA    20

(2) INFORMATION FOR SEQ ID NO: 23:

(i) SEQUENCE CHARACTERISTICS:
(A) LENGTH: 16 amino acids
(B) TYPE: amino acid
(C) STRANDEDNESS: single
(D) TOPOLOGY: linear (xi) SEQUENCE DESCRIPTION: SEQ ID NO: 23:

Cys Lys Met Asp Trp Ile Phe His Thr Ile Lys Gln His Ala Leu Asn
1               5                   10                  15

(2) INFORMATION FOR SEQ ID NO: 24:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO: 24:

AAGGATCAGA ACAATGCCT    19

(2) INFORMATION FOR SEQ ID NO: 25:

(i) SEQUENCE CHARACTERISTICS:
(A) LENGTH: 19 base pairs
(B) TYPE: nucleic acid ( C ) STRANDEDNESS: single
( D ) TOPOLOGY: linear ( x i ) SEQUENCE DESCRIPTION: SEQ ID NO: 25:

AGGCTTTCTT TAGCCATCA 19

( 2 ) INFORMATION FOR SEQ ID NO: 26:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( x i ) SEQUENCE DESCRIPTION: SEQ ID NO: 26:

Gly Asp Asp Leu Arg Gln Asp
1               5

( 2 ) INFORMATION FOR SEQ ID NO: 27:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO: 27:

GGNGAYGAYY TRCGNCARGA 20

( 2 ) INFORMATION FOR SEQ ID NO: 28:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( x i ) SEQUENCE DESCRIPTION: SEQ ID NO: 28:

Phe His Ile Asp Phe Gly His Phe
1               5

( 2 ) INFORMATION FOR SEQ ID NO: 29:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO: 29:

RAARTGCCRA ARTCDATRTG RAA 23

( 2 ) INFORMATION FOR SEQ ID NO: 30:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( x i ) SEQUENCE DESCRIPTION: SEQ ID NO: 30:

Glu Glu Glu Glu Glu Tyr Met Pro Met Xaa Xaa
1               5                       10

( 2 ) INFORMATION FOR SEQ ID NO: 31:

( i ) SEQUENCE CHARACTERISTICS:
( A ) LENGTH: 6 amino acids (B) TYPE: amino acid
(C) STRANDEDNESS: single
(D) TOPOLOGY: linear (xi) SEQUENCE DESCRIPTION: SEQ ID NO: 31:

Asp Asp Asp Asp Asp Val
1               5

(2) INFORMATION FOR SEQ ID NO: 32:

(i) SEQUENCE CHARACTERISTICS:
(A) LENGTH: 3412 base pairs
(B) TYPE: nucleic acid
(C) STRANDEDNESS: single or double
(D) TOPOLOGY: linear (ix) FEATURE:
(A) NAME/KEY: CDS
(B) LOCATION: 1..3204
(D) OTHER INFORMATION: /standard_name= "CDS"

(xi) SEQUENCE DESCRIPTION: SEQ ID NO: 32:

| ATG | CCT | CCA | AGA | CCA | TCA | TCA | GGT | GAA | CTG | TGG | GGC | ATC | CAC | TTG | ATG | 48 |
| Met | Pro | Pro | Arg | Pro | Ser | Ser | Gly | Glu | Leu | Trp | Gly | Ile | His | Leu | Met | |
| 1 | | | | 5 | | | | | 10 | | | | | 15 | | |

| CCC | CCA | AGA | ATC | CTA | GTG | GAA | TGT | TTA | CTA | CCA | AAT | GGA | ATG | ATA | GTG | 96 |
| Pro | Pro | Arg | Ile | Leu | Val | Glu | Cys | Leu | Leu | Pro | Asn | Gly | Met | Ile | Val | |
| | | | 20 | | | | | 25 | | | | | 30 | | | |

| ACT | TTA | GAA | TGC | CTC | CGT | GAG | GCT | ACA | TTA | GTA | ACT | ATA | AAG | CAT | GAA | 144 |
| Thr | Leu | Glu | Cys | Leu | Arg | Glu | Ala | Thr | Leu | Val | Thr | Ile | Lys | His | Glu | |
| | | 35 | | | | | 40 | | | | | 45 | | | | |

| CTA | TTT | AAA | GAA | GCA | AGA | AAA | TAC | CCT | CTC | CAT | CAA | CTT | CTT | CAA | GAT | 192 |
| Leu | Phe | Lys | Glu | Ala | Arg | Lys | Tyr | Pro | Leu | His | Gln | Leu | Leu | Gln | Asp | |
| | 50 | | | | | 55 | | | | | 60 | | | | | |

| GAA | TCT | TCT | TAC | ATT | TTC | GTA | AGT | GTT | ACC | CAA | GAA | GCA | GAA | AGG | GAA | 240 |
| Glu | Ser | Ser | Tyr | Ile | Phe | Val | Ser | Val | Thr | Gln | Glu | Ala | Glu | Arg | Glu | |
| 65 | | | | | 70 | | | | | 75 | | | | | 80 | |

| GAA | TTT | TTT | GAT | GAA | ACA | AGA | CGA | CTT | TGT | GAT | CTT | CGG | CTT | TTT | CAA | 288 |
| Glu | Phe | Phe | Asp | Glu | Thr | Arg | Arg | Leu | Cys | Asp | Leu | Arg | Leu | Phe | Gln | |
| | | | | 85 | | | | | 90 | | | | | 95 | | |

| CCA | TTT | TTA | AAA | GTA | ATT | GAA | CCA | GTA | GGC | AAC | CGT | GAA | GAA | AAG | ATC | 336 |
| Pro | Phe | Leu | Lys | Val | Ile | Glu | Pro | Val | Gly | Asn | Arg | Glu | Glu | Lys | Ile | |
| | | | 100 | | | | | 105 | | | | | 110 | | | |

| CTC | AAT | CGA | GAA | ATT | GGT | TTT | GCT | ATC | GGC | ATG | CCA | GTG | TGC | GAA | TTT | 384 |
| Leu | Asn | Arg | Glu | Ile | Gly | Phe | Ala | Ile | Gly | Met | Pro | Val | Cys | Glu | Phe | |
| | | 115 | | | | | 120 | | | | | 125 | | | | |

| GAT | ATG | GTT | AAA | GAT | CCT | GAA | GTA | CAG | GAC | TTC | CGA | AGA | AAT | ATT | CTT | 432 |
| Asp | Met | Val | Lys | Asp | Pro | Glu | Val | Gln | Asp | Phe | Arg | Arg | Asn | Ile | Leu | |
| | 130 | | | | | 135 | | | | | 140 | | | | | |

| AAT | GTT | TGT | AAA | GAA | GCT | GTG | GAT | CTT | AGG | GAT | CTT | AAT | TCA | CCT | CAT | 480 |
| Asn | Val | Cys | Lys | Glu | Ala | Val | Asp | Leu | Arg | Asp | Leu | Asn | Ser | Pro | His | |
| 145 | | | | | 150 | | | | | 155 | | | | | 160 | |

| AGT | AGA | GCA | ATG | TAT | GTC | TAT | CCG | CCA | CAT | GTA | GAA | TCT | TCA | CCA | GAG | 528 |
| Ser | Arg | Ala | Met | Tyr | Val | Tyr | Pro | Pro | His | Val | Glu | Ser | Ser | Pro | Glu | |
| | | | | 165 | | | | | 170 | | | | | 175 | | |

| CTG | CCA | AAG | CAC | ATA | TAT | AAT | AAA | TTG | GAT | AGA | GGC | CAA | ATA | ATA | GTG | 576 |
| Leu | Pro | Lys | His | Ile | Tyr | Asn | Lys | Leu | Asp | Arg | Gly | Gln | Ile | Ile | Val | |
| | | | 180 | | | | | 185 | | | | | 190 | | | |

| GTG | ATT | TGG | GTA | ATA | GTT | TCT | CCA | AAT | AAT | GAC | AAG | CAG | AAG | TAT | ACT | 624 |
| Val | Ile | Trp | Val | Ile | Val | Ser | Pro | Asn | Asn | Asp | Lys | Gln | Lys | Tyr | Thr | |
| | | 195 | | | | | 200 | | | | | 205 | | | | |

| CTG | AAA | ATC | AAC | CAT | GAC | TGT | GTG | CCA | GAA | CAA | GTA | ATT | GCT | GAA | GCA | 672 |
| Leu | Lys | Ile | Asn | His | Asp | Cys | Val | Pro | Glu | Gln | Val | Ile | Ala | Glu | Ala | |
| | 210 | | | | | 215 | | | | | 220 | | | | | |

-continued

| | | | | | | | | | | | | | | | | |
|---|---|---|---|---|---|---|---|---|---|---|---|---|---|---|---|---|
| ATC | AGG | AAA | AAA | ACT | AGA | AGT | ATG | TTG | CTA | TCA | TCT | GAA | CAA | TTA | AAA | 720 |
| Ile | Arg | Lys | Lys | Thr | Arg | Ser | Met | Leu | Leu | Ser | Ser | Glu | Gln | Leu | Lys | |
| 225 | | | | 230 | | | | | 235 | | | | | 240 | | |
| CTC | TGT | GTT | TTA | GAA | TAT | CAG | GGC | AAG | TAC | ATT | TTA | AAA | GTG | TGT | GGA | 768 |
| Leu | Cys | Val | Leu | Glu | Tyr | Gln | Gly | Lys | Tyr | Ile | Leu | Lys | Val | Cys | Gly | |
| | | | | 245 | | | | | 250 | | | | | 255 | | |
| TGT | GAT | GAA | TAC | TTC | CTA | GAA | AAA | TAT | CCT | CTG | AGT | CAG | TAT | AAG | TAT | 816 |
| Cys | Asp | Glu | Tyr | Phe | Leu | Glu | Lys | Tyr | Pro | Leu | Ser | Gln | Tyr | Lys | Tyr | |
| | | | 260 | | | | | 265 | | | | | 270 | | | |
| ATA | AGA | AGC | TGT | ATA | ATG | CTT | GGG | AGG | ATG | CCC | AAT | TTG | AAG | ATG | ATG | 864 |
| Ile | Arg | Ser | Cys | Ile | Met | Leu | Gly | Arg | Met | Pro | Asn | Leu | Lys | Met | Met | |
| | | 275 | | | | | 280 | | | | | 285 | | | | |
| GCT | AAA | GAA | AGC | CTT | TAT | TCT | CAA | CTG | CCA | ATG | GAC | TGT | TTT | ACA | ATG | 912 |
| Ala | Lys | Glu | Ser | Leu | Tyr | Ser | Gln | Leu | Pro | Met | Asp | Cys | Phe | Thr | Met | |
| 290 | | | | | 295 | | | | | 300 | | | | | | |
| CCA | TCT | TAT | TCC | AGA | CGC | ATT | TCC | ACA | GCT | ACA | CCA | TAT | ATG | AAT | GGA | 960 |
| Pro | Ser | Tyr | Ser | Arg | Arg | Ile | Ser | Thr | Ala | Thr | Pro | Tyr | Met | Asn | Gly | |
| 305 | | | | | 310 | | | | | 315 | | | | | 320 | |
| GAA | ACA | TCT | ACA | AAA | TCC | CTT | TGG | GTT | ATA | AAT | AGA | GCA | CTC | AGA | ATA | 1008 |
| Glu | Thr | Ser | Thr | Lys | Ser | Leu | Trp | Val | Ile | Asn | Arg | Ala | Leu | Arg | Ile | |
| | | | | 325 | | | | | 330 | | | | | 335 | | |
| AAA | ATT | CTT | TGT | GCA | ACC | TAC | GTG | AAT | CTA | AAT | ATT | CGA | GAC | ATT | GAC | 1056 |
| Lys | Ile | Leu | Cys | Ala | Thr | Tyr | Val | Asn | Leu | Asn | Ile | Arg | Asp | Ile | Asp | |
| | | | 340 | | | | | 345 | | | | | 350 | | | |
| AAG | ATT | TAT | GTT | CGA | ACA | GGT | ATC | TAC | CAT | GGA | GGA | GAA | CCC | TTA | TGT | 1104 |
| Lys | Ile | Tyr | Val | Arg | Thr | Gly | Ile | Tyr | His | Gly | Gly | Glu | Pro | Leu | Cys | |
| | | 355 | | | | | 360 | | | | | 365 | | | | |
| GAC | AAT | GTG | AAC | ACT | CAA | AGA | GTA | CCT | TGT | TCC | AAT | CCC | AGG | TGG | AAT | 1152 |
| Asp | Asn | Val | Asn | Thr | Gln | Arg | Val | Pro | Cys | Ser | Asn | Pro | Arg | Trp | Asn | |
| 370 | | | | | 375 | | | | | 380 | | | | | | |
| GAA | TGG | CTG | AAT | TAT | GAT | ATA | TAC | ATT | CCT | GAT | CTT | CCT | CGT | GCT | GCT | 1200 |
| Glu | Trp | Leu | Asn | Tyr | Asp | Ile | Tyr | Ile | Pro | Asp | Leu | Pro | Arg | Ala | Ala | |
| 385 | | | | | 390 | | | | | 395 | | | | | 400 | |
| CGA | CTT | TGC | CTT | TCC | ATT | TGC | TCT | GTT | AAA | GGC | CGA | AAG | GGT | GCT | AAA | 1248 |
| Arg | Leu | Cys | Leu | Ser | Ile | Cys | Ser | Val | Lys | Gly | Arg | Lys | Gly | Ala | Lys | |
| | | | | 405 | | | | | 410 | | | | | 415 | | |
| GAG | GAA | CAC | TGT | CCA | TTG | GCA | TGG | GGA | AAT | ATA | AAC | TTG | TTT | GAT | TAC | 1296 |
| Glu | Glu | His | Cys | Pro | Leu | Ala | Trp | Gly | Asn | Ile | Asn | Leu | Phe | Asp | Tyr | |
| | | | 420 | | | | | 425 | | | | | 430 | | | |
| ACA | GAC | ACT | CTA | GTA | TCT | GGA | AAA | ATG | GCT | TTG | AAT | CTT | TGG | CCA | GTA | 1344 |
| Thr | Asp | Thr | Leu | Val | Ser | Gly | Lys | Met | Ala | Leu | Asn | Leu | Trp | Pro | Val | |
| | | 435 | | | | | 440 | | | | | 445 | | | | |
| CCT | CAT | GGA | TTA | GAA | GAT | TTG | CTG | AAC | CCT | ATT | GGT | GTT | ACT | GGA | TCA | 1392 |
| Pro | His | Gly | Leu | Glu | Asp | Leu | Leu | Asn | Pro | Ile | Gly | Val | Thr | Gly | Ser | |
| 450 | | | | | 455 | | | | | 460 | | | | | | |
| AAT | CCA | AAT | AAA | GAA | ACT | CCA | TGC | TTA | GAG | TTG | GAG | TTT | GAC | TGG | TTC | 1440 |
| Asn | Pro | Asn | Lys | Glu | Thr | Pro | Cys | Leu | Glu | Leu | Glu | Phe | Asp | Trp | Phe | |
| 465 | | | | | 470 | | | | | 475 | | | | | 480 | |
| AGC | AGT | GTG | GTA | AAG | TTC | CCA | GAT | ATG | TCA | GTG | ATT | GAA | GAG | CAT | GCC | 1488 |
| Ser | Ser | Val | Val | Lys | Phe | Pro | Asp | Met | Ser | Val | Ile | Glu | Glu | His | Ala | |
| | | | | 485 | | | | | 490 | | | | | 495 | | |
| AAT | TGG | TCT | GTA | TCC | CGA | GAA | GCA | GGA | TTT | AGC | TAT | TCC | CAC | GCA | GGA | 1536 |
| Asn | Trp | Ser | Val | Ser | Arg | Glu | Ala | Gly | Phe | Ser | Tyr | Ser | His | Ala | Gly | |
| | | | 500 | | | | | 505 | | | | | 510 | | | |
| CTG | AGT | AAC | AGA | CTA | GCT | AGA | GAC | AAT | GAA | TTA | AGG | GAA | AAT | GAC | AAA | 1584 |
| Leu | Ser | Asn | Arg | Leu | Ala | Arg | Asp | Asn | Glu | Leu | Arg | Glu | Asn | Asp | Lys | |
| | | 515 | | | | | 520 | | | | | 525 | | | | |
| GAA | CAG | CTC | AAA | GCA | ATT | TCT | ACA | CGA | GAT | CCT | CTC | TCT | GAA | ATC | ACT | 1632 |
| Glu | Gln | Leu | Lys | Ala | Ile | Ser | Thr | Arg | Asp | Pro | Leu | Ser | Glu | Ile | Thr | |
| | 530 | | | | | 535 | | | | | 540 | | | | | |

| | | | | | | | | | | | | | | | | |
|---|---|---|---|---|---|---|---|---|---|---|---|---|---|---|---|---|
| GAG | CAG | GAG | AAA | GAT | TTT | CTA | TGG | AGT | CAC | AGA | CAC | TAT | TGT | GTA | ACT | 1680 |
| Glu | Gln | Glu | Lys | Asp | Phe | Leu | Trp | Ser | His | Arg | His | Tyr | Cys | Val | Thr | |
| 545 | | | | | 550 | | | | | 555 | | | | | 560 | |
| ATC | CCC | GAA | ATT | CTA | CCC | AAA | TTG | CTT | CTG | TCT | GTT | AAA | TGG | AAT | TCT | 1728 |
| Ile | Pro | Glu | Ile | Leu | Pro | Lys | Leu | Leu | Leu | Ser | Val | Lys | Trp | Asn | Ser | |
| | | | | 565 | | | | | 570 | | | | | 575 | | |
| AGA | GAT | GAA | GTA | GCC | CAG | ATG | TAT | TGC | TTG | GTA | AAA | GAT | TGG | CCT | CCA | 1776 |
| Arg | Asp | Glu | Val | Ala | Gln | Met | Tyr | Cys | Leu | Val | Lys | Asp | Trp | Pro | Pro | |
| | | | 580 | | | | | 585 | | | | | 590 | | | |
| ATC | AAA | CCT | GAA | CAG | GCT | ATG | GAA | CTT | CTG | GAC | TGT | AAT | TAC | CCA | GAT | 1824 |
| Ile | Lys | Pro | Glu | Gln | Ala | Met | Glu | Leu | Leu | Asp | Cys | Asn | Tyr | Pro | Asp | |
| | | 595 | | | | | 600 | | | | | 605 | | | | |
| CCT | ATG | GTT | CGA | GGT | TTT | GCT | GTT | CGG | TGC | TTG | GAA | AAA | TAT | TTA | ACA | 1872 |
| Pro | Met | Val | Arg | Gly | Phe | Ala | Val | Arg | Cys | Leu | Glu | Lys | Tyr | Leu | Thr | |
| | 610 | | | | | 615 | | | | | 620 | | | | | |
| GAT | GAC | AAA | CTT | TCT | CAG | TAT | TTA | ATT | CAG | CTA | GTA | CAG | GTC | CTA | AAA | 1920 |
| Asp | Asp | Lys | Leu | Ser | Gln | Tyr | Leu | Ile | Gln | Leu | Val | Gln | Val | Leu | Lys | |
| 625 | | | | | 630 | | | | | 635 | | | | | 640 | |
| TAT | GAA | CAA | TAT | TTG | GAT | AAC | TTG | CTT | GTG | AGA | TTT | TTA | CTG | AAG | AAA | 1968 |
| Tyr | Glu | Gln | Tyr | Leu | Asp | Asn | Leu | Leu | Val | Arg | Phe | Leu | Leu | Lys | Lys | |
| | | | | 645 | | | | | 650 | | | | | 655 | | |
| GCA | TTG | ACT | AAT | CAA | AGG | ATT | GGG | CAC | TTT | TTC | TTT | TGG | CAT | TTA | AAA | 2016 |
| Ala | Leu | Thr | Asn | Gln | Arg | Ile | Gly | His | Phe | Phe | Phe | Trp | His | Leu | Lys | |
| | | | 660 | | | | | 665 | | | | | 670 | | | |
| TCT | GAG | ATG | CAC | AAT | AAA | ACA | GTT | AGC | CAG | AGG | TTT | GGC | CTG | CTT | TTG | 2064 |
| Ser | Glu | Met | His | Asn | Lys | Thr | Val | Ser | Gln | Arg | Phe | Gly | Leu | Leu | Leu | |
| | | 675 | | | | | 680 | | | | | 685 | | | | |
| GAG | TCC | TAT | TGT | CGT | GCA | TGT | GGG | ATG | TAT | TTG | AAG | CAC | CTG | AAT | AGG | 2112 |
| Glu | Ser | Tyr | Cys | Arg | Ala | Cys | Gly | Met | Tyr | Leu | Lys | His | Leu | Asn | Arg | |
| | 690 | | | | | 695 | | | | | 700 | | | | | |
| CAA | GTC | GAG | GCA | ATG | GAA | AAG | CTC | ATT | AAC | TTA | ACT | GAC | ATT | CTC | AAA | 2160 |
| Gln | Val | Glu | Ala | Met | Glu | Lys | Leu | Ile | Asn | Leu | Thr | Asp | Ile | Leu | Lys | |
| 705 | | | | | 710 | | | | | 715 | | | | | 720 | |
| CAG | GAG | AGG | AAG | GAT | GAA | ACA | CAA | AAG | GTA | CAG | ATG | AAG | TTT | TTA | GTT | 2208 |
| Gln | Glu | Arg | Lys | Asp | Glu | Thr | Gln | Lys | Val | Gln | Met | Lys | Phe | Leu | Val | |
| | | | | 725 | | | | | 730 | | | | | 735 | | |
| GAG | CAA | ATG | AGG | CGA | CCA | GAT | TTC | ATG | GAT | GCC | CTA | CAG | GGC | TTG | CTG | 2256 |
| Glu | Gln | Met | Arg | Arg | Pro | Asp | Phe | Met | Asp | Ala | Leu | Gln | Gly | Leu | Leu | |
| | | | 740 | | | | | 745 | | | | | 750 | | | |
| TCT | CCT | CTA | AAC | CCT | GCT | CAT | CAA | CTA | GGA | AAC | CTC | AGG | CTT | AAA | GAG | 2304 |
| Ser | Pro | Leu | Asn | Pro | Ala | His | Gln | Leu | Gly | Asn | Leu | Arg | Leu | Lys | Glu | |
| | | 755 | | | | | 760 | | | | | 765 | | | | |
| TGT | CGA | ATT | ATG | TCT | TCT | GCA | AAA | AGG | CCA | CTG | TGG | TTG | AAT | TGG | GAG | 2352 |
| Cys | Arg | Ile | Met | Ser | Ser | Ala | Lys | Arg | Pro | Leu | Trp | Leu | Asn | Trp | Glu | |
| | 770 | | | | | 775 | | | | | 780 | | | | | |
| AAC | CCA | GAC | ATC | ATG | TCA | GAG | TTA | CTG | TTT | CAG | AAC | AAT | GAG | ATC | ATC | 2400 |
| Asn | Pro | Asp | Ile | Met | Ser | Glu | Leu | Leu | Phe | Gln | Asn | Asn | Glu | Ile | Ile | |
| 785 | | | | | 790 | | | | | 795 | | | | | 800 | |
| TTT | AAA | AAT | GGG | GAT | GAT | TTA | CGG | CAA | GAT | ATG | CTA | ACA | CTT | CAA | ATT | 2448 |
| Phe | Lys | Asn | Gly | Asp | Asp | Leu | Arg | Gln | Asp | Met | Leu | Thr | Leu | Gln | Ile | |
| | | | | 805 | | | | | 810 | | | | | 815 | | |
| ATT | CGT | ATT | ATG | GAA | AAT | ATC | TGG | CAA | AAT | CAA | GGT | CTT | GAT | CTT | CGA | 2496 |
| Ile | Arg | Ile | Met | Glu | Asn | Ile | Trp | Gln | Asn | Gln | Gly | Leu | Asp | Leu | Arg | |
| | | | 820 | | | | | 825 | | | | | 830 | | | |
| ATG | TTA | CCT | TAT | GGT | TGT | CTG | TCA | ATC | GGT | GAC | TGT | GTG | GGA | CTT | ATT | 2544 |
| Met | Leu | Pro | Tyr | Gly | Cys | Leu | Ser | Ile | Gly | Asp | Cys | Val | Gly | Leu | Ile | |
| | | 835 | | | | | 840 | | | | | 845 | | | | |
| GAG | GTG | GTG | CGA | AAT | TCT | CAC | ACT | ATT | ATG | CAA | ATT | CAG | TGC | AAA | GGC | 2592 |
| Glu | Val | Val | Arg | Asn | Ser | His | Thr | Ile | Met | Gln | Ile | Gln | Cys | Lys | Gly | |
| | 850 | | | | | 855 | | | | | 860 | | | | | |

```
GGC  TTG  AAA  GGT  GCA  CTG  CAG  TTC  AAC  AGC  CAC  ACA  CTA  CAT  CAG  TGG                2640
Gly  Leu  Lys  Gly  Ala  Leu  Gln  Phe  Asn  Ser  His  Thr  Leu  His  Gln  Trp
865                      870                      875                      880

CTC  AAA  GAC  AAG  AAC  AAA  GGA  GAA  ATA  TAT  GAT  GCA  GCC  ATT  GAC  CTG                2688
Leu  Lys  Asp  Lys  Asn  Lys  Gly  Glu  Ile  Tyr  Asp  Ala  Ala  Ile  Asp  Leu
                         885                      890                      895

TTT  ACA  CGT  TCA  TGT  GCT  GGA  TAC  TGT  GTA  GCT  ACC  TTC  ATT  TTG  GGA                2736
Phe  Thr  Arg  Ser  Cys  Ala  Gly  Tyr  Cys  Val  Ala  Thr  Phe  Ile  Leu  Gly
            900                      905                      910

ATT  GGA  GAT  CGT  CAC  AAT  AGT  AAC  ATC  ATG  GTG  AAA  GAC  GAT  GGA  CAA                2784
Ile  Gly  Asp  Arg  His  Asn  Ser  Asn  Ile  Met  Val  Lys  Asp  Asp  Gly  Gln
                 915                      920                      925

CTG  TTT  CAT  ATA  GAT  TTT  GGA  CAC  TTT  TTG  GAT  CAC  AAG  AAG  AAA  AAA                2832
Leu  Phe  His  Ile  Asp  Phe  Gly  His  Phe  Leu  Asp  His  Lys  Lys  Lys  Lys
930                      935                      940

TTT  GGT  TAT  AAA  CGA  GAA  CGT  GTG  CCA  TTT  GTT  TTG  ACA  CAG  GAT  TTC                2880
Phe  Gly  Tyr  Lys  Arg  Glu  Arg  Val  Pro  Phe  Val  Leu  Thr  Gln  Asp  Phe
945                      950                      955                      960

TTA  ATA  GTG  ATT  AGT  AAA  GGA  GCC  CAA  GAA  TGC  ACA  AAG  ACA  AGA  GAA                2928
Leu  Ile  Val  Ile  Ser  Lys  Gly  Ala  Gln  Glu  Cys  Thr  Lys  Thr  Arg  Glu
                 965                      970                      975

TTT  GAG  AGG  TTT  CAG  GAG  ATG  TGT  TAC  AAG  GCT  TAT  CTA  GCT  ATT  CGA                2976
Phe  Glu  Arg  Phe  Gln  Glu  Met  Cys  Tyr  Lys  Ala  Tyr  Leu  Ala  Ile  Arg
            980                      985                      990

CAG  CAT  GCC  AAT  CTC  TTC  ATA  AAT  CTT  TTC  TCA  ATG  ATG  CTT  GGC  TCT                3024
Gln  His  Ala  Asn  Leu  Phe  Ile  Asn  Leu  Phe  Ser  Met  Met  Leu  Gly  Ser
       995                      1000                     1005

GGA  ATG  CCA  GAA  CTA  CAA  TCT  TTT  GAT  GAC  ATT  GCA  TAC  ATT  CGA  AAG                3072
Gly  Met  Pro  Glu  Leu  Gln  Ser  Phe  Asp  Asp  Ile  Ala  Tyr  Ile  Arg  Lys
1010                     1015                     1020

ACC  CTA  GCC  TTA  GAT  AAA  ACT  GAG  CAA  GAG  GCT  TTG  GAG  TAT  TTC  ATG                3120
Thr  Leu  Ala  Leu  Asp  Lys  Thr  Glu  Gln  Glu  Ala  Leu  Glu  Tyr  Phe  Met
1025                     1030                     1035                     1040

AAA  CAA  ATG  AAT  GAT  GCA  CAT  CAT  GGT  GGC  TGG  ACA  ACA  AAA  ATG  GAT                3168
Lys  Gln  Met  Asn  Asp  Ala  His  His  Gly  Gly  Trp  Thr  Thr  Lys  Met  Asp
                         1045                     1050                     1055

TGG  ATC  TTC  CAC  ACA  ATT  AAA  CAG  CAT  GCA  TTG  AAC  TGAAAGATAA                         3214
Trp  Ile  Phe  His  Thr  Ile  Lys  Gln  His  Ala  Leu  Asn
                 1060                     1065

CTGAGAAAAT  GAAAGCTCAC  TCTGGACACT  ACACTGCACT  GTTAATAACT  CTCAGCAGGC                         3274

AAAGACCGAT  TGCATAGGAA  TTGCACAATC  CATGAACAGC  ATTAGATTTA  CAGCAAGAAC                         3334

AGAAATAAAA  TACTATATAA  TTTAAATAAT  GTAAACGCAA  ACAGGGTTTG  ATAGCACTTA                         3394

AACTAGTTCA  TTTCAAAA                                                                           3412
```

( 2 ) INFORMATION FOR SEQ ID NO: 33:

( i ) SEQUENCE CHARACTERISTICS:
        ( A ) LENGTH: 868 amino acids residues
        ( B ) TYPE: amino acid
        ( C ) STRANDEDNESS: single
        ( D ) TOPOLOGY: linear ( x i ) SEQUENCE DESCRIPTION: SEQ ID NO: 33:

```
Asn  Ile  Thr  Phe  Cys  Val  Ser  Gln  Asp  Leu  Asp  Val  Pro  Leu  Lys  Val
1                   5                        10                       15

Lys  Ile  Lys  Ser  Leu  Glu  Gly  His  Lys  Pro  Leu  Leu  Lys  Pro  Ser  Gln
               20                       25                       30

Lys  Ile  Leu  Asn  Pro  Glu  Leu  Met  Leu  Ile  Gly  Ser  Asn  Val  Phe  Pro
               35                       40                       45
```

```
Ser  Ser  Asp  Leu  Ile  Val  Ser  Leu  Gln  Val  Phe  Asp  Lys  Glu  Arg  Asn
     50                       55                      60

Arg  Asn  Leu  Thr  Leu  Pro  Ile  Tyr  Thr  Pro  Tyr  Ile  Pro  Phe  Arg  Asn
65                       70                      75                           80

Ser  Arg  Thr  Trp  Asp  Tyr  Trp  Leu  Thr  Leu  Pro  Ile  Arg  Ile  Lys  Gln
               85                       90                                95

Leu  Thr  Phe  Ser  Ser  His  Leu  Arg  Ile  Ile  Leu  Trp  Glu  Tyr  Asn  Gly
               100                      105                     110

Ser  Lys  Gln  Ile  Pro  Phe  Phe  Asn  Leu  Glu  Thr  Ser  Ile  Phe  Asn  Leu
               115                      120                     125

Lys  Asp  Cys  Thr  Leu  Lys  Arg  Gly  Phe  Glu  Ser  Leu  Lys  Phe  Arg  Tyr
     130                      135                     140

Asp  Val  Ile  Asp  His  Cys  Glu  Val  Val  Thr  Asp  Asn  Lys  Asp  Gln  Glu
145                      150                     155                         160

Asn  Leu  Asn  Lys  Tyr  Phe  Gln  Gly  Glu  Phe  Thr  Arg  Leu  Pro  Trp  Leu
                    165                      170                     175

Asp  Glu  Ile  Thr  Ile  Ser  Lys  Leu  Arg  Lys  Gln  Arg  Glu  Asn  Arg  Thr
               180                      185                     190

Trp  Pro  Gln  Gly  Thr  Phe  Val  Leu  Asn  Leu  Glu  Phe  Pro  Met  Leu  Glu
               195                      200                     205

Leu  Pro  Val  Val  Phe  Ile  Glu  Arg  Glu  Ile  Met  Asn  Thr  Gln  Met  Asn
     210                      215                     220

Ile  Pro  Thr  Leu  Lys  Asn  Asn  Pro  Gly  Leu  Ser  Thr  Asp  Leu  Arg  Glu
225                      230                     235                         240

Pro  Asn  Arg  Asn  Asp  Pro  Gln  Ile  Lys  Ile  Ser  Leu  Gly  Asp  Lys  Tyr
                    245                      250                     255

His  Ser  Thr  Leu  Lys  Phe  Tyr  Asp  Pro  Asp  Gln  Pro  Asn  Asn  Asp  Pro
               260                      265                     270

Ile  Glu  Glu  Lys  Tyr  Arg  Arg  Leu  Glu  Arg  Ala  Ser  Lys  Asn  Ala  Asn
               275                      280                     285

Leu  Asp  Lys  Gln  Val  Lys  Pro  Asp  Ile  Lys  Lys  Arg  Asp  Tyr  Leu  Asn
     290                      295                     300

Lys  Ile  Ile  Asn  Tyr  Pro  Pro  Gly  Thr  Lys  Leu  Thr  Ala  His  Glu  Lys
305                      310                     315                         320

Gly  Ser  Ile  Trp  Lys  Tyr  Arg  Tyr  Tyr  Leu  Met  Asn  Asn  Lys  Lys  Ala
                    325                      330                     335

Leu  Thr  Lys  Leu  Leu  Gln  Ser  Thr  Asn  Leu  Arg  Glu  Glu  Ser  Glu  Arg
               340                      345                     350

Val  Glu  Val  Leu  Glu  Leu  Met  Asp  Ser  Trp  Ala  Glu  Ile  Asp  Ile  Asp
               355                      360                     365

Asp  Ala  Leu  Glu  Leu  Leu  Gly  Ser  Thr  Phe  Lys  Asn  Leu  Ser  Val  Arg
     370                      375                     380

Ser  Tyr  Ala  Val  Asn  Arg  Leu  Lys  Lys  Ala  Ser  Asp  Lys  Glu  Leu  Glu
385                      390                     395                         400

Leu  Tyr  Leu  Leu  Gln  Leu  Val  Glu  Ala  Val  Cys  Phe  Glu  Asn  Leu  Ser
                    405                      410                     415

Thr  Phe  Ser  Asp  Lys  Ser  Asn  Ser  Glu  Phe  Thr  Ile  Val  Asp  Ala  Val
               420                      425                     430

Ser  Ser  Gln  Lys  Leu  Ser  Gly  Asp  Ser  Met  Leu  Leu  Ser  Thr  Ser  His
               435                      440                     445

Ala  Asn  Gln  Lys  Leu  Leu  Lys  Ser  Ile  Ser  Ser  Glu  Ser  Glu  Thr  Ser
     450                      455                     460

Gly  Thr  Glu  Ser  Leu  Pro  Ile  Val  Ile  Ser  Pro  Leu  Ala  Glu  Phe  Leu
```

```
465                     470                     475                     480
Ile  Arg  Arg  Ala  Leu  Val  Asn  Pro  Arg  Leu  Gly  Ser  Phe  Phe  Tyr  Trp
                    485                     490                     495

Tyr  Leu  Lys  Ser  Glu  Ser  Glu  Asp  Lys  Pro  Tyr  Leu  Asp  Gln  Ile  Leu
                    500                     505                     510

Ser  Ser  Phe  Trp  Ser  Arg  Leu  Asp  Lys  Lys  Ser  Arg  Asn  Ile  Leu  Asn
               515                     520                     525

Asp  Gln  Val  Arg  Leu  Ile  Asn  Val  Leu  Arg  Glu  Cys  Cys  Glu  Thr  Ile
          530                     535                     540

Lys  Arg  Leu  Lys  Asp  Thr  Thr  Ala  Lys  Lys  Met  Glu  Leu  Leu  Val  His
545                     550                     555                     560

Leu  Leu  Glu  Thr  Lys  Val  Arg  Pro  Leu  Val  Lys  Val  Arg  Pro  Ile  Ala
                    565                     570                     575

Leu  Pro  Leu  Asp  Pro  Asp  Val  Leu  Ile  Cys  Asp  Val  Cys  Pro  Glu  Thr
               580                     585                     590

Ser  Lys  Val  Phe  Lys  Ser  Ser  Leu  Ser  Pro  Leu  Lys  Ile  Thr  Phe  Lys
          595                     600                     605

Thr  Thr  Leu  Asn  Gln  Pro  Tyr  His  Leu  Met  Phe  Lys  Val  Gly  Asp  Asp
     610                     615                     620

Leu  Arg  Gln  Asp  Gln  Leu  Val  Val  Gln  Ile  Ile  Ser  Leu  Met  Asn  Glu
625                     630                     635                     640

Leu  Leu  Lys  Asn  Glu  Asn  Val  Asp  Leu  Lys  Leu  Thr  Pro  Tyr  Lys  Ile
                    645                     650                     655

Leu  Ala  Thr  Gly  Pro  Gln  Glu  Gly  Ala  Ile  Glu  Phe  Ile  Pro  Asn  Asp
               660                     665                     670

Thr  Leu  Ala  Ser  Ile  Leu  Ser  Lys  Tyr  His  Gly  Ile  Leu  Gly  Tyr  Leu
          675                     680                     685

Lys  Leu  His  Tyr  Pro  Asp  Glu  Asn  Ala  Thr  Leu  Gly  Val  Gln  Gly  Trp
690                     695                     700

Val  Leu  Asp  Asn  Phe  Val  Lys  Ser  Cys  Ala  Gly  Tyr  Cys  Val  Ile  Thr
705                     710                     715                     720

Tyr  Ile  Leu  Gly  Val  Gly  Asp  Arg  His  Leu  Asp  Asn  Leu  Leu  Val  Thr
                    725                     730                     735

Pro  Asp  Gly  His  Phe  Phe  His  Ala  Asp  Phe  Gly  Tyr  Ile  Leu  Gly  Gln
               740                     745                     750

Asp  Pro  Lys  Pro  Phe  Pro  Pro  Leu  Met  Lys  Leu  Pro  Pro  Gln  Ile  Ile
          755                     760                     765

Glu  Ala  Phe  Gly  Gly  Ala  Glu  Ser  Ser  Asn  Tyr  Asp  Lys  Phe  Arg  Ser
770                     775                     780

Tyr  Cys  Phe  Val  Ala  Tyr  Ser  Ile  Leu  Arg  Arg  Asn  Ala  Gly  Leu  Ile
785                     790                     795                     800

Leu  Asn  Leu  Phe  Glu  Leu  Met  Lys  Thr  Ser  Asn  Ile  Pro  Asp  Ile  Arg
                    805                     810                     815

Ile  Asp  Pro  Asn  Gly  Ala  Ile  Leu  Arg  Val  Arg  Glu  Arg  Phe  Asn  Leu
               820                     825                     830

Asn  Met  Ser  Glu  Glu  Asp  Ala  Thr  Val  His  Phe  Gln  Asn  Leu  Ile  Asn
          835                     840                     845

Asp  Ser  Val  Asn  Ala  Leu  Leu  Pro  Ile  Val  Ile  Asp  His  Leu  His  Asn
     850                     855                     860

Leu  Ala  Gln  Tyr
865
```

( 2 ) INFORMATION FOR SEQ ID NO: 34:

( i ) SEQUENCE CHARACTERISTICS:
    ( A ) LENGTH: 3240 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 34:

| | | | | | |
|---|---|---|---|---|---|
| ATGCCTCCAA | GACCATCATC | AGGTGAACTG | TGGGGCATCC | ACTTGATGCC | CCCAAGAATC | 60 |
| CTAGTGGAAT | GTTTACTACC | AAATGGAATG | ATAGTGACTT | TAGAATGCCT | CCGTGAGGCT | 120 |
| ACATTAGTAA | CTATAAAGCA | TGAACTATTT | AAAGAAGCAA | GAAAATACCC | TCTCCATCAA | 180 |
| CTTCTTCAAG | ATGAATCTTC | TTACATTTTC | GTAAGTGTTA | CCCAAGAAGC | AGAAAGGGAA | 240 |
| GAATTTTTG | ATGAAACAAG | ACGACTTTGT | GATCTTCGGC | TTTTTCAACC | ATTTTAAAA | 300 |
| GTAATTGAAC | CAGTAGGCAA | CCGTGAAGAA | AAGATCCTCA | ATCGAGAAAT | TGGTTTTGCT | 360 |
| ATCGGCATGC | CAGTGTGCGA | ATTTGATATG | GTTAAAGATC | CTGAAGTACA | GGACTTCCGA | 420 |
| AGAAATATTC | TTAATGTTTG | TAAAGAAGCT | GTGGATCTTA | GGGATCTTAA | TTCACCTCAT | 480 |
| AGTAGAGCAA | TGTATGTCTA | TCCGCCACAT | GTAGAATCTT | CACCAGAGCT | GCCAAAGCAC | 540 |
| ATATATAATA | AATTGGATAG | AGGCCAAATA | ATAGTGGTGA | TTTGGGTAAT | AGTTTCTCCA | 600 |
| AATAATGACA | AGCAGAAGTA | TACTCTGAAA | ATCAACCATG | ACTGTGTGCC | AGAACAAGTA | 660 |
| ATTGCTGAAG | CAATCAGGAA | AAAAACTAGA | AGTATGTTGC | TATCATCTGA | ACAATTAAAA | 720 |
| CTCTGTGTTT | TAGAATATCA | GGGCAAGTAC | ATTTTAAAAG | TGTGTGGATG | TGATGAATAC | 780 |
| TTCCTAGAAA | AATATCCTCT | GAGTCAGTAT | AAGTATATAA | GAAGCTGTAT | AATGCTTGGG | 840 |
| AGGATGCCCA | ATTTGAAGAT | GATGGCTAAA | GAAAGCCTTT | ATTCTCAACT | GCCAATGGAC | 900 |
| TGTTTTACAA | TGCCATCTTA | TTCCAGACGC | ATTTCCACAG | CTACACCATA | TATGAATGGA | 960 |
| GAAACATCTA | CAAAATCCCT | TGGGTTATA | AATAGAGCAC | TCAGAATAAA | AATTCTTTGT | 1020 |
| GCAACCTATG | TGAATGTAAA | TATTCGAGAC | ATTGACAAGA | TTTATGTTCG | AACAGGTATC | 1080 |
| TACCATGGAG | GAGAACCCTT | ATGTGACAAT | GTGAACACTC | AAAGAGTACC | TTGTTCCAAT | 1140 |
| CCCAGGTGGA | ATGAATGGCT | GAATTATGAT | ATATACATTC | CTGATCTTCC | TCGTGCTGCT | 1200 |
| CGACTTTGCC | TTTCCATTTG | CTCTGTTAAA | GGCCGAAAGG | GTGCTAAAGA | GGAACACTGT | 1260 |
| CCATTGGCAT | GGGGAAATAT | AAACTTGTTT | GATTACACAG | ACACTCAGT | ATCTGGAAAA | 1320 |
| ATGGCTTTGA | ATCTTTGGCC | AGTACCTCAT | GGATTAGAAG | ATTTGCTGAA | CCCTATTGGT | 1380 |
| GTTACTGGAT | CAAATCCAAA | TAAAGAAACT | CCATGCTTAG | AGTTGGAGTT | TGACTGGTTC | 1440 |
| AGCAGTGTGG | TAAAGTTCCC | AGATATGTCA | GTGATTGAAG | AGCATGCCAA | TTGGTCTGTA | 1500 |
| TCCCGAGAAG | CAGGATTTAG | CTATTCCAC | GCAGGACTGA | GTAACAGACT | AGCTAGAGAC | 1560 |
| AATGAATTAA | GGGAAAATGA | CAAAGAACAG | CTCAAAGCAA | TTTCTACACG | AGATCCTCTC | 1620 |
| TCTGAAATCA | CTGAGCAGGA | GAAAGATTTT | CTATGGAGTC | ACAGACACTA | TTGTGTAACT | 1680 |
| ATCCCCGAAA | TTCTACCCAA | ATTGCTTCTG | TCTGTTAAAT | GGAATTCTAG | AGATGAAGTA | 1740 |
| GCCCAGATGT | ATTGCTTGGT | AAAAGATTGG | CCTCCAATCA | AACCTGAACA | GGCTATGGAA | 1800 |
| CTTCTGGACT | GTAATTACCC | AGATCCTATG | GTTCGAGGTT | TTGCTGTTCG | GTGCTTGGAA | 1860 |
| AAATATTTAA | CAGATGACAA | ACTTTCTCAG | TATTTAATTC | AGCTAGTACA | GGTCCTAAAA | 1920 |
| TATGAACAAT | ATTTGGATAA | CTTGCTTGTG | AGATTTTAC | TGAAGAAGC | ATTGACTAAT | 1980 |
| CAAAGGATTG | GGCACTTTTT | CTTTTGGCAT | TTAAAATCTG | AGATGCACAA | TAAAACAGTT | 2040 |
| AGCCAGAGGT | TTGGCCTGCT | TTTGGAGTCC | TATTGTCGTG | CATGTGGGAT | GTATTTGAAG | 2100 |
| CACCTGAATA | GGCAAGTCGA | GGCAATGGAA | AAGCTCATTA | ACTTAACTGA | CATTCTCAAA | 2160 |

| | | | | | |
|---|---|---|---|---|---|
| CAGGAGAGGA | AGGATGAAAC | ACAAAAGGTA | CAGATGAAGT | TTTTAGTTGA | GCAAATGAGG | 2220 |
| CGACCAGATT | TCATGGATGC | CCTACAGGGC | TTGCTGTCTC | CTCTAAACCC | TGCTCATCAA | 2280 |
| CTAGGAAACC | TCAGGCTTAA | AGAGTGTCGA | ATTATGTCTT | CTGCAAAAAG | GCCACTGTGG | 2340 |
| TTGAATTGGG | AGAACCCAGA | CATCATGTCA | GAGTTACTGT | TCAGAACAA | TGAGATCATC | 2400 |
| TTTAAAAATG | GGGATGATTT | ACGGCAAGAT | ATGCTAACAC | TTCAAATTAT | TCGTATTATG | 2460 |
| GAAAATATCT | GGCAAAATCA | AGGTCTTGAT | CTTCGAATGT | TACCTTATGG | TTGTCTGTCA | 2520 |
| ATCGGTGACT | GTGTGGGACT | TATTGAGGTG | GTGCGAAATT | CTCACACTAT | TATGCAAATT | 2580 |
| CAGTGCAAAG | GCGGCTTGAA | AGGTGCACTG | CAGTTCAACA | GCCACACACT | ACATCAGTGG | 2640 |
| CTCAAAGACA | AGAACAAAGG | AGAAATATAT | GATGCAGCCA | TTGACCTGTT | TACACGTTCA | 2700 |
| TGTGCTGGAT | ACTGTGTAGC | TACCTTCATT | TTGGGAATTG | GAGATCGTCA | CAATAGTAAC | 2760 |
| ATCATGGTGA | AAGACGATGG | ACAACTGTTT | CATATAGATT | TTGGACACTT | TTTGGATCAC | 2820 |
| AAGAAGAAAA | AATTTGGTTA | TAAACGAGAA | CGTGTGCCAT | TTGTTTTGAC | ACAGGATTTC | 2880 |
| TTAATAGTGA | TTAGTAAAGG | AGCCCAAGAA | TGCACAAAGA | CAAGAGAATT | TGAGAGGTTT | 2940 |
| CAGGAGATGT | GTTACAAGGC | TTATCTAGCT | ATTCGACAGC | ATGCCAATCT | CTTCATAAAT | 3000 |
| CTTTTCTCAA | TGATGCTTGG | CTCTGGAATG | CCAGAACTAC | AATCTTTTGA | TGACATTGCA | 3060 |
| TACATTCGAA | AGACCCTAGC | CTTAGATAAA | ACTGAGCAAG | AGGCTTTGGA | GTATTTCATG | 3120 |
| AAACAAATGA | ATGATGCACA | TCATGGTGGC | TGGACAACAA | AAATGGATTG | GATCTTCCAC | 3180 |
| ACAATTAAAC | AGCATGCATT | GAACTGAAAG | ATAACTGAGA | AAATGAAAGC | TCACTCTGGA | 3240 |

( 2 ) INFORMATION FOR SEQ ID NO: 35:

( i ) SEQUENCE CHARACTERISTICS:
        ( A ) LENGTH: 3207 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 35:

| | | | | | |
|---|---|---|---|---|---|
| ATGCCTCCAA | GACCATCATC | AGGTGAACTG | TGGGGCATCC | ACTTGATGCC | CCCAAGAATC | 60 |
| CTAGTAGAAT | GTTTACTACC | AAATGGGATG | ATAGTGACTT | TAGAATGCCT | CCGTGAGGCT | 120 |
| ACGTTAATAA | CGATAAAGCA | TGAACTATTT | AAAGAAGCAA | GAAAATACCC | TCTCCATCAA | 180 |
| CTTCTTCAAG | ATGAATCTTC | TTACATTTTC | GTAAGTGTTA | CCCAAGAAGC | AGAAAGGGAA | 240 |
| GAATTTTTTG | ATGAAACAAG | ACGACTTTGT | GACCTTCGGC | TTTTTCAACC | CTTTTTAAAA | 300 |
| GTAATTGAAC | CAGTAGGCAA | CCGTGAAGAA | AAGATCCTCA | ATCGAGAAAT | TGGTTTTGCT | 360 |
| ATCGGCATGC | CAGTGTGTGA | ATTCGATATG | GTTAAAGATC | CAGAAGTACA | GGACTTCCGA | 420 |
| AGAAATATTC | TCAATGTTTG | TAAAGAAGCT | GTGGATCTTA | GGGATCTTAA | TTCACCTCAT | 480 |
| AGTAGAGCAA | TGTATGTTTA | TCCTCCAAAT | GTAGAATCTT | CACCAGAACT | GCCAAAGCAC | 540 |
| ATATATAATA | AATTGGATAA | AGGGCAAATA | ATAGTGGTGA | TTTGGGTAAT | AGTTTCTCCA | 600 |
| AATAATGACA | AACAGAAGTA | TACTCTGAAA | ATCAACCATG | ACTGTGTGCC | AGAACAAGTA | 660 |
| ATTGCTGAAG | CAATCAGGAA | AAAAACTCGA | AGTATGTTGC | TATCATCTGA | ACAACTAAAA | 720 |
| CTCTGTGTTT | TAGAATATCA | GGGCAAGTAT | ATTTTAAAAG | TGTGTGGATG | TGATGAATAC | 780 |
| TTCCTAGAAA | AATATCCTCT | GAGTCAGTAT | AAGTATATAA | GAAGCTGTAT | AATGCTTGGG | 840 |
| AGGATGCCCA | ATTTGATGCT | GATGGCTAAA | GAAAGCCTCT | ATTCTCAACT | GCCAATGGAC | 900 |
| TGTTTTACAA | TGCCATCATA | TTCCAGACGC | ATCTCCACAG | CTACGCCATA | TATGAATGGA | 960 |
| GAAACATCTA | CAAAATCCCT | TTGGGTTATA | AATAGTGCAC | TCAGAATAAA | AATTCTTTGT | 1020 |

-continued

```
GCAACCTATG  TGAATGTAAA  TATTCGAGAC  ATTGACAAGA  TTTATGTTCG  AACAGGTATC   1080

TACCATGGAG  GAGAACCCTT  ATGTGATAAT  GTGAACACTC  AAAGAGTACC  TTGTTCCAAT   1140

CCCAGGTGGA  ATGAATGGCT  GAATTACGAT  ATATACATTC  CTGATCTTCC  TCGTGCTGCT   1200

CGACTTTGCC  TTTCCATTTG  TTCTGTTAAA  GGCCGAAAGG  GTGCTAAAGA  GGAACACTGT   1260

CCATTGGCCT  GGGGAAATAT  AAACTTGTTT  GATTACACAG  ATACTCTAGT  ATCTGGAAAA   1320

ATGGCTTTGA  ATCTTTGGCC  AGTACCTCAT  GGACTAGAAG  ATTTGCTGAA  CCCTATTGGT   1380

GTTACTGGAT  CAAATCCAAA  TAAAGAAACT  CCATGTTTAG  AGTTGGAGTT  TGACTGGTTC   1440

AGCAGTGTGG  TAAAGTTTCC  AGATATGTCA  GTGATTGAAG  AGCATGCCAA  TTGGTCTGTA   1500

TCCCGTGAAG  CAGGATTTAG  TTATTCCCAT  GCAGGACTGA  GTAACAGACT  AGCTAGAGAC   1560

AATGAATTAA  GAGAAAATGA  TAAAGAACAG  CTCCGAGCAA  TTTGTACACG  AGATCCTCTA   1620

TCTGAAATCA  CTGAGCAAGA  GAAAGATTTT  CTGTGGAGCC  ACAGACACTA  TTGTGTAACT   1680

ATCCCCGAAA  TTCTACCCAA  ATTGCTTCTG  TCTGTTAAAT  GGAACTCTAG  AGATGAAGTA   1740

GCTCAGATGT  ACTGCTTGGT  AAAAGATTGG  CCTCCAATCA  AGCCTGAACA  GGCTATGGAG   1800

CTTCTGGACT  GCAATTACCC  AGATCCTATG  GTTCGAGGTT  TTGCTGTTCG  GTGCTTAGAA   1860

AAATATTTAA  CAGATGACAA  ACTTTCTCAG  TACCTAATTC  AGCTAGTACA  GGTACTAAAA   1920

TATGAACAGT  ATTTGGATAA  CCTGCTTGTG  AGATTTTTAC  TCAAAAAGC   GTTAACTAAT   1980

CAAAGGATCG  GTCACTTTTT  CTTTTGGCAT  TTAAAATCTG  AGATGCACAA  TAAAACAGTT   2040

AGTCAGAGGT  TTGGCCTGCT  TTTGGAGTCC  TATTGCCGTG  CATGTGGGAT  GTATCTGAAG   2100

CACCTTAATA  GGCAAGTTGA  GGCTATGGAA  AAGCTCATTA  ACTTGACTGA  CATTCTCAAA   2160

CAAGAGAAGA  AGGATGAAAC  ACAAAAGGTA  CAGATGAAGT  TTTTAGTTGA  GCAAATGCGG   2220

CGACCAGATT  TCATGGATGC  TCTCCAGGGC  TTTCTGTCTC  CTCTAAACCC  TGCTCATCAG   2280

CTGGGAAATC  TCAGGCTTGA  AGAGTGTCGA  ATTATGTCTT  CTGCAAAAAG  GCCACTGTGG   2340

TTGAATTGGG  AGAACCCAGA  CATCATGTCA  GAATTACTCT  TTCAGAACAA  TGAGATCATC   2400

TTTAAAAATG  GGGATGATTT  ACGGCAAGAT  ATGCTAACCC  TTCAGATTAT  TCGCATTATG   2460

GAAAATATCT  GGCAAAATCA  AGGTCTTGAT  CTTCGAATGT  TACCTTATGG  ATGTCTGTCA   2520

ATCGGTGACT  GTGTGGGACT  TATCGAGGTG  GTGAGAAATT  CTCACACTAT  AATGCAGATT   2580

CAGTGTAAAG  GAGGCCTGAA  AGGTGCACTG  CAGTTTAACA  GCCACACACT  CCATCAGTGG   2640

CTCAAAGACA  AGAACAAGGG  GGAAATATAT  GATGCGGCCA  TCGATTTGTT  TACACGATCA   2700

TGTGCTGGAT  ATTGTGTTGC  CACCTTCATT  TTGGGAATTG  GAGATCGTCA  CAATAGTAAT   2760

ATCATGGTTA  AAGATGATGG  ACAACTGTTT  CATATAGATT  TTGGACACTT  TTTGGATCAC   2820

AAGAAGAAAA  AATTTGGTTA  TAAACGAGAG  CGCGTGCCGT  TTGTTTTGAC  ACAAGATTTC   2880

TTAATAGTGA  TTAGTAAAGG  AGCCCAAGAA  TGCACAAAGA  CAAGAGAATT  TGAGAGGTTT   2940

CAGGAGATGT  GTTACAAGGC  TTATCTAGCT  ATTCGGCAGC  ATGCCAATCT  CTTCATAAAT   3000

CTTTTCTCAA  TGATGCTTGG  CTCTGGAATG  CCAGAACTGC  AATCTTTTGA  TGATATTGCA   3060

TACATTCGAA  AGACCCTAGC  TTTAGATAAA  ACTGAGCAAG  AGGCTTTGGA  GTATTTCATG   3120

AAACAAATGA  ATGATGCACA  CCATGGTGGC  TGGACAACAA  AAATGGATTG  GATCTTCCAC   3180

ACAATTAAGC  AGCATGCTTT  GAACTGA                                         3207
```

( 2 ) INFORMATION FOR SEQ ID NO: 36:

( i ) SEQUENCE CHARACTERISTICS:

( A ) LENGTH: 1080 amino acids (B) TYPE: amino acid
(C) STRANDEDNESS: single
(D) TOPOLOGY: linear (xi) SEQUENCE DESCRIPTION: SEQ ID NO: 36:

| Met | Pro | Pro | Arg | Pro | Ser | Ser | Gly | Glu | Leu | Trp | Gly | Ile | His | Leu | Met |
|---|---|---|---|---|---|---|---|---|---|---|---|---|---|---|---|
| 1 | | | | 5 | | | | | 10 | | | | | 15 | |
| Pro | Pro | Arg | Ile | Leu | Val | Glu | Cys | Leu | Leu | Pro | Asn | Gly | Met | Ile | Val |
| | | | 20 | | | | 25 | | | | | 30 | | | |
| Thr | Leu | Glu | Cys | Leu | Arg | Glu | Ala | Thr | Leu | Val | Thr | Ile | Lys | His | Glu |
| | | 35 | | | | | 40 | | | | | 45 | | | |
| Leu | Phe | Lys | Glu | Ala | Arg | Lys | Tyr | Pro | Leu | His | Gln | Leu | Leu | Gln | Asp |
| | | 50 | | | | | 55 | | | | 60 | | | | |
| Glu | Ser | Ser | Tyr | Ile | Phe | Val | Ser | Val | Thr | Gln | Glu | Ala | Glu | Arg | Glu |
| 65 | | | | | 70 | | | | | 75 | | | | | 80 |
| Glu | Phe | Phe | Asp | Glu | Thr | Arg | Arg | Leu | Cys | Asp | Leu | Arg | Leu | Phe | Gln |
| | | | | 85 | | | | | 90 | | | | | 95 | |
| Pro | Phe | Leu | Lys | Val | Ile | Glu | Pro | Val | Gly | Asn | Arg | Glu | Glu | Lys | Ile |
| | | | 100 | | | | | 105 | | | | | 110 | | |
| Leu | Asn | Arg | Glu | Ile | Gly | Phe | Ala | Ile | Gly | Met | Pro | Val | Cys | Glu | Phe |
| | | | 115 | | | | | 120 | | | | | 125 | | |
| Asp | Met | Val | Lys | Asp | Pro | Glu | Val | Gln | Asp | Phe | Arg | Arg | Asn | Ile | Leu |
| | | 130 | | | | | 135 | | | | | 140 | | | |
| Asn | Val | Cys | Lys | Glu | Ala | Val | Asp | Leu | Arg | Asp | Leu | Asn | Ser | Pro | His |
| 145 | | | | | 150 | | | | | 155 | | | | | 160 |
| Ser | Arg | Ala | Met | Tyr | Val | Tyr | Pro | Pro | His | Val | Glu | Ser | Ser | Pro | Glu |
| | | | | 165 | | | | | 170 | | | | | 175 | |
| Leu | Pro | Lys | His | Ile | Tyr | Asn | Lys | Leu | Asp | Arg | Gly | Gln | Ile | Ile | Val |
| | | | 180 | | | | | 185 | | | | | 190 | | |
| Val | Ile | Trp | Val | Ile | Val | Ser | Pro | Asn | Asn | Asp | Lys | Gln | Lys | Tyr | Thr |
| | | 195 | | | | | 200 | | | | | 205 | | | |
| Leu | Lys | Ile | Asn | His | Asp | Cys | Val | Pro | Glu | Gln | Val | Ile | Ala | Glu | Ala |
| | 210 | | | | | 215 | | | | | 220 | | | | |
| Ile | Arg | Lys | Lys | Thr | Arg | Ser | Met | Leu | Leu | Ser | Ser | Glu | Gln | Leu | Lys |
| 225 | | | | | 230 | | | | | 235 | | | | | 240 |
| Leu | Cys | Val | Leu | Glu | Tyr | Gln | Gly | Lys | Tyr | Ile | Leu | Lys | Val | Cys | Gly |
| | | | | 245 | | | | | 250 | | | | | 255 | |
| Cys | Asp | Glu | Tyr | Phe | Leu | Glu | Lys | Tyr | Pro | Leu | Ser | Gln | Tyr | Lys | Tyr |
| | | | | 260 | | | | | 265 | | | | | 270 | |
| Ile | Arg | Ser | Cys | Ile | Met | Leu | Gly | Arg | Met | Pro | Asn | Leu | Lys | Met | Met |
| | | 275 | | | | | 280 | | | | | 285 | | | |
| Ala | Lys | Glu | Ser | Leu | Tyr | Ser | Gln | Leu | Pro | Met | Asp | Cys | Phe | Thr | Met |
| | 290 | | | | | 295 | | | | | 300 | | | | |
| Pro | Ser | Tyr | Ser | Arg | Arg | Ile | Ser | Thr | Ala | Thr | Pro | Tyr | Met | Asn | Gly |
| 305 | | | | | 310 | | | | | 315 | | | | | 320 |
| Glu | Thr | Ser | Thr | Lys | Ser | Leu | Trp | Val | Ile | Asn | Arg | Ala | Leu | Arg | Ile |
| | | | | 325 | | | | | 330 | | | | | 335 | |
| Lys | Ile | Leu | Cys | Ala | Thr | Tyr | Val | Asn | Leu | Asn | Ile | Arg | Asp | Ile | Asp |
| | | | | 340 | | | | | 345 | | | | | 350 | |
| Lys | Ile | Tyr | Val | Arg | Thr | Gly | Ile | Tyr | His | Gly | Gly | Glu | Pro | Leu | Cys |
| | | | 355 | | | | | 360 | | | | | 365 | | |
| Asp | Asn | Val | Asn | Thr | Gln | Arg | Val | Pro | Cys | Ser | Asn | Pro | Arg | Trp | Asn |
| | | 370 | | | | | 375 | | | | | 380 | | | |
| Glu | Trp | Leu | Asn | Tyr | Asp | Ile | Tyr | Ile | Pro | Asp | Leu | Pro | Arg | Ala | Ala |
| 385 | | | | | 390 | | | | | 395 | | | | | 400 |

-continued

| | | | | | | | | | | | | | | |
|---|---|---|---|---|---|---|---|---|---|---|---|---|---|---|
| Arg | Leu | Cys | Leu | Ser | Ile | Cys | Ser | Val | Lys | Gly | Arg | Lys | Gly | Ala | Lys |
| | | | | 405 | | | | | 410 | | | | | 415 |
| Glu | Glu | His | Cys | Pro | Leu | Ala | Trp | Gly | Asn | Ile | Asn | Leu | Phe | Asp | Tyr |
| | | | 420 | | | | | 425 | | | | | 430 | | |
| Thr | Asp | Thr | Leu | Val | Ser | Gly | Lys | Met | Ala | Leu | Asn | Leu | Trp | Pro | Val |
| | | 435 | | | | | 440 | | | | | 445 | | | |
| Pro | His | Gly | Leu | Glu | Asp | Leu | Leu | Asn | Pro | Ile | Gly | Val | Thr | Gly | Ser |
| | 450 | | | | | 455 | | | | | 460 | | | | |
| Asn | Pro | Asn | Lys | Glu | Thr | Pro | Cys | Leu | Glu | Leu | Glu | Phe | Asp | Trp | Phe |
| 465 | | | | | 470 | | | | | 475 | | | | | 480 |
| Ser | Ser | Val | Val | Lys | Phe | Pro | Asp | Met | Ser | Val | Ile | Glu | Glu | His | Ala |
| | | | | 485 | | | | | 490 | | | | | 495 | |
| Asn | Trp | Ser | Val | Ser | Arg | Glu | Ala | Gly | Phe | Ser | Tyr | Ser | His | Ala | Gly |
| | | | 500 | | | | | 505 | | | | | 510 | | |
| Leu | Ser | Asn | Arg | Leu | Ala | Arg | Asp | Asn | Glu | Leu | Arg | Glu | Asn | Asp | Lys |
| | | 515 | | | | | 520 | | | | | 525 | | | |
| Glu | Gln | Leu | Lys | Ala | Ile | Ser | Thr | Arg | Asp | Pro | Leu | Ser | Glu | Ile | Thr |
| | 530 | | | | | 535 | | | | | 540 | | | | |
| Glu | Gln | Glu | Lys | Asp | Phe | Leu | Trp | Ser | His | Arg | His | Tyr | Cys | Val | Thr |
| 545 | | | | | 550 | | | | | 555 | | | | | 560 |
| Ile | Pro | Glu | Ile | Leu | Pro | Lys | Leu | Leu | Leu | Ser | Val | Lys | Trp | Asn | Ser |
| | | | | 565 | | | | | 570 | | | | | 575 | |
| Arg | Asp | Glu | Val | Ala | Gln | Met | Tyr | Cys | Leu | Val | Lys | Asp | Trp | Pro | Pro |
| | | | 580 | | | | | 585 | | | | | 590 | | |
| Ile | Lys | Pro | Glu | Gln | Ala | Met | Glu | Leu | Leu | Asp | Cys | Asn | Tyr | Pro | Asp |
| | | 595 | | | | | 600 | | | | | 605 | | | |
| Pro | Met | Val | Arg | Gly | Phe | Ala | Val | Arg | Cys | Leu | Glu | Lys | Tyr | Leu | Thr |
| | 610 | | | | | 615 | | | | | 620 | | | | |
| Asp | Asp | Lys | Leu | Ser | Gln | Tyr | Leu | Ile | Gln | Leu | Val | Gln | Val | Leu | Lys |
| 625 | | | | | 630 | | | | | 635 | | | | | 640 |
| Tyr | Glu | Gln | Tyr | Leu | Asp | Asn | Leu | Leu | Val | Arg | Phe | Leu | Leu | Lys | Lys |
| | | | | 645 | | | | | 650 | | | | | 655 | |
| Ala | Leu | Thr | Asn | Gln | Arg | Ile | Gly | His | Phe | Phe | Phe | Trp | His | Leu | Lys |
| | | | 660 | | | | | 665 | | | | | 670 | | |
| Ser | Glu | Met | His | Asn | Lys | Thr | Val | Ser | Gln | Arg | Phe | Gly | Leu | Leu | Leu |
| | | | 675 | | | | | 680 | | | | | 685 | | |
| Glu | Ser | Tyr | Cys | Arg | Ala | Cys | Gly | Met | Tyr | Leu | Lys | His | Leu | Asn | Arg |
| | | | 690 | | | | | 695 | | | | | 700 | | |
| Gln | Val | Glu | Ala | Met | Glu | Lys | Leu | Ile | Asn | Leu | Thr | Asp | Ile | Leu | Lys |
| 705 | | | | | 710 | | | | | 715 | | | | | 720 |
| Gln | Glu | Arg | Lys | Asp | Glu | Thr | Gln | Lys | Val | Gln | Met | Lys | Phe | Leu | Val |
| | | | | 725 | | | | | 730 | | | | | 735 | |
| Glu | Gln | Met | Arg | Arg | Pro | Asp | Phe | Met | Asp | Ala | Leu | Gln | Gly | Leu | Leu |
| | | | 740 | | | | | 745 | | | | | 750 | | |
| Ser | Pro | Leu | Asn | Pro | Ala | His | Gln | Leu | Gly | Asn | Leu | Arg | Leu | Lys | Glu |
| | | | 755 | | | | | 760 | | | | | 765 | | |
| Cys | Arg | Ile | Met | Ser | Ser | Ala | Lys | Arg | Pro | Leu | Trp | Leu | Asn | Trp | Glu |
| | 770 | | | | | 775 | | | | | 780 | | | | |
| Asn | Pro | Asp | Ile | Met | Ser | Glu | Leu | Leu | Phe | Gln | Asn | Asn | Glu | Ile | Ile |
| 785 | | | | | 790 | | | | | 795 | | | | | 800 |
| Phe | Lys | Asn | Gly | Asp | Asp | Leu | Arg | Gln | Asp | Met | Leu | Thr | Leu | Gln | Ile |
| | | | | 805 | | | | | 810 | | | | | 815 | |
| Ile | Arg | Ile | Met | Glu | Asn | Ile | Trp | Gln | Asn | Gln | Gly | Leu | Asp | Leu | Arg |

|   |   |   |   |   |   |   | 820 |   |   |   |   | 825 |   |   |   |   | 830 |   |   |
|---|---|---|---|---|---|---|---|---|---|---|---|---|---|---|---|---|---|---|---|

Met Leu Pro Tyr Gly Cys Leu Ser Ile Gly Asp Cys Val Gly Leu Ile
        835                  840                  845

Glu Val Val Arg Asn Ser His Thr Ile Met Gln Ile Gln Cys Lys Gly
850                          855                  860

Gly Leu Lys Gly Ala Leu Gln Phe Asn Ser His Thr Leu His Gln Trp
865              870                  875                  880

Leu Lys Asp Lys Asn Lys Gly Glu Ile Tyr Asp Ala Ala Ile Asp Leu
                885                  890                  895

Phe Thr Arg Ser Cys Ala Gly Tyr Cys Val Ala Thr Phe Ile Leu Gly
            900                  905                  910

Ile Gly Asp Arg His Asn Ser Asn Ile Met Val Lys Asp Asp Gly Gln
        915                  920                  925

Leu Phe His Ile Asp Phe Gly His Phe Leu Asp His Lys Lys Lys Lys
930                        935                  940

Phe Gly Tyr Lys Arg Glu Arg Val Pro Phe Val Leu Thr Gln Asp Phe
945              950                955                  960

Leu Ile Val Ile Ser Lys Gly Ala Gln Glu Cys Thr Lys Thr Arg Glu
            965                970                  975

Phe Glu Arg Phe Gln Glu Met Cys Tyr Lys Ala Tyr Leu Ala Ile Arg
        980                  985                  990

Gln His Ala Asn Leu Phe Ile Asn Leu Phe Ser Met Met Leu Gly Ser
        995                  1000               1005

Gly Met Pro Glu Leu Gln Ser Phe Asp Asp Ile Ala Tyr Ile Arg Lys
1010                      1015                1020

Thr Leu Ala Leu Asp Lys Thr Glu Gln Glu Ala Leu Glu Tyr Phe Met
1025                      1030                1035                1040

Lys Gln Met Asn Asp Ala His His Gly Gly Trp Thr Thr Lys Met Asp
                1045                1050                1055

Trp Ile Phe His Thr Ile Lys Gln His Ala Leu Asn Xaa Lys Ile Thr
            1060                1065                1070

Glu Lys Met Lys Ala His Ser Gly
1075                      1080

( 2 ) INFORMATION FOR SEQ ID NO: 37:

( i ) SEQUENCE CHARACTERISTICS:
        ( A ) LENGTH: 1069 amino acids
        ( B ) TYPE: amino acid
        ( C ) STRANDEDNESS: single
        ( D ) TOPOLOGY: linear ( x i ) SEQUENCE DESCRIPTION: SEQ ID NO: 37:

Met Pro Pro Arg Pro Ser Ser Gly Glu Leu Trp Gly Ile His Leu Met
1                    5                    10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
50                    55                  60

Glu Ser Ser Tyr Ile Phe Val Ser Val Thr Gln Glu Ala Glu Arg Glu
65                    70                  75                  80

Glu Phe Phe Asp Glu Thr Arg Arg Leu Cys Asp Leu Arg Leu Phe Gln
              85                  90                  95

Pro Phe Leu Lys Val Ile Glu Pro Val Gly Asn Arg Glu Glu Lys Ile

|     |     |     |     |     |     |     |     |     |     |     |     |     |     |
|---|---|---|---|---|---|---|---|---|---|---|---|---|---|
|     |     |     |     | 100 |     |     |     | 105 |     |     |     | 110 |     |
| Leu | Asn | Arg | Glu | Ile | Gly | Phe | Ala | Ile | Gly | Met | Pro | Val | Cys | Glu | Phe |
|     |     | 115 |     |     |     | 120 |     |     |     | 125 |     |     |     |
| Asp | Met | Val | Lys | Asp | Pro | Glu | Val | Gln | Asp | Phe | Arg | Arg | Asn | Ile | Leu |
|     | 130 |     |     |     | 135 |     |     |     | 140 |     |     |     |     |
| Asn | Val | Cys | Lys | Glu | Ala | Val | Asp | Leu | Arg | Asp | Leu | Asn | Ser | Pro | His |
| 145 |     |     |     | 150 |     |     |     | 155 |     |     |     |     | 160 |
| Ser | Arg | Ala | Met | Tyr | Val | Tyr | Pro | Pro | Asn | Val | Glu | Ser | Ser | Pro | Glu |
|     |     |     | 165 |     |     |     | 170 |     |     |     |     | 175 |
| Leu | Pro | Lys | His | Ile | Tyr | Asn | Lys | Leu | Asp | Lys | Gly | Gln | Ile | Ile | Val |
|     |     |     | 180 |     |     |     | 185 |     |     |     |     | 190 |
| Val | Ile | Trp | Val | Ile | Val | Ser | Pro | Asn | Asn | Asp | Lys | Gln | Lys | Tyr | Thr |
|     |     | 195 |     |     |     | 200 |     |     |     | 205 |     |     |     |
| Leu | Lys | Ile | Asn | His | Asp | Cys | Val | Pro | Glu | Gln | Val | Ile | Ala | Glu | Ala |
|     | 210 |     |     |     | 215 |     |     |     | 220 |     |     |     |     |
| Ile | Arg | Lys | Lys | Thr | Arg | Ser | Met | Leu | Leu | Ser | Ser | Glu | Gln | Leu | Lys |
| 225 |     |     |     | 230 |     |     |     | 235 |     |     |     |     | 240 |
| Leu | Cys | Val | Leu | Glu | Tyr | Gln | Gly | Lys | Tyr | Ile | Leu | Lys | Val | Cys | Gly |
|     |     |     |     | 245 |     |     |     | 250 |     |     |     | 255 |
| Cys | Asp | Glu | Tyr | Phe | Leu | Glu | Lys | Tyr | Pro | Leu | Ser | Gln | Tyr | Lys | Tyr |
|     |     |     | 260 |     |     |     | 265 |     |     |     | 270 |
| Ile | Arg | Ser | Cys | Ile | Met | Leu | Gly | Arg | Met | Pro | Asn | Leu | Met | Leu | Met |
|     |     | 275 |     |     |     | 280 |     |     |     | 285 |     |     |
| Ala | Lys | Glu | Ser | Leu | Tyr | Ser | Gln | Leu | Pro | Met | Asp | Cys | Phe | Thr | Met |
|     | 290 |     |     |     | 295 |     |     |     | 300 |     |     |     |
| Pro | Ser | Tyr | Ser | Arg | Arg | Ile | Ser | Thr | Ala | Thr | Pro | Tyr | Met | Asn | Gly |
| 305 |     |     |     | 310 |     |     |     | 315 |     |     |     |     | 320 |
| Glu | Thr | Ser | Thr | Lys | Ser | Leu | Trp | Val | Ile | Asn | Ser | Ala | Leu | Arg | Ile |
|     |     |     | 325 |     |     |     | 330 |     |     |     | 335 |     |     |
| Lys | Ile | Leu | Cys | Ala | Thr | Tyr | Val | Asn | Val | Asn | Ile | Arg | Asp | Ile | Asp |
|     |     |     | 340 |     |     |     | 345 |     |     |     | 350 |     |     |
| Lys | Ile | Tyr | Val | Arg | Thr | Gly | Ile | Tyr | His | Gly | Gly | Glu | Pro | Leu | Cys |
|     |     | 355 |     |     |     | 360 |     |     |     | 365 |     |     |
| Asp | Asn | Val | Asn | Thr | Gln | Arg | Val | Pro | Cys | Ser | Asn | Pro | Arg | Trp | Asn |
|     | 370 |     |     |     | 375 |     |     |     | 380 |     |     |     |     |
| Glu | Trp | Leu | Asn | Tyr | Asp | Ile | Tyr | Ile | Pro | Asp | Leu | Pro | Arg | Ala | Ala |
| 385 |     |     |     | 390 |     |     |     | 395 |     |     |     |     | 400 |
| Arg | Leu | Cys | Leu | Ser | Ile | Cys | Ser | Val | Lys | Gly | Arg | Lys | Gly | Ala | Lys |
|     |     |     | 405 |     |     |     | 410 |     |     |     | 415 |
| Glu | Glu | His | Cys | Pro | Leu | Ala | Trp | Gly | Asn | Ile | Asn | Leu | Phe | Asp | Tyr |
|     |     |     | 420 |     |     |     | 425 |     |     |     | 430 |
| Thr | Asp | Thr | Leu | Val | Ser | Gly | Lys | Met | Ala | Leu | Asn | Leu | Trp | Pro | Val |
|     |     | 435 |     |     |     | 440 |     |     |     | 445 |
| Pro | His | Gly | Leu | Glu | Asp | Leu | Leu | Asn | Pro | Ile | Gly | Val | Thr | Gly | Ser |
|     | 450 |     |     |     | 455 |     |     |     | 460 |     |     |     |
| Asn | Pro | Asn | Lys | Glu | Thr | Pro | Cys | Leu | Glu | Leu | Glu | Phe | Asp | Trp | Phe |
| 465 |     |     |     | 470 |     |     |     | 475 |     |     |     |     | 480 |
| Ser | Ser | Val | Val | Lys | Phe | Pro | Asp | Met | Ser | Val | Ile | Glu | Glu | His | Ala |
|     |     |     | 485 |     |     |     | 490 |     |     |     | 495 |
| Asn | Trp | Ser | Val | Ser | Arg | Glu | Ala | Gly | Phe | Ser | Tyr | Ser | His | Ala | Gly |
|     |     | 500 |     |     |     | 505 |     |     |     | 510 |
| Leu | Ser | Asn | Arg | Leu | Ala | Arg | Asp | Asn | Glu | Leu | Arg | Glu | Asn | Asp | Lys |
|     |     | 515 |     |     |     | 520 |     |     |     | 525 |

-continued

| | | | | | | | | | | | | | | |
|---|---|---|---|---|---|---|---|---|---|---|---|---|---|---|
| Glu | Gln | Leu | Arg | Ala | Ile | Cys | Thr | Arg | Asp | Pro | Leu | Ser | Glu | Ile | Thr |
| | 530 | | | | 535 | | | | | 540 | | | | |
| Glu | Gln | Glu | Lys | Asp | Phe | Leu | Trp | Ser | His | Arg | His | Tyr | Cys | Val | Thr |
| 545 | | | | | 550 | | | | 555 | | | | | 560 |
| Ile | Pro | Glu | Ile | Leu | Pro | Lys | Leu | Leu | Leu | Ser | Val | Lys | Trp | Asn | Ser |
| | | | | 565 | | | | | 570 | | | | | 575 |
| Arg | Asp | Glu | Val | Ala | Gln | Met | Tyr | Cys | Leu | Val | Lys | Asp | Trp | Pro | Pro |
| | | | 580 | | | | | 585 | | | | | 590 | | |
| Ile | Lys | Pro | Glu | Gln | Ala | Met | Glu | Leu | Leu | Asp | Cys | Asn | Tyr | Pro | Asp |
| | | 595 | | | | | 600 | | | | | 605 | | | |
| Pro | Met | Val | Arg | Gly | Phe | Ala | Val | Arg | Cys | Leu | Glu | Lys | Tyr | Leu | Thr |
| | 610 | | | | | 615 | | | | | 620 | | | | |
| Asp | Asp | Lys | Leu | Ser | Gln | Tyr | Leu | Ile | Gln | Leu | Val | Gln | Val | Leu | Lys |
| 625 | | | | | 630 | | | | | 635 | | | | | 640 |
| Tyr | Glu | Gln | Tyr | Leu | Asp | Asn | Leu | Leu | Val | Arg | Phe | Leu | Leu | Lys | Lys |
| | | | | 645 | | | | | 650 | | | | | 655 | |
| Ala | Leu | Thr | Asn | Gln | Arg | Ile | Gly | His | Phe | Phe | Phe | Trp | His | Leu | Lys |
| | | | 660 | | | | | 665 | | | | | 670 | | |
| Ser | Glu | Met | His | Asn | Lys | Thr | Val | Ser | Gln | Arg | Phe | Gly | Leu | Leu | Leu |
| | | 675 | | | | | 680 | | | | | 685 | | | |
| Glu | Ser | Tyr | Cys | Arg | Ala | Cys | Gly | Met | Tyr | Leu | Lys | His | Leu | Asn | Arg |
| | 690 | | | | | 695 | | | | | 700 | | | | |
| Gln | Val | Glu | Ala | Met | Glu | Lys | Leu | Ile | Asn | Leu | Thr | Asp | Ile | Leu | Lys |
| 705 | | | | | 710 | | | | | 715 | | | | | 720 |
| Gln | Glu | Lys | Lys | Asp | Glu | Thr | Gln | Lys | Val | Gln | Met | Lys | Phe | Leu | Val |
| | | | | 725 | | | | | 730 | | | | | 735 | |
| Glu | Gln | Met | Arg | Arg | Pro | Asp | Phe | Met | Asp | Ala | Leu | Gln | Gly | Phe | Leu |
| | | | 740 | | | | | 745 | | | | | 750 | | |
| Ser | Pro | Leu | Asn | Pro | Ala | His | Gln | Leu | Gly | Asn | Leu | Arg | Leu | Glu | Glu |
| | | 755 | | | | | 760 | | | | | 765 | | | |
| Cys | Arg | Ile | Met | Ser | Ser | Ala | Lys | Arg | Pro | Leu | Trp | Leu | Asn | Trp | Glu |
| | 770 | | | | | 775 | | | | | 780 | | | | |
| Asn | Pro | Asp | Ile | Met | Ser | Glu | Leu | Leu | Phe | Gln | Asn | Asn | Glu | Ile | Ile |
| 785 | | | | | 790 | | | | | 795 | | | | | 800 |
| Phe | Lys | Asn | Gly | Asp | Asp | Leu | Arg | Gln | Asp | Met | Leu | Thr | Leu | Gln | Ile |
| | | | | 805 | | | | | 810 | | | | | 815 | |
| Ile | Arg | Ile | Met | Glu | Asn | Ile | Trp | Gln | Asn | Gln | Gly | Leu | Asp | Leu | Arg |
| | | | 820 | | | | | 825 | | | | | 830 | | |
| Met | Leu | Pro | Tyr | Gly | Cys | Leu | Ser | Ile | Gly | Asp | Cys | Val | Gly | Leu | Ile |
| | | 835 | | | | | 840 | | | | | 845 | | | |
| Glu | Val | Val | Arg | Asn | Ser | His | Thr | Ile | Met | Gln | Ile | Gln | Cys | Lys | Gly |
| | 850 | | | | | 855 | | | | | 860 | | | | |
| Gly | Leu | Lys | Gly | Ala | Leu | Gln | Phe | Asn | Ser | His | Thr | Leu | His | Gln | Trp |
| 865 | | | | | 870 | | | | | 875 | | | | | 880 |
| Leu | Lys | Asp | Lys | Asn | Lys | Gly | Glu | Ile | Tyr | Asp | Ala | Ala | Ile | Asp | Leu |
| | | | | 885 | | | | | 890 | | | | | 895 | |
| Phe | Thr | Arg | Ser | Cys | Ala | Gly | Tyr | Cys | Val | Ala | Thr | Phe | Ile | Leu | Gly |
| | | | 900 | | | | | 905 | | | | | 910 | | |
| Ile | Gly | Asp | Arg | His | Asn | Ser | Asn | Ile | Met | Val | Lys | Asp | Asp | Gly | Gln |
| | | 915 | | | | | 920 | | | | | 925 | | | |
| Leu | Phe | His | Ile | Asp | Phe | Gly | His | Phe | Leu | Asp | His | Lys | Lys | Lys | Lys |
| | 930 | | | | | 935 | | | | | 940 | | | | |
| Phe | Gly | Tyr | Lys | Arg | Glu | Arg | Val | Pro | Phe | Val | Leu | Thr | Gln | Asp | Phe |
| 945 | | | | | 950 | | | | | 955 | | | | | 960 |

-continued

```
        Leu  Ile  Val  Ile  Ser  Lys  Gly  Ala  Gln  Cys  Thr  Lys  Thr  Arg  Glu
                       965                 970                          975

Phe  Glu  Arg  Phe  Gln  Glu  Met  Cys  Tyr  Lys  Ala  Tyr  Leu  Ala  Ile  Arg
                  980                      985                          990

Gln  His  Ala  Asn  Leu  Phe  Ile  Asn  Leu  Phe  Ser  Met  Met  Leu  Gly  Ser
             995                      1000                     1005

Gly  Met  Pro  Glu  Leu  Gln  Ser  Phe  Asp  Asp  Ile  Ala  Tyr  Ile  Arg  Lys
             1010                     1015                     1020

Thr  Leu  Ala  Leu  Asp  Lys  Thr  Glu  Gln  Glu  Ala  Leu  Glu  Tyr  Phe  Met
        1025                     1030                     1035                     1040

Lys  Gln  Met  Asn  Asp  Ala  His  His  Gly  Gly  Trp  Thr  Thr  Lys  Met  Asp
                            1045                     1050                     1055

Trp  Ile  Phe  His  Thr  Ile  Lys  Gln  His  Ala  Leu  Asn  Xaa
                       1060                     1065
```

( 2 ) INFORMATION FOR SEQ ID NO: 38:

( i ) SEQUENCE CHARACTERISTICS:
( A ) LENGTH: 381 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 1..381

( x i ) SEQUENCE DESCRIPTION: SEQ ID NO: 38:

```
GGA  GAC  GAC  TTG  CGA  CAG  GAT  CAA  CTT  ATT  CTT  CAA  ATC  ATT  TCA  CTC        48
Gly  Asp  Asp  Leu  Arg  Gln  Asp  Gln  Leu  Ile  Leu  Gln  Ile  Ile  Ser  Leu
 1                   5                        10                      15

ATG  GAC  AAG  CTG  TTA  CGG  AAA  GAA  AAT  CTG  GAC  TTG  AAA  TTG  ACA  CCT        96
Met  Asp  Lys  Leu  Leu  Arg  Lys  Glu  Asn  Leu  Asp  Leu  Lys  Leu  Thr  Pro
              20                        25                      30

TAT  AAG  GTG  TTA  GCC  ACC  AGT  ACA  AAA  CAT  GGC  TTC  ATG  CAG  TTT  ATC       144
Tyr  Lys  Val  Leu  Ala  Thr  Ser  Thr  Lys  His  Gly  Phe  Met  Gln  Phe  Ile
         35                        40                        45

CAG  TCA  GTT  CCT  GTG  GCT  GAA  GTT  CTT  GAT  ACA  GAG  GGA  AGC  ATT  CAG       192
Gln  Ser  Val  Pro  Val  Ala  Glu  Val  Leu  Asp  Thr  Glu  Gly  Ser  Ile  Gln
     50                        55                        60

AAC  TTT  TTT  AGA  AAA  TAT  GCA  CCA  AGT  GAG  AAT  GGG  CCA  AAT  GGG  ATT       240
Asn  Phe  Phe  Arg  Lys  Tyr  Ala  Pro  Ser  Glu  Asn  Gly  Pro  Asn  Gly  Ile
 65                       70                        75                       80

AGT  GCT  GAG  GTC  ATG  GAC  ACT  TAC  GTT  AAA  AGC  TGT  GCT  GGA  TAT  TGC       288
Ser  Ala  Glu  Val  Met  Asp  Thr  Tyr  Val  Lys  Ser  Cys  Ala  Gly  Tyr  Cys
                    85                        90                       95

GTG  ATC  ACC  TAT  ATA  CTT  GGA  GTT  GGA  GAC  AGG  CAC  CTG  GAT  AAC  CTT       336
Val  Ile  Thr  Tyr  Ile  Leu  Gly  Val  Gly  Asp  Arg  His  Leu  Asp  Asn  Leu
              100                      105                      110

TTG  CTA  ACC  AAA  ACA  GGC  AAA  CTC  TTC  CAC  ATC  GAT  TTC  GGC  CAC            381
Leu  Leu  Thr  Lys  Thr  Gly  Lys  Leu  Phe  His  Ile  Asp  Phe  Gly  His
              115                      120                      125
```

( 2 ) INFORMATION FOR SEQ ID NO: 39:

( i ) SEQUENCE CHARACTERISTICS:
( A ) LENGTH: 127 amino acids
( B ) TYPE: amino acid
( D ) TOPOLOGY: linear ( i i ) MOLECULE TYPE: protein ( x i ) SEQUENCE DESCRIPTION: SEQ ID NO: 39:

| | | | | | | | | | | | | | | | |
|---|---|---|---|---|---|---|---|---|---|---|---|---|---|---|---|
| Gly | Asp | Asp | Leu | Arg | Gln | Asp | Gln | Leu | Ile | Leu | Gln | Ile | Ile | Ser | Leu |
| 1 | | | | 5 | | | | 10 | | | | | 15 | | |
| Met | Asp | Lys | Leu | Leu | Arg | Lys | Glu | Asn | Leu | Asp | Leu | Lys | Leu | Thr | Pro |
| | | | 20 | | | | 25 | | | | | 30 | | | |
| Tyr | Lys | Val | Leu | Ala | Thr | Ser | Thr | Lys | His | Gly | Phe | Met | Gln | Phe | Ile |
| | | 35 | | | | | 40 | | | | | 45 | | | |
| Gln | Ser | Val | Pro | Val | Ala | Glu | Val | Leu | Asp | Thr | Glu | Gly | Ser | Ile | Gln |
| | 50 | | | | | 55 | | | | | 60 | | | | |
| Asn | Phe | Phe | Arg | Lys | Tyr | Ala | Pro | Ser | Glu | Asn | Gly | Pro | Asn | Gly | Ile |
| 65 | | | | | 70 | | | | 75 | | | | | | 80 |
| Ser | Ala | Glu | Val | Met | Asp | Thr | Tyr | Val | Lys | Ser | Cys | Ala | Gly | Tyr | Cys |
| | | | | 85 | | | | | 90 | | | | | 95 | |
| Val | Ile | Thr | Tyr | Ile | Leu | Gly | Val | Gly | Asp | Arg | His | Leu | Asp | Asn | Leu |
| | | | 100 | | | | | 105 | | | | | 110 | | |
| Leu | Leu | Thr | Lys | Thr | Gly | Lys | Leu | Phe | His | Ile | Asp | Phe | Gly | His | |
| | | 115 | | | | | 120 | | | | | 125 | | | |

( 2 ) INFORMATION FOR SEQ ID NO: 40:

( i ) SEQUENCE CHARACTERISTICS:
        ( A ) LENGTH: 393 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..393

( x i ) SEQUENCE DESCRIPTION: SEQ ID NO: 40:

| | | | | | | | | | | | | | | | | |
|---|---|---|---|---|---|---|---|---|---|---|---|---|---|---|---|---|
| GGG | GAT | GAC | TTA | CGG | CAG | GAC | ATG | CTA | ACG | CTG | CAG | ATG | ATT | CGC | ATC | 48 |
| Gly | Asp | Asp | Leu | Arg | Gln | Asp | Met | Leu | Thr | Leu | Gln | Met | Ile | Arg | Ile | |
| 1 | | | | 5 | | | | 10 | | | | | 15 | | | |
| ATG | AGC | AAG | ATC | TGG | GTC | CAG | GAG | GGG | CTG | GAC | ATG | CGC | ATG | GTC | ATC | 96 |
| Met | Ser | Lys | Ile | Trp | Val | Gln | Glu | Gly | Leu | Asp | Met | Arg | Met | Val | Ile | |
| | | | 20 | | | | 25 | | | | | 30 | | | | |
| TTC | CGC | TGC | TTC | TCC | ACC | GGC | CGG | GGC | AGA | GGG | ATG | GTG | GAG | ATG | ATC | 144 |
| Phe | Arg | Cys | Phe | Ser | Thr | Gly | Arg | Gly | Arg | Gly | Met | Val | Glu | Met | Ile | |
| | | 35 | | | | | 40 | | | | | 45 | | | | |
| CCT | AAT | GCT | GAG | ACC | CTG | CGT | AAG | ATC | CAG | GTG | GAG | CAT | GGG | GTG | ACC | 192 |
| Pro | Asn | Ala | Glu | Thr | Leu | Arg | Lys | Ile | Gln | Val | Glu | His | Gly | Val | Thr | |
| | 50 | | | | | 55 | | | | | 60 | | | | | |
| GGC | TCG | TTC | AAG | GAC | CGG | CCC | CTG | GCA | GAC | CGG | CTG | CAG | AAA | CAC | AAC | 240 |
| Gly | Ser | Phe | Lys | Asp | Arg | Pro | Leu | Ala | Asp | Arg | Leu | Gln | Lys | His | Asn | |
| 65 | | | | | 70 | | | | | 75 | | | | | 80 | |
| CCT | GGG | GAG | GAC | GAG | TAT | GAG | AAG | GCT | GTG | GAG | AAC | TTT | ATC | TAC | TCC | 288 |
| Pro | Gly | Glu | Asp | Glu | Tyr | Glu | Lys | Ala | Val | Glu | Asn | Phe | Ile | Tyr | Ser | |
| | | | | 85 | | | | | 90 | | | | | 95 | | |
| TGC | GCT | GGC | TGC | TGC | GTG | GCC | ACG | TAC | GTC | TTG | GGC | ATC | TGT | GAC | CGA | 336 |
| Cys | Ala | Gly | Cys | Cys | Val | Ala | Thr | Tyr | Val | Leu | Gly | Ile | Cys | Asp | Arg | |
| | | | 100 | | | | | 105 | | | | | 110 | | | |
| CAT | AAT | GAC | AAC | ATC | ATG | CTG | AAG | ACC | ACT | GGT | CAC | ATG | TTC | CAC | ATC | 384 |
| His | Asn | Asp | Asn | Ile | Met | Leu | Lys | Thr | Thr | Gly | His | Met | Phe | His | Ile | |
| | | 115 | | | | | 120 | | | | | 125 | | | | |
| GAC | TTC | GGC | | | | | | | | | | | | | | 393 |
| Asp | Phe | Gly | | | | | | | | | | | | | | |
| | | 130 | | | | | | | | | | | | | | |

( 2 ) INFORMATION FOR SEQ ID NO: 41:

( i ) SEQUENCE CHARACTERISTICS:

(A) LENGTH: 131 amino acids
(B) TYPE: amino acid
(D) TOPOLOGY: linear (ii) MOLECULE TYPE: protein (xi) SEQUENCE DESCRIPTION: SEQ ID NO: 41:

| Gly | Asp | Asp | Leu | Arg | Gln | Asp | Met | Leu | Thr | Leu | Gln | Met | Ile | Arg | Ile |
|---|---|---|---|---|---|---|---|---|---|---|---|---|---|---|---|
| 1 | | | | 5 | | | | | 10 | | | | | 15 | |
| Met | Ser | Lys | Ile | Trp | Val | Gln | Glu | Gly | Leu | Asp | Met | Arg | Met | Val | Ile |
| | | | 20 | | | | | 25 | | | | | 30 | | |
| Phe | Arg | Cys | Phe | Ser | Thr | Gly | Arg | Gly | Arg | Gly | Met | Val | Glu | Met | Ile |
| | | 35 | | | | | 40 | | | | | 45 | | | |
| Pro | Asn | Ala | Glu | Thr | Leu | Arg | Lys | Ile | Gln | Val | Glu | His | Gly | Val | Thr |
| | 50 | | | | | 55 | | | | | 60 | | | | |
| Gly | Ser | Phe | Lys | Asp | Arg | Pro | Leu | Ala | Asp | Arg | Leu | Gln | Lys | His | Asn |
| 65 | | | | | 70 | | | | | 75 | | | | | 80 |
| Pro | Gly | Glu | Asp | Glu | Tyr | Glu | Lys | Ala | Val | Glu | Asn | Phe | Ile | Tyr | Ser |
| | | | | 85 | | | | | 90 | | | | | 95 | |
| Cys | Ala | Gly | Cys | Cys | Val | Ala | Thr | Tyr | Val | Leu | Gly | Ile | Cys | Asp | Arg |
| | | | 100 | | | | | 105 | | | | | 110 | | |
| His | Asn | Asp | Asn | Ile | Met | Leu | Lys | Thr | Thr | Gly | His | Met | Phe | His | Ile |
| | | 115 | | | | | 120 | | | | | 125 | | | |
| Asp | Phe | Gly | | | | | | | | | | | | | |
| | | 130 | | | | | | | | | | | | | |

(2) INFORMATION FOR SEQ ID NO: 42:

(i) SEQUENCE CHARACTERISTICS:
(A) LENGTH: 66 amino acids
(B) TYPE: amino acid
(C) STRANDEDNESS: single
(D) TOPOLOGY: linear (xi) SEQUENCE DESCRIPTION: SEQ ID NO: 42:

| Gly | Asp | Asp | Leu | Arg | Gln | Asp | Gln | Leu | Val | Val | Gln | Ile | Ile | Ser | Leu |
|---|---|---|---|---|---|---|---|---|---|---|---|---|---|---|---|
| 1 | | | | 5 | | | | | 10 | | | | | 15 | |
| Met | Asn | Glu | Leu | Leu | Lys | Asn | Glu | Asn | Val | Asp | Leu | Lys | Leu | Thr | Pro |
| | | | 20 | | | | | 25 | | | | | 30 | | |
| Tyr | Lys | Ile | Leu | Ala | Thr | Gly | Pro | Gln | Glu | Gly | Ala | Ile | Glu | Phe | Ile |
| | | 35 | | | | | 40 | | | | | 45 | | | |
| Pro | Asn | Asp | Thr | Leu | Ala | Ser | Ile | Leu | Ser | Lys | Tyr | His | Gly | Ile | Leu |
| | 50 | | | | | 55 | | | | | 60 | | | | |
| Gly | Tyr | | | | | | | | | | | | | | |
| 65 | | | | | | | | | | | | | | | |

(2) INFORMATION FOR SEQ ID NO: 43:

(i) SEQUENCE CHARACTERISTICS:
(A) LENGTH: 60 amino acids
(B) TYPE: amino acid
(C) STRANDEDNESS: single
(D) TOPOLOGY: linear (xi) SEQUENCE DESCRIPTION: SEQ ID NO: 43:

| Leu | Lys | Leu | His | Tyr | Pro | Asp | Glu | Asn | Ala | Thr | Leu | Gly | Val | Gln | Gly |
|---|---|---|---|---|---|---|---|---|---|---|---|---|---|---|---|
| 1 | | | | 5 | | | | | 10 | | | | | 15 | |
| Trp | Val | Leu | Asp | Asn | Phe | Val | Lys | Ser | Cys | Ala | Gly | Tyr | Cys | Val | Ile |
| | | | 20 | | | | | 25 | | | | | 30 | | |
| Thr | Tyr | Ile | Leu | Gly | Val | Gly | Asp | Arg | His | Leu | Asp | Asn | Leu | Leu | Val |
| | | 35 | | | | | 40 | | | | | 45 | | | |

```
        Thr  Pro  Asp  Gly  His  Phe  Phe  His  Ala  Asp  Phe  Gly
             50                  55                      60
```

( 2 ) INFORMATION FOR SEQ ID NO: 44:

( i ) SEQUENCE CHARACTERISTICS:
        ( A ) LENGTH: 66 amino acids
        ( B ) TYPE: amino acid
        ( C ) STRANDEDNESS: single
        ( D ) TOPOLOGY: linear ( x i ) SEQUENCE DESCRIPTION: SEQ ID NO: 44:

```
        Gly  Asp  Asp  Leu  Arg  Gln  Asp  Gln  Leu  Ile  Leu  Gln  Ile  Ile  Ser  Leu
        1                  5                       10                       15

Met  Asp  Lys  Leu  Leu  Arg  Lys  Glu  Asn  Leu  Asp  Leu  Lys  Leu  Thr  Pro
                       20                      25                      30

Tyr  Lys  Val  Leu  Ala  Thr  Ser  Thr  Lys  His  Gly  Phe  Met  Gln  Phe  Ile
                       35                      40                      45

Gln  Ser  Val  Pro  Val  Ala  Glu  Val  Leu  Asp  Thr  Glu  Gly  Ser  Ile  Gln
                       50                      55                      60

Asn  Phe
        65
```

( 2 ) INFORMATION FOR SEQ ID NO: 45:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( x i ) SEQUENCE DESCRIPTION: SEQ ID NO: 45:

```
        Phe  Arg  Lys  Tyr  Ala  Pro  Ser  Glu  Asn  Gly  Pro  Asn  Gly  Ile  Ser  Ala
        1                  5                       10                       15

Glu  Val  Met  Asp  Thr  Tyr  Val  Lys  Ser  Cys  Ala  Gly  Tyr  Cys  Val  Ile
                       20                      25                      30

Thr  Tyr  Ile  Leu  Gly  Val  Gly  Asp  Arg  His  Leu  Asp  Asn  Leu  Leu  Leu
                       35                      40                      45

Thr  Lys  Thr  Gly  Lys  Leu  Phe  His  Ile  Asp  Phe  Gly
                       50                      55                      60
```

( 2 ) INFORMATION FOR SEQ ID NO: 46:

( i ) SEQUENCE CHARACTERISTICS:
        ( A ) LENGTH: 85 amino acids
        ( B ) TYPE: amino acid
        ( C ) STRANDEDNESS: single
        ( D ) TOPOLOGY: linear ( x i ) SEQUENCE DESCRIPTION: SEQ ID NO: 46:

```
        Gly  Asp  Asp  Leu  Arg  Gln  Asp  Met  Leu  Thr  Leu  Gln  Ile  Ile  Arg  Ile
        1                  5                       10                       15

Met  Glu  Asn  Ile  Trp  Gln  Asn  Gln  Gly  Leu  Asp  Leu  Arg  Met  Leu  Pro
                       20                      25                      30

Tyr  Gly  Cys  Leu  Ser  Ile  Gly  Asp  Cys  Val  Gly  Leu  Ile  Glu  Val  Val
                       35                      40                      45

Arg  Asn  Ser  His  Thr  Ile  Met  Gln  Ile  Gln  Cys  Lys  Gly  Gly  Leu  Lys
                  50                      55                      60

Gly  Ala  Leu  Gln  Phe  Asn  Ser  His  Thr  Leu  His  Gln  Trp  Leu  Lys  Asp
        65                      70                      75                      80

Lys  Asn  Lys  Gly  Glu
```

85

(2) INFORMATION FOR SEQ ID NO: 47:

(i) SEQUENCE CHARACTERISTICS:
  (A) LENGTH: 47 amino acids
  (B) TYPE: amino acid
  (C) STRANDEDNESS: single
  (D) TOPOLOGY: linear (xi) SEQUENCE DESCRIPTION: SEQ ID NO: 47:

```
Ile Tyr Asp Ala Ala Ile Asp Leu Phe Thr Arg Ser Cys Ala Gly Tyr
 1               5                  10                  15
Cys Val Ala Thr Phe Ile Leu Gly Ile Gly Asp Arg His Asn Ser Asn
                20                  25                  30
Ile Met Val Lys Asp Asp Gly Gln Leu Phe His Ile Asp Phe Gly
 35              40                  45
```

(2) INFORMATION FOR SEQ ID NO: 48:

(i) SEQUENCE CHARACTERISTICS:
  (A) LENGTH: 66 amino acids
  (B) TYPE: amino acid
  (C) STRANDEDNESS: single
  (D) TOPOLOGY: linear (xi) SEQUENCE DESCRIPTION: SEQ ID NO: 48:

```
Gly Asp Asp Leu Arg Gln Asp Met Leu Thr Leu Gln Met Ile Arg Ile
 1               5                  10                  15
Met Ser Lys Ile Trp Val Gln Glu Gly Leu Asp Met Arg Met Val Ile
                20                  25                  30
Phe Arg Cys Phe Ser Thr Gly Arg Gly Arg Gly Met Val Glu Met Ile
             35                  40                  45
Pro Asn Ala Glu Thr Leu Arg Lys Ile Gln Val Glu His Gly Val Thr
         50                  55                  60
Gly Ser
 65
```

(2) INFORMATION FOR SEQ ID NO: 49:

(i) SEQUENCE CHARACTERISTICS:
  (A) LENGTH: 65 amino acids
  (B) TYPE: amino acid
  (C) STRANDEDNESS: single
  (D) TOPOLOGY: linear (xi) SEQUENCE DESCRIPTION: SEQ ID NO: 49:

```
Phe Lys Asp Arg Pro Leu Ala Asp Arg Leu Gln Lys His Asn Pro Gly
 1               5                  10                  15
Glu Asp Glu Tyr Glu Lys Ala Val Glu Asn Phe Ile Tyr Ser Cys Ala
                20                  25                  30
Gly Cys Cys Val Ala Thr Tyr Val Leu Gly Ile Cys Asp Arg His Asn
             35                  40                  45
Asp Asn Ile Met Leu Lys Thr Thr Gly His Met Phe His Ile Asp Phe
         50                  55                  60
Gly
 65
```

(2) INFORMATION FOR SEQ ID NO: 50:

(i) SEQUENCE CHARACTERISTICS:
  (A) LENGTH: 62 amino acids
  (B) TYPE: amino acid (C) STRANDEDNESS: single
(D) TOPOLOGY: linear (xi) SEQUENCE DESCRIPTION: SEQ ID NO: 50:

| Gly | Asp | Asp | Leu | Arg | Gln | Asp | Leu | Leu | Gln | Ile | Ile | Met | Glu | Leu | Asp |
|---|---|---|---|---|---|---|---|---|---|---|---|---|---|---|---|
| 1 | | | | 5 | | | | | 10 | | | | | 15 | |

| Leu | Pro | Tyr | Leu | Thr | Gly | Gly | Ile | Glu | Ile | Asn | Gly | Ile | Gly | Leu | Asn |
|---|---|---|---|---|---|---|---|---|---|---|---|---|---|---|---|
| | | | 20 | | | | | 25 | | | | | 30 | | |

| Ile | Asp | Phe | Val | Ser | Cys | Ala | Gly | Tyr | Cys | Val | Thr | Tyr | Ile | Leu | Gly |
|---|---|---|---|---|---|---|---|---|---|---|---|---|---|---|---|
| | | 35 | | | | | 40 | | | | | 45 | | | |

| Gly | Asp | Arg | His | Asp | Asn | Gly | Leu | Phe | His | Ile | Asp | Phe | Gly |
|---|---|---|---|---|---|---|---|---|---|---|---|---|---|
| | 50 | | | | | 55 | | | | | 60 | | |